(12) United States Patent
Bryant et al.

(10) Patent No.: US 9,500,656 B2
(45) Date of Patent: Nov. 22, 2016

(54) METHODS FOR THE IDENTIFICATION, ASSESSMENT, AND TREATMENT OF PATIENTS WITH CANCER THERAPY

(75) Inventors: Barbara M. Bryant, Cambridge, MA (US); Andrew I. Damokosh, West Hartford, CT (US); George Mulligan, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 388 days.

(21) Appl. No.: 11/891,213

(22) Filed: Aug. 9, 2007

(65) Prior Publication Data
US 2008/0064055 A1    Mar. 13, 2008

Related U.S. Application Data

(60) Provisional application No. 60/836,764, filed on Aug. 10, 2006.

(51) Int. Cl.
*C12Q 1/68* (2006.01)
*G01N 33/574* (2006.01)

(52) U.S. Cl.
CPC ....... *G01N 33/57484* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,278,038 B2 * | 10/2012 | Bryant et al. | 435/6.1 |
| 2004/0156854 A1 * | 8/2004 | Mulligan et al. | 424/155.1 |
| 2004/0191782 A1 * | 9/2004 | Wang | 435/6 |
| 2006/0003365 A1 * | 1/2006 | Shaughnessy et al. | 435/6 |
| 2006/0281122 A1 | 12/2006 | Bryant et al. | |

OTHER PUBLICATIONS

Tockman et al (Cancer Res., 1992, 52:2711s-2718s.*
Oesterreich, S et al, 1996 (Clin Cancer Res, 2: 1199-1206.*
Vandesompele J et al, 2003 (Oncogene, 22(3): 456-60).*
Barlow et al, 2004, Blood, 104(11): p. 414A.*
Glinsky et al, 2004, J Clin Invest, 113: 913-923.*
Hansel et al (Am J Pathol, 2003, 163(1): 217-229).*
Kern et al (Cytometry Part B Clin Cytom, 2003, 55(1): 29-36).*
Ginos et al (Cancer Res, 2004, 64: 55-63).*
Tockman et al (Cancer Res., 1992, 52:2711s-2718s).*
De Vos et al (Oncogene, 2002, 21(44): 6848-6857).*
Richardson et al (NEJM, 2005, 352(24): 2487-2498).*
Ball, N. Sharie, et al., "Neuron-specific Hel-N1 and HuD as novel molecular markers of neuroblastoma: a correlation of HuD messenger RNA levels with favorable prognostic features," *Clinical Cancer Research*, vol. 3 (Oct. 1997) pp. 1859-1865.

Mulligan, George, et al., "Gene expression profiling and correlation with outcome in clinical trials of the proteasome inhibitor bortezomib," *Blood*, vol. 109, No. 8 (Apr. 15, 2007) pp. 3177-3188.
Van de Broek, Isabelle, et al., "Clinical significance of chemokine receptor (CCR1, CCR2 and CXCR4) expression in human myeloma cells: the association with disease activity and survival," *The Hematology Journal*, vol. 91, No. 2 (2006) pp. 200-206.
Moldvay, Judith, et al., "Predictive survival markers in patients with surgically resected non-small cell lung carcinoma," *Clinical Cancer Research*, vol. 6 (Mar. 2000) pp. 1125-1134.
Colakovic, S., et al., "Prognostic value of CA125 kinetics and half-life in advanced ovarian cancer," *The International Journal of Biological Markers*, vol. 15, No. 2 (Apr.-Jun. 2000) pp. 147-152.
Oshita, F., et al., "High expression of integrin beta1 and p53 is a greater poor prognostic factor than clinical stage in small-cell lung cancer," *American Journal of Clinical Oncology*, vol. 27, No. 3 (Jun. 2004) pp. 215-219.
Yang, Q., et al., "Prognostic value of Bcl-2 in invasive breast cancer receiving chemotherapy and endocrine therapy," *Oncology Reports*, vol. 10, No. 1 (Jan.-Feb. 2003) pp. 121-125.
Alexandrakis, M. G., et al., "The clinical and prognostic significance of erythrocyte sedimentation rate (ESR), serum interleukin-6 (IL-6) and acute phase protein levels in multiple myeloma," *Clinical Laboratory Haematology*, vol. 25, No. 1 (Feb. 2003) pp. 41-46.
International Search Report and Written Opinion dated Sep. 18, 2008 from corresponding PCT Application PCT/US07/17716, page? cannot publish.
Levine, David M., et al., "Statistics for Managers Using Microsoft Excel;" Fifth Edition, published by Pearson Prentice Hall, Upper Saddle River, New Jersey, 2008, pp. 265-270.
Richardson, Paul G., et al., "Prognostic factors for response parameters and overall survival in patients with multiple myeloma (MM) following treatment with Bortezomib," 45th Annual Meeting of the American Society of Hematology, San Diego, CA, USA, Dec. 6-9, 2003, Poster 1629 (entire poster and magnified central portion of poster).
Durie, Brian G.M. et al., "Magnitude of Response With Myeloma Frontline Therapy Does Not Predict Outcome: Importance of Time to Progression in Southwest Oncology Group Chemotherapy Trials," *Journal of Clinical Oncology*, vol. 22, No. 10 (May 15, 2004) pp. 1857-1863.
Durie, Brian G.M. et al., "International Uniform Response Criteria for Multiple Myeloma," *Leukemia*, vol. 20, (2006) pp. 1467-1473.
Sjostrom, J. et al., "A Multivariate Analysis of Tumour Biological Factors Predicting Response to Cytotoxic Treatment in Advanced Breast Cancer," *British Journal of Cancer*, vol. 78, No. 6 (1998) pp. 812-815.
Glinsky, Gennadi, V., et al., "Gene expression profiling predicts clinical outcome of prostate cancer," The Journal of Clinical Investigation, vol. 113, No. 6 (Mar. 2004) Supplemental Data (21 pages). Downloaded from http://www.jci.org/cgi/content/full/113/6/913/DC1 [on-line], downloaded Nov. 17, 2010.

(Continued)

*Primary Examiner* — Sean Aeder
(74) *Attorney, Agent, or Firm* — Millennium Pharmaceuticals, Inc.

(57) ABSTRACT

The present invention is directed to the identification of predictive markers that can be used to determine whether patients with cancer are expected to demonstrate long term or short term survival times. In particular, the present invention is directed to the use of certain individual and/or combinations of predictive markers, wherein the expression of the predictive markers correlates with expected short term or long term survival. Thus, by examining the expression levels of individual predictive markers and/or predictive markers comprising a marker set, it is possible to determine predicted patient survival.

21 Claims, 6 Drawing Sheets

(56) References Cited

OTHER PUBLICATIONS

Johnson, J. I., et al., "Relationships between drug activity in NCI preclinical in vitro and in vivo models and early clinical trials," *British Journal of Cancer*, vol. 84, No. 10 (2001) pp. 1424-1431.
Harrouseau, JL, et al., "ESMO Minimum Clinical Recommendations for Diagnosis, Treatment and Follow-up of Multiple Myeloma", Ann. Oncol., 2005, vol. 16, Suppl 1, pp. i45-47.
Smith A, et al., "Guidelines on the Diagnosis and Management of Multiple Myeloma 2005", Brittish Journal of Haematology., 2005, vol. 132, pp. 410-451.
Rajkumar SV, et al., "Conventional Therapy and Approach to Management", Best Practice & Research Clinical Haematology, 2005, vol. 18, No. 4, pp. 585-601.

\* cited by examiner

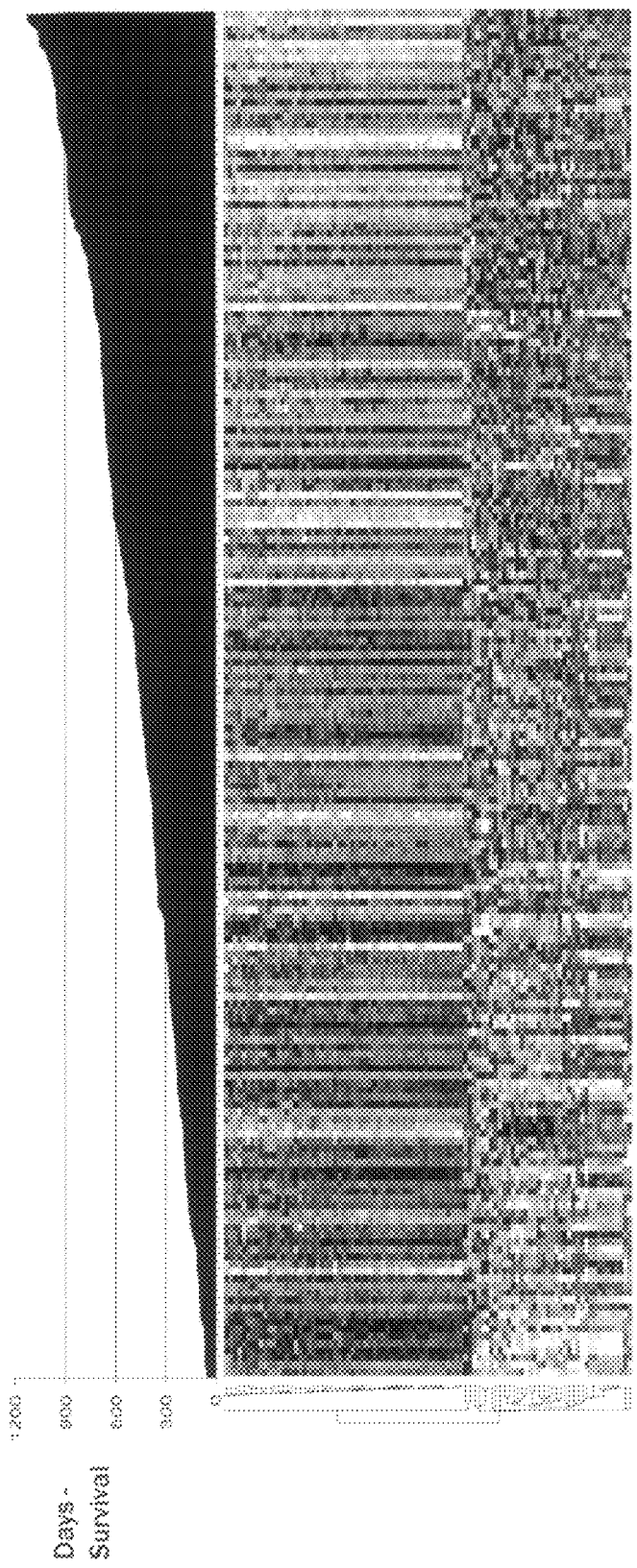

A)

B)

METHODS FOR THE IDENTIFICATION, ASSESSMENT, AND TREATMENT OF PATIENTS WITH CANCER THERAPY

CROSS REFERENCE TO RELATED APPLICATIONS

This application claims the benefit of U.S. Provisional Application No. 60/836,764, filed Aug. 10, 2006. The entire contents of the foregoing application are incorporated herein by this reference.

BACKGROUND OF THE INVENTION

One of the continued problems with therapy in cancer patients is individual differences in response to therapies. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients who are expected to demonstrate enhanced survival periods when administered particular cancer therapies as well as particular cancer patients who may survive longer using more aggressive and/or alternative cancer therapies, e.g., alternative to previous cancer therapies administered to the patient. It would therefore be beneficial to provide for the diagnosis, staging, prognosis, and monitoring of cancer patients, including, e.g., hematological cancer patients (e.g., multiple myeloma, leukemias, lymphoma, etc) as well as solid tumor cancer patients (e.g., lung, breast, prostate, ovary, colon, kidney, liver), who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures.

Proteasome inhibition represents an important strategy in cancer treatment. The proteasome is a multi-enzyme complex present in all cells which play a role in degradation of proteins involved in regulation of the cell cycle. For example, King et al., demonstrated that the ubiquitin-proteasome pathway plays an essential role in regulating cell cycle, neoplastic growth and metastasis. A number of key regulatory proteins, including p53, cyclins, and the cyclin-dependent kinases p21 and p27$^{KIP1}$, are temporally degraded during the cell cycle by the ubiquitin-proteasome pathway. The ordered degradation of these proteins is required for the cell to progress through the cell cycle and to undergo mitosis. See, e.g., *Science* 274:1652-1659 (1996). Furthermore, the ubiquitin-proteasome pathway is required for transcriptional regulation. Palombella et al., teach that the activation of the transcription factor NF-kB is regulated by proteasome-mediated degradation of the inhibitor protein IkB. See International Patent Application Publication No. WO 95/25533. In turn, NF-kB plays a central role in the regulation of genes involved in the immune and inflammatory responses. For example, Read et al. demonstrated that the ubiquitin-proteasome pathway is required for expression of cell adhesion molecules, such as E-selectin, ICAM-1, and VCAM-1. See *Immunity* 2:493-506 (1995). Additional findings further support the role for proteasome inhibition in cancer therapy, as Zetter found that cell adhesion molecules are involved in tumor metastasis and angiogenesis in vivo, by directing the adhesion and extravasation of tumor cells to and from the vasculature to distant tissue sites within the body. See, e.g., *Seminars in Cancer Biology* 4:219-229 (1993). Moreover, Beg and Baltimore, found that NF-kB is an anti-apoptotic factor, and inhibition of NF-kB activation makes cells more sensitive to environmental stress and cytotoxic agents. See *Science* 274:782 (1996).

The first proteasome inhibitor described as having anti-tumor activity, bortezomib (N-pyrazinecarbonyl-L-phenyl-alanine-L-leucineboronic acid, PS-341) (VELCADE® for injection, Millennium Pharmaceuticals, Inc., Cambridge, Mass.; Johnson & Johnson Pharmaceutical Research and Development L.L.C.) has been approved for treatment of relapsed multiple myeloma. Presently clinical trials are underway in additional indications, including additional hematological cancers as well as solid tumors. This and other peptide boronic ester and acid proteasome inhibitors have been described by Adams et al. See, e.g., U.S. Pat. No. 5,780,454 (1998), U.S. Pat. No. 6,066,730 (2000), and U.S. Pat. No. 6,083,903 (2000). They describe the use of the disclosed boronic ester and boronic acid compounds to reduce the rate of muscle protein degradation, to reduce the activity of NF-kB in a cell, to reduce the rate of degradation of p53 protein in a cell, to inhibit cyclin degradation in a cell, to inhibit the growth of a cancer cell, and to inhibit NF-kB dependent cell adhesion.

Bortezomib specifically and selectively inhibits the proteasome by binding tightly ($Ki=0.6$ nM) to one of the enzyme's active sites. Bortezomib is selectively cytotoxic, and has a novel pattern of cytotoxicity in National Cancer Institute (NCI) in vitro and in vivo assays. Adams J, et al. *Cancer Res* 59:2615-22. (1999). In addition, bortezomib has cytotoxic activity in a variety of xenograft tumor models. Teicher B A, et al. *Clin Cancer Res.* 5:2638-45 (1999). Bortezomib inhibits nuclear factor-κB (NF-κB) activation, attenuates interleukin-6 (IL-6) mediated cell growth, and has a direct apoptotic effect, and possibly an anti-angiogenic effect. Additionally, bortezomib is directly cytotoxic to myeloma cells in culture, independent of their p53 status. See, e.g., Hideshima T, et al. *Cancer Res.* 61:3071-6 (2001). In addition to a direct cytotoxic effect of bortezomib on myeloma cells, bortezomib inhibits tumor necrosis factor alpha (TNFα) stimulated intercellular adhesion molecule-1 (ICAM-1) expression by myeloma cells and ICAM-1 and vascular cell adhesion molecule-1 (VCAM-1) expression on bone marrow stromal cells (BMSCs), resulting in decreased adherence of myeloma cells and, consequently, in decreased cytokine secretion. Hideshima T, et al. *Oncogene.* 20:4519-27 (2001). By inhibiting interactions of myeloma cells with the surrounding bone marrow, bortezomib can inhibit tumor growth and survival, as well as angiogenesis and tumor cell migration. The antineoplastic effect of bortezomib may involve several distinct mechanisms, including inhibition of cell growth signaling pathways, dysregulation of the cell cycle, induction of apoptosis, and inhibition of cellular adhesion molecule expression. Notably, bortezomib induces apoptosis in cells that over express B-cell lymphoma 2 (Bcl-2), a genetic trait that confers unregulated growth and resistance to conventional chemotherapeutics. McConkey D J, et al. *The proteasome as a new drug target in metastatic prostate cancer.* 7th Annual Genitourinary Oncology Conference; Houston, Tex. Abstract (1999).

Glucocorticoidal steroids are capable of causing apoptotic death of many varieties of cells, and a selection of glucocorticoidal steroids have consequently been used in the treatment of various malignancies, including lymphoid malignancies, and combination therapies in solid tumors. For example, the optimal therapy for relapsed myeloma is not established, but high-dose dexamethasone is commonly used. See, e.g., Kumar A, et al. *Lancet Oncol;* 4:293-304 (2003); Alexanian R, et al. *Ann Intern Med.* 105:8-11 (1986); Friedenberg W R, et al. *Am J. Hematol.* 36:171-75. (1991). Response rates with this treatment are similar to those with vincristine, doxorubicin, and dexamethasone (VAD), and the dexamethasone component is estimated to account for 85 percent of the effect of VAD. See, e.g., Alexanian R, et al. *Blood.* 80:887-90 (1992); Sonneveld P, et al. *Br J Haematol.* 115:895-902. (2001). High-dose chemotherapy followed by autologous stem cell transplantation improves survival, but in most cases the disease relapses. Attal M et al. *N Engl J Med.* 335:91-97 (1996); Child J A, et al. *N Engl J Med.* 348:1875-83 (2003).

In addition to use of dexamethasone, additional corticosteroids have demonstrated use in cancer treatments, including hydrocortisone in combination therapy for prostate cancer, predisolone in leukemia, prednisolone in lymphoma treatment, and triamcinolone has recently demonstrated some anti-cancer activity. See, e.g., Scholz M., et al., *J. Urol.* 173:1947-52. (2005); Sano J., et al., *Res Vet Sci.* (May 10, 2005); Zinzani P L. et al., *Semin Oncol.* 32(1 Suppl 1):S4-10. (2005); and Abrams, M T et al., *J Cancer Res Clin Oncol.* 131:347-54 (2005). It is believed gene transcription resulting from treatment with glucocorticoids results in apoptotic death and therapeutic effect. Analysis of sensitive and resistant cell lines have demonstrated differential gene expression patterns, suggesting expression differences account for varied success with glucocorticoid therapy. See, e.g., Thompson, E. B., et al., *Lipids.* 39:821-5 (2004), and references cited therein.

While advances in development of successful cancer therapies progress, only a subset of patients respond to any particular therapy. We have conducted gene expression analysis studies on tumor samples from patients undergoing glucocorticoid therapy or proteasome inhibition therapy. Analyses were carried out to identify gene expression markers predictive of patient survival time after treatment. The markers identify particular patients who are expected to show enhanced survival time with treatment (long term survivors), e.g., with a glucocorticoid and/or proteasome inhibitor, as well as those patients who are expected to die sooner (short term survivors) and may require an alternative treatment to and/or more aggressive treatment with a glucocorticoid and/or proteasome inhibitor to increase survival time.

DESCRIPTION OF THE INVENTION

The present invention is based, in part, on the identification of individual markers and marker sets that can be used to determine whether enhanced survival time can be expected by treatment with a proteasome inhibition therapy and/or a glucocorticoid therapy or whether an alternative therapy to and/or a more aggressive therapy with a proteasome inhibitor and/or glucocorticoid inhibitor may enhance expected survival time. For example, the compositions and methods provided herein can be used to determine whether a patient is expected to be a long term or short term survivor to a proteasome inhibition therapeutic agent or a proteosome inhibitor dosing or administration regimen. Furthermore the compositions and methods provided herein can be used to determine whether a patient is expected to be a long term or short term survivor to a glucocorticoid therapeutic agent or a glucocorticoid dosing or administration regimen. Based on these identifications, the present invention provides, without limitation: 1) methods and compositions for determining whether a proteasome inhibition therapy regimen and/or a glucocorticoid therapy regimen will or will not be effective to enhance patient survival time; 2) methods and compositions for monitoring the effectiveness of a proteasome inhibition therapy (a proteasome inhibitor agent or a combination of agents) and/or a glucocorticoid therapy (a glucocorticoid agent or combination of agents) and dosing and administrations used for the treatment of tumors; 3) methods and compositions for treatments of tumors comprising, e.g., proteasome inhibition therapy regimen and/or glucocorticoid therapy regimen; and 4) methods and compositions for identifying specific therapeutic agents and combinations of therapeutic agents as well as dosing and administration regimens that are effective for the treatment of tumors in specific patients.

The markers of the present invention, whose expression are predictive of short term and long term survival after treatment with a proteosome inhibitor and/or glucocorticoid inhibitor, are identified in Table 1 and Table 2. By examining the expression of one or more of the identified markers or marker sets in a tumor, it is possible to determine which therapeutic agent, combination of agents, dosing and/or administration regimen is expected to enhance survival time. By examining the expression of one or more of the identified markers or marker sets in a cancer, it is also possible to determine which therapeutic agent, combination of agents, dosing and/or administration regimen is less likely to enhance survival time. By examining the expression of one or more of the identified markers or marker sets, it is therefore possible to eliminate ineffective or inappropriate therapeutic agents. Importantly, these determinations can be made on a patient by patient basis. Thus, one can determine whether or not a particular therapeutic regimen is likely to benefit a particular patient or type of patient, and/or whether a particular regimen should be started or avoided, continued, discontinued or altered.

The present invention is directed to methods of identifying and/or selecting a cancer patient who is expected to demonstrate enhanced survival to a therapeutic regimen, e.g., as compared to a patient identified as short term survivor receiving the same therapeutic regimen. In particular, the methods are directed to identifying or selecting a cancer patient who is expected to demonstrate enhanced survival to a therapeutic regimen comprising a proteasome inhibitor treatment regimen and/or glucocorticoid treatment regimen. Additionally provided are methods of identifying a patient who is expected to have a reduced survival time to such a therapeutic regimen, e.g., as compared to a patient identified as a long term survivor on the same therapeutic regimen. These methods typically include determining the level of expression of one or more predictive markers in a patient's tumor (e.g., a patient's cancer cells), comparing the level of expression to a reference expression level, and identifying or advising whether expression in the sample includes a pattern or profile of expression of a selected predictive marker or marker set which corresponds to expected long term or short term survival to a treatment regimen, e.g., a proteasome inhibitor treatment regimen and/or glucocorticoid treatment regimen.

Additionally provided methods include therapeutic methods which further include the step of beginning, continuing, or commencing a therapy accordingly where a patient's predictive marker profile indicates that the patient is expected to demonstrate enhanced survival time with the therapy, e.g., the proteasome inhibition and/or glucocorticoid therapeutic regimen. In addition, the methods include therapeutic methods which further include the step of stopping, discontinuing, altering or halting a therapy accordingly where a patient's predictive marker profile indicates that the patient is a long term survivor but is expected to demonstrate similar survival times with an alternative treatment than the proteasome inhibition and/or glucocorticoid therapeutic regimen. In another aspect, the methods include therapeutic methods which further include the step of stopping, discontinuing, altering or halting a therapy regimen accordingly where a patient's predictive marker profile indicates that the patient is expected to demonstrate reduced survival time with the proteasome inhibition and/or glucocorticoid therapeutic regimen, e.g., as compared to a patient identified as a long term survivor receiving the same therapeutic regimen. In another aspect, methods are provided for analysis of a patient not yet being treated with a proteasome inhibition therapy or glucocorticoid therapy and identification and prediction that the patient is expected to be a short term survivor based upon the patient's marker profile. Such methods can include not being treated with the proteasome inhibition therapy and/or glucocorticoid therapy, being treated with proteosome inhibition therapy and/or glucocorticoid therapy in combination with one more additional therapies, being treated with an alternative therapy to proteosome inhibition therapy and/or glucocorticoid therapy, or being treated with a more aggressive dosing and/or administration regimen of a proteosome inhibitor and/or glucocorticoid, e.g., as compared to the dosing and/or administration regimen of a patient identified as a long term survivor. Thus, the provided methods of the invention can eliminate ineffective or inappropriate use of proteasome inhibition therapy and/or glucocorticoid therapy regimens.

Additionally provided are classifiers which can be used to develop a diagnostic test or a readable array useful for identifying patients who are expected to be long term or short term survivors to proteasome inhibition therapy regimen and/or glucocorticoid therapy regimen. Probes or peptides identified in a classifier of the invention can be included in a diagnostic or prognostic test: to select a therapy, e.g., a proteasome inhibition therapy regimen and/or glucocorticoid therapy regimen; to determine continuation or discontinuation of therapy, e.g., a proteasome inhibition therapy regimen and/or glucocorticoid therapy regimen; or to determine a therapy regimen, e.g., a proteosome inhibition therapy regimen and/or glucocorticoid treatment regimen, should be altered, e.g., to a more aggressive therapy and/or therapy regimen.

Additional methods include methods to determine the activity of an agent, the efficacy of an agent, or identify new therapeutic agents or combinations. Such methods include methods to identify an agent as useful, e.g., as a proteasome inhibitor and/or a glucocorticoid inhibitor, for treating a cancer, e.g. a hematological cancer (e.g., multiple myeloma, leukemias, lymphoma, etc) or cancer from a solid tumor (e.g., in lung, breast, prostate, ovary, colon, kidney or liver), based on its ability to affect the expression of markers in a marker set of the invention. For example, an inhibitor which decreases or increases the level of expression of a marker or markers provided as upregulated or downregulated, respectively, in a set predictive for survival time of the patient having cancer would be a candidate inhibitor for the cancer. In another example, an inhibitor which decreases or increases the level of expression of a marker or markers provided as upregulated or downregulated, respectively, in a set predictive for responsiveness to glucocorticoid inhibition of the cancer would be a candidate inhibitor for the cancer. In another example, an inhibitor which decreases or increases the level of expression of a marker or markers provided as upregulated or downregulated, respectively, in a set predictive of short term or long term survival of the cancer would be an alternative candidate to proteasome inhibition and/or glucocorticoid inhibition for the cancer.

The present invention is also directed to methods of treating a cancer patient, with a therapeutic regimen, in particular a proteasome inhibitor therapy regimen (e.g., a proteasome inhibitor agent, alone, or in combination with an additional agent such as a chemotherapeutic agent) and/or glucocorticoid therapy regimen (a glucocorticoid agent, alone or in combination with an additional agent), which includes the step of selecting a patient whose predictive marker profile indicates that the patient is expected to be a long term survivor with the therapeutic regimen, and treating the patient with the proteasome inhibition therapy and/or glucocorticoid therapy. In some embodiments, the method can include the step of selecting a patient whose predictive marker profile indicates that the patient is expected to be a long term survivor and administering a therapy other than proteosome inhibition therapy and/or glucocorticoid therapy that demonstrates similar expected survival times as the proteasome inhibition and/or glucocorticoid therapy.

Additional methods of treating a cancer patient include selecting patients that are unlikely to experience enhanced survival time upon treatment with a cancer therapy (e.g., proteasome inhibition therapy, glucocorticoid therapy). Such methods can further include one or more of: administering a higher dose or increased dosing schedule of a proteasome inhibitor and/or glucocorticoid as compared to the dose or dosing schedule of a patient identified as a long term survivor; administering a cancer therapy other than proteosome inhibition therapy and/or glucocorticoid therapy; administering a proteasome inhibitor agent and/or glucocorticoid agent in combination with an additional agent. Further provided are methods for selection of a patient having aggressive disease which is expected to demonstrate more rapid time to progression and death.

Additional methods include a method to evaluate whether to treat or pay for the treatment of cancer, e.g. hematological cancer (e.g., multiple myeloma, leukemias, lymphoma, etc) or cancer from a solid tumor (e.g., in lung, breast, prostate, ovary, colon, kidney or liver), by reviewing a patient's predictive marker profile for long term or short term survivors to a cancer therapy, e.g., proteasome inhibition and/or glucococorticoid therapy regimen, and making a decision or advising on whether payment should be made.

DESCRIPTION OF THE DRAWINGS

FIG. 2 provides analysis of characteristics of the patients, samples and genes followed in the survival study. FIG. 2B) an overview of the 100 probesets associated with survival (from Table 2), with an expansion of specific functional groups.

DEFINITIONS

Figure 1A:
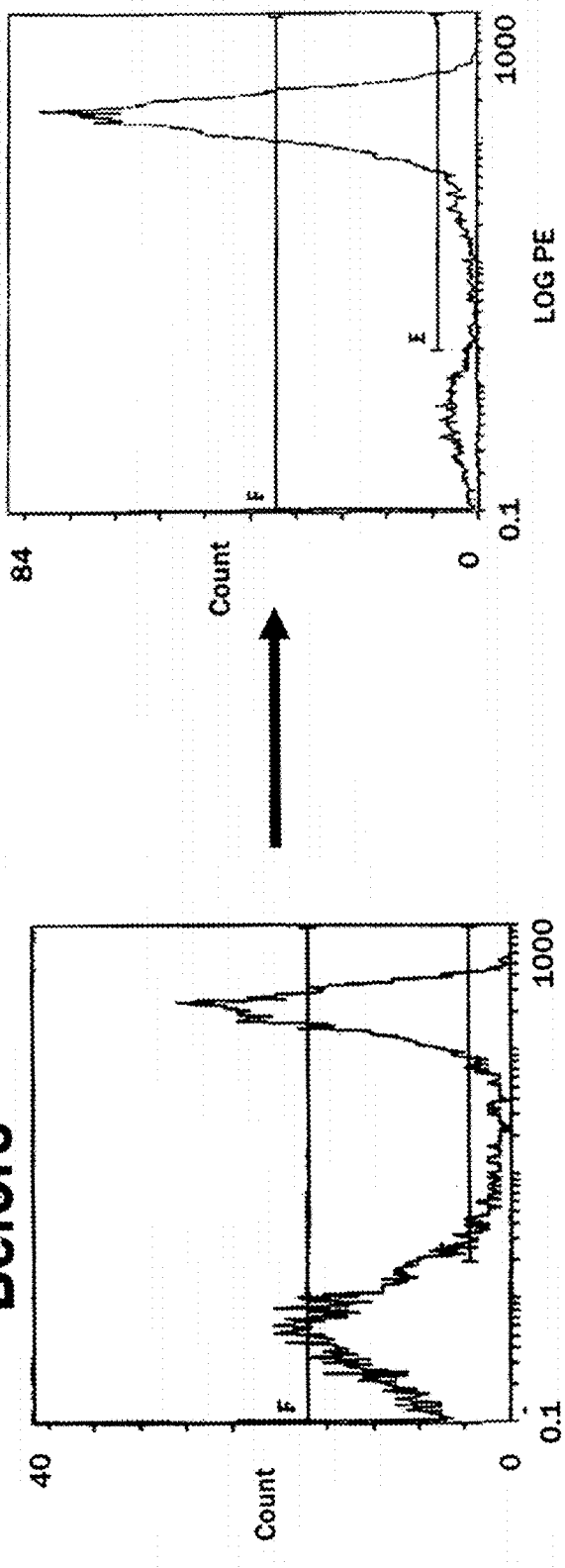
FIG. 1 depicts bone marrow aspirate enrichment procedure effectively depletes non-tumor cells. (A) Bone marrow aspirate samples before and after enrichment were subject to CD138 staining and FACS analysis. (B) Myeloma purity score is elevated in control plasma cell samples (>90% pure) relative to bone marrow mononuclear cells (MNC), neutrophils, & erythroid cells. Two enriched patient samples of 84% and 91% tumor purity by FACS analysis had scores of 35 and 28 respectively (blue arrows). A score of ≥10 (at least 3 fold elevated relative to the score non-PC cell types) was set as a threshold for further analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, preferred methods and materials are described herein. The content of all database accession records (e.g., representative public identifier ID from HG133 annotation files, Entrez, GenBank, RefSeq) cited throughout this application (including the Tables) are also hereby incorporated by reference. The contents of files disclosing the HG-133A Probe Sequences and HG-133B Probe Sequences, both FASTA files dated Jun. 9, 2003 (see website of AFFYMETRIX®, Inc., Santa Clara, Calif.), also hereby are incorporated by reference. In the case of conflict, the present specification, including definitions, will control.

The articles "a" and "an" are used herein to refer to one or to more than one (i.e. at least one) of the grammatical object of the article. By way of example, "an element" means at least one element and can include more than one element.

A "marker" is a naturally-occurring polymer corresponding to at least one of the nucleic acids or proteins associated with AFFYMETRIX® probe set identifiers listed in any one of Table 1 and Table 2. For example, markers include, without limitation, sequences recognized by the Affymetric probes and probeset identifiers, sense and anti-sense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, a "marker" may also include a cDNA made by reverse transcription of an RNA generated by transcription of genomic DNA (including spliced RNA). A "marker set" is a group of markers, comprising two or more (e.g., 5, 10, 15, 20, 25, 30, 35, 40, 45, 50, 60, 75, 100, 200, 300 or 400) predictive markers of the invention. Markers of the present invention include the predictive markers identified in Table 1 and Table 2; as identified by the particular probeset identifier, representative public identifier, title, gene symbol, and/or Entrez gene identifier, and include the representative nucleotide and/or protein sequence or fragment thereof which corresponds to the identifier.

A "predictive marker" as used herein, includes a marker which has been identified as having differential expression in tumor cells of a patient and furthermore that expression is characteristic of a patient whose survival time is expected to be longer or shorter with treatment of a proteasome inhibitor and/or glucocorticoid. For example, a predictive marker includes a marker which demonstrates higher expression in a short term survival patient; alternatively a predictive marker includes a marker which demonstrates higher expression in a long term survival patient. Similarly, a predictive marker is intended to include those markers which demonstrate lower expression in a short term survival patient as well as those markers which demonstrate lower expression in a long term survival patient. Thus, as used herein, predictive marker is intended to include each and every one of these possibilities, and further can include each single marker individually as a predictive marker; or alternatively can include one or more, or all of the characteristics collectively when reference is made to "predictive markers" or "predictive marker sets." A predictive marker set also can be known as a "classifier."

As used herein, a "naturally-occurring" refers to a molecule (e.g., RNA, DNA, protein, etc.) that occurs in nature (e.g., encodes a natural protein, a naturally produced protein, etc).

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of expression of a marker is the level of expression of the marker in cells in a similar environment or response situation, in a patient not afflicted with cancer. A normal level of expression of a marker may also refer to the level of expression of a "reference sample", (e.g., sample from a healthy subjects not having the marker associated disease). A reference sample expression may be comprised of an expression level of one or more markers from a reference database. Alternatively, a "normal" level of expression of a marker is the level of expression of the marker in non-tumor cells in a similar environment or response situation from the same patient that the tumor is derived from.

"Differential expression" of a marker refers to expression of a marker that varies in level across patients. Furthermore, in this invention we refer to a marker as "differentially expressed" when its expression level is correlated with, or otherwise indicative of, long term or short term survival associated with a treatment.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, "informative" expression is intended to refer to the expression level of a differentially expressed predictive marker which corresponds to short term or long term survival. The expression level of a marker in a patient is "informative" if it is greater than a reference level by an amount greater than the standard error of the assay employed to assess expression. The informative expression level of a marker can be determined upon statistical correlation of the measured expression level and the outcome, e.g. short term or long term survival. The result of the statistical analysis can establish a threshold for selecting markers to use in the methods described herein. Alternatively, a marker that is differentially expressed will have typical ranges of expression level that are predictive of short term and long term survival. An informative expression level is a level that falls within the short term and long term survival range of expressions. Still further, a set of markers may together be "informative" if the combination of their expression levels either meets or is above or below a pre-determined score for a predictive marker set as determined by methods provided herein.

A given marker may be indicative of both short term and long term survival in patients; for example, expression of a predictive marker provided herein above a given threshold (e.g., an informative expression level) may be indicative of long term survival in a patient, as described herein. Expression of that marker below a given threshold (e.g., below an informative level) may be indicative of short term survival in a patient A cancer or tumor is treated or diagnosed according to the present methods. "Cancer" or "tumor" is intended to include any neoplastic growth in a patient, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large B-cell lymphoma, malignant lymphoma, plasmocytoma, reticulum cell sarcoma, or Hodgkins disease); and tumors of the nervous system including glioma, meningoma, medulloblastoma, schwannoma or epidymoma.

The terms "long term survivor" and "short term survivor" refer to the length of time after receiving a first dose of treatment that a cancer patient is predicted to live. A "long term survivor" refers to a patient expected have a slower rate of progression and death from the tumor than those patients identified as short term survivors. "Enhanced survival" or "a slower rate of death" are estimated life span determinations based upon elevated or reduced expression of a sufficient number of predictive markers from Table 1 and/or Table 2 as compared to a reference standard such that 70%, 80%, 90% or more of the population will be alive a sufficient time period after receiving a first dose of treatment. A "faster rate of death" or "shorter survival time" refer to estimated life span determinations based upon elevated or reduced expression of a sufficient number of predicted markers from Table 1 and/or Table 2 as compared to a reference standard such that 50%, 40%, 30%, 20%, 10% or less of the population will not live a sufficient time period after receiving a first dose of treatment. Preferably, the sufficient time period is at least 6, 12, 18, 24 or 30 months measured from the first day of receiving a cancer therapy.

"Treatment" shall mean the use of a therapy to prevent or inhibit further tumor growth, as well as to cause shrinkage of a tumor, and to provide longer survival times. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented. Any amelioration of any symptom, physical or otherwise, of a tumor pursuant to treatment using a therapeutic regimen (e.g., proteasome inhibition regimen, glucocorticoid regimen) as further described herein, is within the scope of the invention.

As used herein, the term "agent" is defined broadly as anything that cancer cells, including tumor cells, may be exposed to in a therapeutic protocol. In the context of the present invention, such agents include, but are not limited to, proteasome inhibition agents, glucocorticoidal steroid agents, as well as chemotherapeutic agents as known in the art and described in further detail herein.

A "kit" is any article of manufacture (e.g. a package or container) comprising at least one reagent, e.g. a probe, for specifically detecting a marker or marker set of the invention. The article of manufacture may be promoted, distributed, sold or offered for sale as a unit for performing the methods of the present invention. The reagents included in such a kit comprise probes/primers and/or antibodies for use in detecting short term and long term survival marker expression. In addition, the kits of the present invention may preferably contain instructions which describe a suitable detection assay. Such kits can be conveniently used, e.g., in clinical settings, to diagnose and evaluate patients exhibiting symptoms of cancer, in particular patients exhibiting the possible presence of an a cancer capable of treatment with proteasome inhibition therapy and/or glucocorticoid therapy, including, e.g., hematological cancers e.g., myelomas (e.g., multiple myeloma), lymphomas (e.g., non-hodgkins lymphoma), leukemias, and solid tumors (e.g., lung, breast, ovarian, etc.).

The present methods and compositions are designed for use in diagnostics and therapeutics for a patient suffering from cancer. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver.

The invention provides methods for determining, assessing, advising or providing an appropriate cancer therapy regimen for treating a tumor in a patient. The cancer therapy regimens appropriate for use in or in conjunction with the provided methods include proteasome inhibition therapy regimens and/or glucocorticoid therapy regimens. For example, proteasome inhibitor therapy comprises treatment of a patient with a proteasome inhibitor (e.g., bortezomib, or any other proteasome inhibitor described in further detail herein), alone or in combination with one or more additional agents. In another example, glucocorticoid therapy comprises treatment of a patient with a glucocorticoid (e.g., dexamethasone, or any other glucocorticoid described in further detail herein), alone or in combination with one or more additional agents. A cancer therapy regimen also refers to dose amounts, the frequency of dosing and the number of times a cancer therapy is administered. The terms "dosing schedule" or "administration schedule" as used herein refer to both the frequency of dosing and the number of times a cancer therapy is administered.

The provided methods comprise measuring the level of expression of at least one predictive marker in the patient's tumor and determining or advising on a cancer therapy regimen for treating the tumor based on the expression level of the predictive marker or markers, as relevant. An informative expression level of a predictive marker or markers in the patient sample is an indication that the patient is expected to exhibit longer survival time and would benefit from proteasome inhibition therapy and/or glucocorticoid therapy when the predictive marker or marker set provided herein indicate such survival times. An informative expression level of a predictive marker or markers in the patient sample can also indicate that the patient is expected to exhibit longer survival time and would benefit from an alternative cancer therapy other than proteosome inhibition and/or glucocorticoid therapy that provides similar expectation of survival as the proteasome inhibition and/or glucocorticoid therapy. Additionally, an informative expression level of a predictive marker or markers in a patient is an indication that the patient is not expected to have a long survival time and would not benefit from proteasome inhibition therapy and/or glucocorticoid therapy, or may need a more aggressive therapeutic regimen (e.g., dosing and/or administration regimen) with proteasome inhibition and/or glucocorticoid therapy than a patient classified as a long term survivor when the marker or markers provided herein indicate such short term survival.

The invention further provides methods for determining or advising whether a patient is expected to be a long term survivor in response to a cancer therapy regimen for treating a tumor. Such methods comprise measuring the level of expression of at least one predictive marker in the patient's tumor and determining, advising or providing a proteasome inhibition based regimen and/or glucocorticoid based regimen for treating the tumor based on the expression level of the predictive marker or marker set. An informative expression level of a predictive marker in the patient sample is an indication that the patient is expected to demonstrate long term survival and would benefit from proteasome inhibition and/or glucocorticoid therapy. An informative expression level of a predictive marker set in the patient is an indication that the patient is expected to demonstrate long term survival and would benefit from proteasome inhibition therapy and/or glucocorticoid therapy when the marker or markers provided herein indicate such long term survival. An informative expression level of a predictive marker or markers in the patient sample can also indicate that the patient is expected to exhibit longer survival time and would benefit from an alternative cancer therapy other than proteosome inhibition and/or glucocorticoid therapy that provides similar expectation of survival time as the proteosome inhibition and/or glucocorticoid therapy. Selected predictive markers for use in the methods comprise predictive markers which demonstrate increased expression in long term survival patients and/or which are expected to show longer time to disease progression and death and, e.g., are not specific to treatment with proteosome inhibition therapy or glucocorticoid therapy.

The invention provides methods for determining or advising whether a patient has aggressive disease and is predicted to progress in disease and to death faster than a patient not demonstrating aggressive disease. A patient indicative of having aggressive disease also may be predicted to have short survival time in response to a cancer therapy regimen for treating a tumor. Such methods comprise measuring the level of expression of at least one predictive marker in the patient's tumor and identifying the patient as having aggressive disease based on the expression level of the predictive marker or marker set. An informative expression level of a predictive marker in the patient sample is an indication that the patient has aggressive disease patient and is likely to progress to death more rapidly than a patient determined to be a long term survivor and may not benefit from proteasome inhibition based regimen and/or glucocorticoid based regimen therapy, or may need a more aggressive therapy regimen (e.g., dosing and/or administration regimen) with proteasome inhibition and/or glucocorticoid therapy than a patient classified as a long term survivor. An informative expression level of a predictive marker set in the patient is an indication that the patient is a patient having aggressive disease and would not benefit from proteasome inhibition based regimen and/or glucocorticoid based regimen, or may need a more aggressive therapeutic regimen (e.g., dose and/or administration schedule) with proteasome inhibition and/or glucocorticoid therapy than a patient classified as a long term survivor when the selected marker or marker set provided herein indicate such disease aggressiveness. Selected predictive markers for use in the methods comprise predictive markers which demonstrate increased expression in short term survival patients and/or shorter time to disease progression and death in patients and are not specific to treatment with proteasome inhibition therapy or glucocorticoid therapy. The method can further include determining, advising or providing: an alternative cancer therapy than proteosome inhibition therapy and/or glucocorticoid therapy; an additional cancer therapy or therapies in conjunction with the proteosome inhibition therapy and/or glucocorticoid therapy; alternative dose and/or administration schedule, e.g., than determined, advised or provided for a patient predicted to be a long term survival patient, of a proteosome inhibition therapy and/or glucocorticoid therapy.

The invention further provides methods for treating a tumor in a patient with a proteasome inhibition based therapy regimen and/or glucocorticoid based therapy regimen. Such therapeutic methods comprise measuring the level of expression of at least one predictive marker in a patient's tumor; determining or advising whether a proteasome inhibition based regimen and/or glucocorticoid based regimen for treating the tumor is appropriate based on the expression level of the predictive marker or markers, and treating a patient with a proteasome inhibition based therapy and/or glucocorticoid based therapy when the patient's expression level indicates a long term survival patient. An informative expression level of predictive marker in the patient sample is an indication that the patient is a long term survival patient and would benefit from proteasome inhibition based regimen and/or glucocorticoid based regimen therapy when the predictive marker or marker set provided herein indicate the patient is a long term survival patient.

The invention further provides methods for treating a tumor in a patient with a cancer therapy other than a proteosome inhibition based regimen and/or glucocorticoid based regimen that is predicted to have demonstrate similar survival times. Such therapeutic methods comprise measuring the level of expression of at least one predictive marker in a patient's tumor; determining or advising whether a proteasome inhibition based regimen and/or glucocorticoid based regimen for treating the tumor is appropriate based on the expression level of the predictive marker or markers, and treating a patient with the alternative cancer therapy when the patient's expression level indicates a long term survival patient. An informative expression level of predictive marker in the patient sample is an indication that the patient is a long term survival patient and would benefit from the alternative cancer therapy when the predictive marker or marker set provided herein indicate the patient is a long term survival patient.

The invention provides methods for treating a tumor in a patient identified as a short term survival patient. Such therapeutic methods comprise determining or advising on a cancer therapy regimen based upon expression of at least one predictive marker in a patient's tumor, and treating a patient with the cancer therapy regimen when the patient's expression level indicates a short term survival patient. A cancer therapy regimen can be: a cancer therapy regimen other than a proteosome inhibition therapy regimen and/or glucocorticoid therapy regimen; an additional cancer therapy or therapies administered in conjunction with the proteosome inhibition therapy and/or glucocorticoid therapy; alternative dosing and/or dosage administration, e.g., than determined, advised or provided for a patient predicted to be a long term survival patient, of a proteosome inhibition therapy and/or glucocorticoid therapy.

Methods of the invention use at least one of the predictive markers set forth in any one of Table 1 and Table 2. Additionally, the methods provided can use two, three, four, five, six, or more markers to form a predictive marker set. For example, marker sets selected from the markers in Table 1 and Table 2, can be generated using the methods provided herein and can comprise between two, and all of the markers set forth in Table 1 and/or Table 2 and each and every combination in between (e.g., four selected markers, 16 selected markers, 74 selected markers, etc.). In some embodiments, the predictive marker set comprises at least 5, 10, 15, 20, 25, 30, 35, 40, 45, 50, 55, 60, 100, 150, 200, or 300 or more markers. In some embodiments, the predictive marker set comprises no more than 5, 10, 15, 20, 25, 30, 35, 40, 45, 50, 55, 60, 100, 150, 200, 300, 400, 500, 600, 700, 1,000, 2,000 markers. In some embodiments, the predictive marker set includes a plurality of genes associated with cancer, e.g. a hematological cancer (e.g., multiple myeloma, leukemias, lymphoma, etc) or cancer from a solid tumor (e.g., in lung, breast, prostate, ovary, colon, kidney or liver). In some embodiments, the predictive marker set includes a plurality of markers listed in Table 1 and Table 2. In some embodiments the predictive marker set includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1 and/or Table 2. Selected predictive marker sets can be assembled from the predictive markers provided using methods provided herein and analogous methods known in the art.

Methods of the invention further provide the ability to construct marker sets from the individual predictive markers set forth in Table 1, and Table 2 using the methods described in further detail herein. In a further aspect, more than one marker set can be used in combination for the diagnostic, prognostic and treatment methods provided.

The methods of the invention can be performed such that determination of the level of expression of a predictive marker is measured prior to tumor therapy in order to identify whether the patient is predicted to demonstrate long term survival with a particular cancer therapy regimen, e.g., a proteasome inhibition therapy regimen and/or glucocorticoid therapy regimen.

In addition, the methods of the invention can be performed concurrently with ongoing tumor therapy to determine if long term survival is predicted for a patient receiving proteasome inhibition therapy and/or glucocorticoid therapy or predicted for a patient who will receive additional therapy comprising proteasome inhibition therapy and/or glucocorticoid therapy.

Still further, the methods of the invention can be performed after a tumor therapy has been carried out in order to assess whether the patient is predicted to demonstrate long term survival and/or whether additional cancer therapy regimens should be carried out. Such methods can also be performed to assess future cancer therapy regimens, e.g., future proteosome inhibition therapy regimens and/or glucocorticoid therapy regimens, for the patient.

Whether the methods are performed during ongoing tumor therapy or after a course of tumor therapy, the tumor therapy can comprise proteasome inhibition therapy and/or glucocorticoid therapy, alone or alternative forms of cancer therapy. The methods can determine if the patient will benefit from additional or future proteasome inhibition and/or glucocorticoid therapy regimens, and can include such proteasome inhibition and/or glucocorticoid therapy alone or in combination with additional therapeutic agents.

In certain aspects, the level of expression of predictive marker in the patient's tumor is measured by isolating a sample of the tumor and performing analysis on the isolated sample, or a portion thereof. In another aspect, the level of expression of predictive marker in the patient's tumor is measured using in vivo imaging techniques.

In certain aspects, determining the level of expression of a predictive marker comprises detection of mRNA. Such detection can be carried out by any relevant method, including e.g., PCR, northern, nucleotide array detection, in vivo imaging using probes capable of detection of the appropriate nucleic acid. In other aspects, determining the level of expression of the predictive marker comprises detection of protein. Such detection can be carried out using any relevant method for protein detection, including e.g., ELISA, western blot, immunoassay, protein array detection, in vivo imaging using probes capable of detection of the appropriate peptide.

Determining the level of expression of a predictive marker is compared to a reference expression level. For example, a reference expression level can be a predetermined standard reference level of expression in order to evaluate if expression of a marker or marker set is informative and make an assessment for determining whether the patient is a short term or long term survivor. Additionally, determining the level of expression of a predictive marker can be compared to an internal reference marker level of expression which is measured at the same time as the predictive marker in order to make an assessment for determining whether the patient is a short term or long term survivor. For example, expression of a distinct marker or markers which is/are not predictive markers of the invention, but which is known to demonstrate a constant expression level can be assessed as an internal reference marker level, and the level of the predictive marker expression is determined as compared to the reference. In an alternative example, expression of the selected predictive marker or markers in a tissue sample which is a non-tumor sample can be assessed as an internal reference marker level. The level of expression of a marker or markers may be determined as having increased expression in certain aspects. The level of expression of a marker or markers may be determined as having decreased expression in other aspects. The level of expression may be determined as no informative change in expression as compared to a reference level. In still other aspects, the level of expression is determined against a pre-determined standard expression level as determined by the methods provided herein.

The invention also relates to various reagents and kits for diagnosing, staging, prognosing, monitoring and treating a cancer patient (e.g., a patient with a liquid tumor or a solid tumor), with a cancer therapy regimen, e.g., proteasome inhibition therapy and/or glucocorticoid therapy regimens. Provided are reagents for detection of markers and marker sets and for use in the methods of the invention comprising at least two isolated predictive markers set forth in Table 1 and Table 2. Such reagents include nucleic acid probes, primers, antibodies, antibody derivatives, antibody fragments, and peptide probes for detection of the relevant predictive markers set forth in Table 1 and Table 2.

Further provided are kits for use in the provided methods. The kits of the invention include reagents for assessing predictive markers (e.g., at least one predictive marker) and predictive marker sets (e.g., at least two, three, four or more markers selected from Table 1 and Table 2), as well as instructions for use in accordance with the methods provided herein. In certain aspects, the kits provided contain nucleic acid probes for assessment of predictive markers. In still other aspects, the kits provided contain antibody, antibody derivative antibody fragment, or peptide reagents for assessment of predictive markers.

Identification of Long Term and Short Term Survival Markers

The present invention provides markers that are expressed in a tumor that predict enhanced survival times in a patient receiving a cancer therapy, e.g., proteasome inhibition therapy and/or glucocorticoid therapy, and whose expression correlates with longer survival times in such patients. The present invention also provides markers that are expressed in a tumor that predict shorter survival times for patients receiving a cancer therapy, e.g., a proteasome inhibition therapy and/or glucocorticoid therapy, and whose expression correlates with shorter survival times in such patients. Accordingly, one or more of the markers can be used to identify cancers that can be successfully treated by proteasome inhibition therapy regimens and/or glucocorticoid therapy regimens. One or more of the markers of the present invention can be used to identify patients that can be successfully treated using proteasome inhibition therapy regimens and/or glucocorticoid therapy regimens. In addition, the markers of the present invention can be used to identify a patient that has become or is at risk of becoming refractory to treatment with proteasome inhibition therapy and/or glucocorticoid therapy. The invention also features combinations of markers, referred to herein as "marker sets," that can predict whether a patient is likely to demonstrate long term or short term survival to a cancer therapy regimen, e.g., proteasome inhibition therapy and/or glucocorticoid therapy regimens.

Table 1 sets forth predictive markers identified using statistical analysis applied to samples from 264 patients, which are specific identifiers of overall survival times (OS) in patients receiving proteasome inhibition therapy (e.g., bortezomib) or glucocorticoid therapy (e.g., dexamethasone). In particular, the markers in Table 1 are correlated with a predicted time until death as determined by a Cox proportional hazard analysis, as described in further detail herein. Table 2 also sets forth predictive markers identified using statistical analysis but was derived from a subset of the patients evaluated for the data in Table 1 and was determined using the superpc method of Bair and Tibshirani, as described in further detail herein. The predictive markers of Table 2 are also specific identifiers of overall survival times (OS) in patients receiving proteasome inhibition therapy (e.g., bortezomib) or glucocorticoid therapy (e.g., dexamethasone). The markers in Table 1 and Table 2 are differentially expressed in samples from patients that are predicted to demonstrate short term ("short term survivor) or long term survival ("long term survivor") with the proteosome inhibitor bortezomib or the glucocorticoid dexamethasone. Thus, one would appreciate that the markers identified can function in a predictive model to prospectively identify patients expected to survive for longer periods when treated with proteosome inhibition therapy, including bortezomib or other proteasome inhibition therapies known in the art as well as those described in further detail herein, and/or glucocorticoid therapy, including dexamethasone or other glucocorticoids known in the art as well as those described in further detail herein. Predictors of long time to death are useful as indicators of patients who are likely to progress to death at a slower rate and may be more likely to be responsive to therapy than other patients. Additionally, the predictive markers in Table 1 and Table 2 are correlated with a predicted short time to death ("short term survivors"). These identified predictive markers are useful as indicators of patients who are likely to progress to death at a faster rate, and less likely to be responsive to therapy than other patients.

Table 1 and Table 2 provide predictive markers which are upregulated indicators correlated with shorter time to death. Table 1 and Table 2 also provide predictive markers which are upregulated indicators correlated with longer time to death. Table 1 indicates whether a marker also is identified as a marker for responsiveness or non-responsiveness to a treatment (proteasome inhibition therapy or dexamethasone therapy; see, International Patent Publication No. WO04053066, published Jun. 24, 2004, or U.S. patent application Ser. No. 11/449,195, filed Jun. 8, 2006, the entire contents of each application incorporated herein by reference).

In the methods of the present invention, the level of expression of one or more predictive markers selected from the group consisting of the markers identified in Table 1 and Table 2 is determined. As used herein, the level or amount of expression refers to the absolute level of expression of an mRNA encoded by the marker or the absolute level of expression of the protein encoded by the marker (i.e., whether or not expression is or is not occurring in the cancer cells).

Generally, it is preferable to determine the expression of two or more of the identified short term or long term survival predictive markers, or three or more of the identified short term or long term survival predictive markers, or still further a larger set of the identified short term or long term survival predictive markers, selected from the predictive markers identified in Table 1A and Table 2. Marker sets comprising the predictive markers identified herein can be generated using the methods and predictive markers provided. Thus, it is possible to assess the expression of a panel of short term and long term survival markers using the methods and compositions provided herein.

As an alternative to making determinations based on the absolute expression level of selected markers, determinations may be based on normalized expression levels. Expression levels are normalized by correcting the absolute expression level of a predictive marker by comparing its expression to the expression of a reference marker that is not a predictive marker, e.g., a housekeeping gene that is constitutively expressed. Suitable markers for normalization include housekeeping genes, such as the actin gene. Constitutively expressed genes are known in the art and can be identified and selected according to the relevant tissue and/or situation of the patient and the analysis methods. Such normalization allows one to compare the expression level in one sample, e.g., a tumor sample, to another sample, e.g., a non-tumor sample, or between samples from different sources.

Further, the expression level can be provided as a relative expression level. To determine a relative expression level of a marker or marker set, the level of expression of the predictive marker or marker set is determined for 10 or more individual samples, preferably 50 or more individual samples in order to establish a baseline, prior to the determination of the expression level for the sample in question. To establish a baseline measurement, mean expression level of each of the predictive markers or marker sets assayed in the larger number of samples is determined and this is used as a baseline expression level for the predictive markers or marker sets in question. The expression level of the marker or marker set determined for the test sample (absolute level of expression) is then divided by the mean expression value obtained for that marker or marker set. This provides a relative expression level and aids in identifying extreme cases of short term or long term survival times.

Determining Short Term and Long Term Survival

The expression level (including protein level) of the identified predictive markers of short term/long term survival patients may be used to: 1) determine if a patient can be treated by an agent or combination of agents; 2) determine if a patient is responding to treatment with an agent or combination of agents; 3) select an appropriate agent or combination of agents for treating a patient; 4) select an appropriate dosing and/or administration schedule of an agent or agents; 5) monitor the effectiveness of an ongoing treatment; 6) identify new cancer therapy treatments (either single agent proteasome inhibitor and/or glucocorticoid agents or complementary agents which can be used alternatively or in combination with proteasome inhibition and/or glucocorticoid agents); and 7) identify aggressiveness of a cancer. In particular, the identified predictive markers may be utilized to determine appropriate therapy, to monitor clinical therapy and human trials of a drug being tested for efficacy, and to develop new agents and therapeutic combinations.

A patient being treated with an agent may exhibit a longer time to death if one or more of the corresponding predictive markers identified in rows 225 to 403 Table 1 and/or rows 38 to 100 of Table 2 demonstrate increased expression. Likewise, predisposition of a patient being treated with an agent to exhibit a longer time to death is determined by the methods of the present invention, wherein a marker set can be generated using to the methods described herein and include a subset of the markers identified in rows 225 to 403 of Table 1 and/or rows 38 to 100 of Table 2, and the expression of the marker set is evaluated.

A patient may exhibit a shorter time to death if one or more of the corresponding predictive markers demonstrates informative expression levels. A patient may exhibit a shorter time to death if one or more of the corresponding predictive markers identified in rows 1 to 224 of Table 1 and rows 1 to 37 of Table 2 demonstrate informative increased expression. Likewise, predisposition of a patient being treated with an agent to exhibit a shorter time to death is determined by the methods of the present invention, wherein a marker set can be generated using to the methods described herein and include a subset of the markers identified in rows 1 to 224 of Table 1 and/or rows 1 to 37 of Table 2, and the expression of the marker set is evaluated.

For example, a method of the invention can include determining the expression level of one or more markers, e.g., a plurality of markers, (e.g., 5, 10, 15, 20, 25, 30, 35, 40, 45, 50, 55, 60, 70, 75, 80, 90, 100, 125, 150, or 200 markers) from Table 1 whose hazard ratio is above a particular threshold, e.g. 1.2, 1.4, 1.6, 1.8, 2.0, 2.2, 2.4, 2.6, 2.8, 3.0, 3.2 or 3.5, preferably above 1.5, 2.0, 2.5 or 3.0. A score compiled from expression levels of the markers predicts short term survival if the expression of a certain percentage of the markers, e.g., 50%, 60%, 70%, 80%, 90% or 95% of the markers show high expression. Alternatively, a method of the invention can include determining the expression level of one or more markers, e.g. a plurality of markers, (e.g., 5, 10, 15, 20, 25, 30, 35, 40, 45, 50, 55, 60, 70, 75, 80, 90, 100, 125, 150, or 175 markers) from Table 1 whose hazard ratio is below a particular threshold, e.g., 0.90, 0.80, 0.70, 0.60, 0.50, 0.40, or 0.30, preferably below 0.75, 0.65, 0.55, 0.45 or 0.35. A score compiled from expression levels of the markers predicts long term survival if the expression of a certain percentage of the markers, e.g., 50%, 60%, 70%, 80%, 90% or 95% of the markers show high expression. In another alternative, a method of the invention can include determining the expression level of a combination of markers, some, e.g., a plurality of markers, (e.g., 10, 20, 30, 40, 50, 60) of whose hazard ratio is above a certain level, e.g., 3.0, 2.5, 2.0 or 1.5 and others, e.g., a plurality of markers, (e.g., 10, 20, 30, 40, 50, 60) of whose hazard ratio is below a certain level, e.g., 0.75, 0.65, 0.55 or 0.45 to develop a score wherein high expression level of a higher percentage of markers with high hazard ratios predicts short term survival and high expression level of a higher percentage of markers with low hazard ratios predicts long term survival. An exemplary method can measure the expression levels of 10, 15, 20 or 25 markers from Table 1 with hazard ratios at least 3.0 or 2.8 and the expression levels of 10, 15, 20 or 25 markers from Table 1 with hazard ratios no higher than 0.40 or 0.45 and further combine the levels of expression of such a combination of markers into a score from which short term survival or long term survival can be predicted by the relative percentage or weight of short term survival or long term survival markers having high expression levels.

In another example, a method of the invention can include determining the expression level of one or more markers, e.g. a plurality of markers, (e.g., 5, 10, 15, 20, 25, 30, or markers) from Table 2 whose SuperPC score is above a particular threshold, e.g. 2.2, 2.4, 2.6, 2.8, or 3.0, preferably above 2.3, 2.5, 2.7 or 2.9. A score compiled from expression levels of the markers predicts short term survival if the expression of a certain percentage of the markers, e.g., 50%, 60%, 70%, 80%, 90% or 95% of the markers show high expression. Alternatively, a method of the invention can include determining the expression level of one or more markers, e.g. a plurality of markers, (e.g., 5, 10, 15, 20, 25, 30, 35, 40, 45, 50, or 55, markers) from Table 2 whose SuperPC score is below a particular threshold, e.g., −2.2, −2.4, −2.6, −2.8, or −3.0, preferably below −2.3, −2.5, −2.7 or −2.9. A score compiled from expression levels of the markers predicts long term survival if the expression of a certain percentage of the markers, e.g., 50%, 60%, 70%, 80%, 90% or 95% of the markers show high expression.

In a further example, a method of the invention can include determining the expression level of one or more markers, e.g. a plurality of markers, (e.g., 5, 10, 15, 20, 25, 30, or markers) from Table 2 whose absolute value of the SuperPC score is above a particular threshold, e.g. 2.2, 2.4, 2.6, 2.8, or 3.0, preferably above 2.3, 2.5, 2.7 or 2.9. As an illustration, an exemplary method measuring the expression level of at least 5, 10, or 15 markers with an absolute score of at least 2.8 can determine the level of expression of one marker with a SuperPC score of at least 3.0, one or two markers with a SuperPC score of no higher than −3.0, one, two or three markers with a SuperPC score of at least 2.90, one two or three markers with a SuperPC score of no higher than −2.90, one, two, three or four markers with a SuperPC score of at least 2.80 and/or one, two or three markers with a SuperPC score no higher than −2.80. Table G below can guide the selection of thresholds to identify markers from Table 2 to include in such a method to identify proteasome inhibition therapy or glucacortioid inhibition therapy. For example, a method determining the expression levels of markers SuperPC score has an absolute value threshold of 2.9 (using about 8 markers from Table 2), 2.7 (using about 23 markers from Table 2), 2.5 or 2.4 (using about 53 or about 72 markers from Table 2, respectively) or 2.3 (using about 95 markers from Table 2) can predict survival outcome of proteasome inhibition, e.g., bortezomib therapy. Alternatively, a method determining the expression levels of markers whose SuperPC scores have an absolute value threshold of 2.9 (using about 8 markers from Table 2), 2.8 (using about 16 markers from Table 2), or 2.6 (using about 37 markers from Table 2) can predict survival outcome of glucocorticoid, e.g., dexamethasone therapy.

The method can include determining the expression level of markers associated with particular biological pathways or categories. Tables 1 and 2 identify markers which have been annotated to particular categories or pathways to provide guidance in selecting markers to test. Markers can be selected at least from the categories of oncogenes, tumor suppressor pathway, cancer antigens, NF-κB pathway, hematopoiesis, apoptotic signaling, mitotic signaling, protein homeostasis, oncogenic signaling, adhesion, cell cycle, ubiquitin/proteasome pathway, stem cell, mitochondria function, rapamycin regulated, expressed in lymphoma, expressed in breast cancer, expressed in renal cancer, and/or RNA processing. For example, a method of the invention can include determining the level of expression of markers involved in ubiquitin or proteasome pathway, e.g., markers corresponding proteasome subunits, mitochondrial function, e.g., markers corresponding to mitochondrial ribosome proteins, cancer antigens, e.g., markers corresponding to synovial sarcoma, X breakpoint proteins and/or stem cell markers to predict short term survival. In another example, a method of the invention can include determining the level of expression of markers involved in hematopoiesis, e.g., glycophorin A or B, ankyrin 1, CD36, or myosin light polypeptide 4, and/or adhesion, e.g., tenascin XB, or catenin to predict long term survival. Additional markers can be selected from these categories and are included in Tables 1 or 2 or are readily available to those skilled in the art. Methods of the invention can include a combination of measuring markers from specific categories and measuring markers beyond certain thresholds, as described in the preceding paragraphs. Reagents for measuring the protein or nucleic acid levels of markers annotated according to biological categories are readily obtained from the public knowledge of the respective sequences or are commercially available, as described in later sections.

In one aspect, the predictive marker set for evaluation of expected survival time in a patient having cancer comprises markers selected from those set forth in any of Table 1 and Table 2. Still a further aspect contemplates markers set forth in either Table 1 alone or in combination with markers set for the in Table 2, or alternatively, those markers set forth in Table 2 alone or in combination with Table 1. For example, a marker set can include all the markers set forth in Table 2. Alternatively, a marker set can include all the markers set forth in Table 1.

According to the methods, proteasome inhibition therapy and/or glucocorticoid therapy could be continued where the expression profile indicates long term survival using the evaluation methods described herein. In addition, proteasome inhibition therapy and/or glucocorticoid therapy could be continued but at a more aggressive dose and/or administration schedule where the expression profile indicates short term survival using the evaluation methods described herein.

The present invention provides methods for determining whether a cancer therapy e.g., a proteasome inhibitor and/or glucocorticoid agent, can be used which increases the likelihood that a patient will have a slower time to death comprising evaluating expression of at least one predictive marker or a predictive marker set in a tumor sample; and identifying and/or advising that proteasome inhibition therapy and/or glucocorticoid therapy is or is not appropriate or that a dosing or administration schedule is appropriate or is not appropriate to increase the likelihood that a patient will have a slower time to death based on the evaluation.

The invention provides a method for determining whether a proteasome inhibition therapeutic regimen (e.g., a proteasome inhibitor agent (e.g., bortezomib) alone or in combination with another chemotherapeutic agent) to increase the likelihood that a patient will have a slower time to death comprising determining the expression profile of a predictive marker or predictive marker set; and identifying and/or advising that a proteasome inhibition therapeutic agent is or is not appropriate or that a dosing or administration schedule is appropriate or is not appropriate to increase the likelihood that a patient will have a slower time to death based on the expression profile.

Additionally provided are methods for determining whether a proteasome inhibitor therapy can be used to increase the likelihood that a patient will have a slower time to death, comprising obtaining a sample of tumor cells, evaluating the expression of one or more individual markers or a marker set, both in tumor cells exposed to the agent and in tumor cells that have not been exposed to the proteasome inhibition therapy; and identifying and/or advising that an agent is or is not appropriate or that a dosing or administration schedule is appropriate or is not appropriate to treat the tumor based on the evaluation.

The invention provides a method for determining whether a glucocorticoid regimen (e.g., glucocorticoidal steroid agent (e.g., dexamethasone) alone or in combination with another chemotherapeutic agent) can be used to increase the likelihood that a patient will have a slower time to death comprising determining the expression profile of a predictive marker or predictive marker set; and identifying and/or advising that a glucocorticoid therapeutic agent is or is not appropriate or that a dosing or administration schedule is appropriate or is not appropriate to increase the likelihood that a patient will have a slower time to death based on the expression profile.

Additionally provided are methods for determining whether a glucocorticoid therapy can be used to increase the likelihood a patient will have a slower time to death, comprising obtaining a sample of tumor cells, evaluating the expression of one or more individual markers or a marker set, both in tumor cells exposed to the agent and in tumor cells that have not been exposed to the glucocorticoid therapy; and identifying and/or advising that an agent is or is not appropriate or that a dosing or administration schedule is appropriate or is not appropriate to treat the tumor based on the evaluation.

In such methods, a proteasome inhibition therapy and/or glucocorticoid therapy is determined appropriate to treat the tumor when the expression profile of the predictive marker or predictive marker set demonstrates a long term survivor according to the expression profile of the predictive markers in the presence of the agent. In addition, a proteosome inhibition therapy and/or glucocorticoid therapy is determined to be appropriate to treat the tumor but a more aggressive dose and/or administration schedule when the expression profile of the predicted marker or predictive marker set demonstrates a short term survivor.

The invention also provides a method for determining whether treatment with an proteasome inhibitor therapy and/or glucocorticoid therapy should be initiated in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining one or more samples, followed by determining the level of expression of one or more markers which correspond to markers identified in any of Table 1 and Table 2 in the sample; and initiating proteasome inhibitor therapy when the expression profile of the predictive markers identified in any one of Table 1 and Table 2 is indicative of enhanced survival time with such treatment. Alternatively, the treatment is not initiated, or is initiated at a more aggressive dose and/or administration schedule when the expression profile of the predictive markers identified in any one of Table 1 and Table 2 is indicative of a predicted shorter survival time with the treatment.

Monitoring when a Tumor has Become Refractory

As discussed above, the identified short term and long term survival markers can be used as pharmacodynamic markers to assess whether the tumor has changed in a way to affect predicted survival time. For example, the markers can assess whether the tumor has become refractory to an ongoing treatment (e.g., a proteasome inhibition therapy and/or glucocorticoid therapy). In this example, when the cancer is not responding to a treatment the expression profile of the tumor cells will change: the level or relative expression of one or more of the predictive markers (e.g., those predictive markers identified in Table 1 and Table 2) such that the expression profile represents a short term survivor patient.

In one such use, the invention provides methods for determining or advising whether a cancer therapy comprising proteasome inhibition therapy regimen and/or glucocorticoid therapy regimen should be continued in a cancer patient, comprising determining the expression of at least one predictive marker or a marker set, wherein the markers are selected from those set forth in any of Table 1 and Table 2, in a tumor sample of a patient exposed to a proteasome inhibition therapy and/or glucocorticoid therapy; and continuing treatment when the expression profile of the marker or marker set demonstrates that the patient is a long term survivor.

In another such use, the invention provides methods for determining or advising whether a cancer therapy comprising proteasome inhibition therapy regimen and/or glucocorticoid therapy regimen should be continued in a cancer patient, comprising determining the expression of at least one predictive marker or a marker set, wherein the markers are selected from those set forth in any of Table 1 and Table 2, in a tumor sample of a patient exposed to a proteasome inhibition therapy and/or glucocorticoid therapy; and altering the therapy to an alternative agent or agents other than proteosome inhibitors and/or glucocorticoids that is expected to have a similar effect on survival when the expression profile of the marker or marker set demonstrates that the patient is a long term survivor.

In another such use, the invention provides methods for determining or advising whether a cancer therapy comprising proteasome inhibition therapy regimen and/or glucocorticoid therapy regimen should be continued in a cancer patient, comprising determining the expression of at least one predictive marker or a marker set, wherein the markers are selected from those set forth in any of Table 1 and Table 2, in a tumor sample of a patient exposed to a proteasome inhibition therapy and/or glucocorticoid therapy; and altering the treatment, e.g., administer in conjunction with other chemotherapeutic agents and/or apply a more aggressive dose and/or administration schedule when the expression profile of the marker or marker set demonstrates that the patient is a short term survivor.

In another such use, the invention provides methods for determining whether a proteasome inhibition therapy and/or glucocorticoid therapy should be discontinued in a cancer patient, comprising determining the expression of at least one predictive marker or a predictive marker set, wherein the markers are selected from those set forth in any of Table 1 and Table 2 in a tumor sample of a patient exposed to a proteasome inhibition therapy and/or glucocorticoid therapy; and discontinuing or altering treatment when the expression profile of the markers identified in any one of Table 1 and Table 2 demonstrates that the patient is a short term survivor.

As used herein, a patient refers to any subject having cancer. [The subject may be a human patient undergoing proteasome inhibition (e.g., bortezomib or other related agent) and/or glucocorticoid (e.g., dexamethasone) therapy using a sole therapeutic agent. The subject may be a human patient undergoing proteasome inhibition (e.g., bortezomib or other related agent) and/or glucocorticoid (e.g., dexamethasone) therapy using a therapeutic agent in conjunction with another agent (e.g., a chemotherapy treatment). The present invention also includes comparing two or more samples obtained from a patient undergoing anti-cancer treatment including proteasome inhibition therapy and/or glucocorticoid therapy. In general, it is conceivable to obtain a first sample from the patient prior to beginning therapy and one or more samples during treatment. In such a use, a baseline of expression prior to therapy is determined, then changes in the baseline state of expression is monitored during the course of therapy. Alternatively, two or more successive samples obtained during treatment can be used without the need of a pre-treatment baseline sample. In such a use, the first sample obtained from the subject is used as a baseline for determining whether the expression of a particular marker or marker set is increasing or decreasing].

In general, when monitoring the effectiveness of a therapeutic treatment, two or more samples from a patient are examined. In another aspect, three or more successively obtained samples are used, including at least one pretreatment sample.

The invention provides methods for determining whether treatment with a proteasome inhibitor therapy regimen should be continued in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of a proteasome inhibition therapy regimen, followed by evaluating the expression of one or more markers which correspond to markers identified in any of Table 1 and Table 2 in the two or more samples; and continuing the treatment when the expression profile of the predictive markers identified in any one of Table 1, and Table 2 is indicative of a long term or short term survivor during the course of the treatment. In such methods, a proteasome inhibition therapy and regimen is determined appropriate to treat the patient when the expression profile of the predictive marker or predictive marker set more typifies long term survival or less typifies short term survival according to the expression profile of the predictive markers in the presence of the agent.

Additionally provided are methods for determining whether treatment with a proteasome inhibitor therapy regimen should be continued in a patient selected from a multiple myeloma patient, a lymphoma patient, a leukemia patient, a lung cancer patient, a breast cancer patient, and an ovarian cancer patient, a prostate cancer patient, a colon cancer patient, a kidney cancer patient, and a liver cancer patient; comprising obtaining two or more samples of tumor cells from a patient at different times during the course of anti-cancer therapy treatment, followed by evaluating the expression of a predictive marker set comprising markers identified in any of Table 1 and Table 2 in the two or more samples; and continuing the treatment when the expression profile of the predictive marker set more typifies long term survival or less typifies short term survival according to the expression during the course of treatment. Alternatively, the treatment is discontinued when the expression profile of the marker set more typifies short term survival and/or less typifies long term survival during the course of treatment.

Certain aspects of the invention relate to methods of treatment and/or diagnosis of a patient with cancer utilizing samples. The source of the cancer cells used in the present methods will be based on how the method of the present invention is being used. For example, if the method is being used to determine whether a patient's cancer can be treated with an agent, or a combination of agents, or a particular dosage and/or administration therapy regimen then the preferred source of sample will be cancer cells obtained from a tumor from the patient, e.g., a tumor biopsy (including a solid or a liquid tumor), a blood sample, a plasma sample, a urine sample, a saliva sample, a lymph sample or other sample can be used. A sample obtained from a tumor can be enriched for tumor cells to increase the specificity of the analysis. A variety of methods known in the art can be used to enrich for tumor cells, including differential centrifugation, fluorescence cell sorting analysis (FACS), isolating cells based on growth independent of substrate attachment, binding to a selection agent, e.g. to an antibody to a tumor marker and furthermore attaching the antibody and thus the bound tumor cell to a solid support, etc, or conversely, an antibody to a marker on a non-tumor cell, e.g. an antibody to CD14 (monocytes), CD2 (T and NK cells), CD33 (myeloid progenitors and monocytes), CD41 (platelets and megakaryocytes), CD45RA (naïve B and T cells) and/or CD66b (granulocytes) and removing the non-tumor cell using the bound antibody, etc. Alternatively, a cancer cell line similar to the type of cancer being treated can be assayed. For example, if multiple myeloma is being treated, then a myeloma cell line can be used. If the method is being used to predict or monitor the effectiveness of a therapeutic protocol, then a tissue or blood sample from a patient being treated is a preferred source.

A skilled artisan can readily select and obtain the appropriate cancer cells that are used in the present method. For cancer cell lines, sources such as The National Cancer Institute, Bethesda, Md., for the NCl-60 cancer cell panel, are preferred. Other cell lines (e.g. from American Type Culture Collection (ATCC®), Manassas, Va.), e.g. myeloma cell lines (e.g., RPMI-8226 or U266) or cell lines of other tumors, e.g. B-cell lymphoma (BC-3), colon tumor (HCT 116), breast tumor (MDA-MB-231), cervical tumor (HeLa), lung tumor (A549), melanoma (A375) or prostate tumor (22Rv 1) or normal cells e.g. from kidney (HEK293) can be used. For cancer cells obtained from a patient, standard biopsy methods, such as a needle biopsy, can be employed.

Myeloma samples were used to identify the markers of the present invention. Further, the expression level of markers can be evaluated in other tissue types including disorders of related hematological cell types, including, e.g., Waldenstroms macrogobulinemia, Myelodysplastic syndrome and other hematological cancers including lymphomas, leukemias, as well as tumors of various solid tissues. It will thus be appreciated that cells from other hematologic malignancies including, e.g., B-cell Lymphomas, Non-Hodgkins Lymphoma, Waldenstrom's syndrome, or other leukemias will be useful in the methods of the present invention. Still further, the predictive markers predicting disease aggressiveness as well as short term and long term survival to agents such as proteasome inhibition therapeutic agents in solid tumors (e.g., lung, breast, prostate, ovary, colon, kidney, and liver), can also be useful in the methods of the present invention.

Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of short term or long term survival. Using expression found in normal tissues as a mean expression score aids in validating whether the short term/long term survival marker or marker set assayed is tumor specific (versus normal cells). Such a later use is particularly important in identifying whether a short term or long term survivor marker or marker set can serve as a target marker or marker set. In addition, as more data is accumulated, the mean expression value can be revised, providing improved relative expression values based on accumulated data.

Detection Assays

Various methods are available to examine the expression of the markers, including gene array/chip technology, RT-PCR, in-situ hybridization, immunohistochemistry, immunoblotting, FISH (fluorescence in-situ hybridization), FACS analyses, northern blot, southern blot or cytogenetic analyses. A skilled artisan can select from these or other appropriate and available methods based on the nature of the marker(s), tissue sample and disease in question. Different methods or combinations of methods could be appropriate in different cases or, for instance in different solid or hematological tumor types.

In certain aspects of the invention, the expression of predictive marker or markers identified in Table 1 and Table 2 is detected by measuring mRNA which corresponds to the predictive marker or marker set. In yet another aspects of the invention, the expression of markers which correspond to markers or marker sets identified in Table 1, and Table 2, is detected by measuring protein which corresponds to the marker or marker set.

An exemplary method for detecting the presence or absence of a nucleic acid or polypeptide corresponding to a marker of the invention in a biological sample involves obtaining a biological sample (e.g. a tumor sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations, in situ hybridizations, and TAQMAN® gene expression assays (Applied Biosystems, Foster City, Calif.) under GLP approved laboratory conditions. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one example of such a method, a sample from a subject, which is to be assayed for presence and/or concentration of marker, can be anchored onto a carrier or solid phase support. In another example, the reverse situation is possible, in which the probe can be anchored to a solid phase and a sample from a subject can be allowed to react as an unanchored component of the assay. One example of such an example includes use of an array or chip which contains a predictive marker or marker set anchored for expression analysis of the sample.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain aspects, the surfaces with immobilized assay components can be prepared in advance and stored. Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein. In one example, when the probe is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another example, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another example, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

The level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of MrRNA can be utilized for the purification of RNA from tumor cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions, e.g., hybridize under conditions of hybridization of 6×SSC at 45° C. and washing in 0.2×SSC, 0.1% SDS at 65° C., to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an AFFYMETRIX® gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental description set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cancer cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a reference gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the markers and marker sets assayed in the larger number of samples is determined and this is used as a baseline expression level for the marker. The expression level of the marker determined for the test sample (absolute level of expression) is then divided by the mean expression value obtained for that marker. This provides a relative expression level.

In another aspect of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. Additional examples of detectable substances are detailed in a later section.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbent assay (ELISA). A skilled artisan can readily adapt known protein/antibody detection methods for use in determining whether a sample comprising cancer cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

Another method for determining the level of a polypeptide corresponding to a marker is mass spectrometry. For example, intact proteins or peptides, e.g., tryptic peptides can be analyzed from a sample, e.g., a tumor biopsy (including a solid or a liquid tumor), a blood sample, a plasma sample, a urine sample, a saliva sample, a lymph sample or other sample, containing one or more polypeptide markers. The method can further include treating the sample to lower the amounts of abundant proteins, e.g. serum albumin, to increase the sensitivity of the method. For example, liquid chromatography can be used to fractionate the sample so portions of the sample can be analyzed separately by mass spectrometry. The steps can be performed in separate systems or in a combined liquid chromatography/mass spectrometry system (LC/MS, see for example, Liao, et al. *Arthritis Rheum.* 50:3792-3803 (2004)). The mass spectrometry system also can be in tandem (MS/MS) mode. The charge state distribution of the protein or peptide mixture can be acquired over one or multiple scans and analyzed by statistical methods, e.g. using the retention time and mass-to-charge ratio (m/z) in the LC/MS system, to identify proteins expressed at statistically significant levels differentially in samples from patients responsive or non-responsive to proteasome inhibition and/or glucocorticoid therapy. Examples of mass spectrometers which can be used are an ion trap system (ThermoFinnigan, San Jose, Calif.) or a quadrupole time-of-flight mass spectrometer (Applied Biosystems, Foster City, Calif.). The method can further include the step of peptide mass fingerprinting, e.g. in a matrix-assisted laser desorption ionization with time-of-flight (MALDI-TOF) mass spectrometry method. The method can further include the step of sequencing one or more of the tryptic peptides. Results of this method can be used to identify proteins from primary sequence databases, e.g. maintained by the National Center for Biotechnology Information, Bethesda, Md., or the Swiss Institute for Bioinformatics, Geneva, Switzerland, and based on mass spectrometry tryptic peptide m/z base peaks.

Electronic Apparatus Readable Arrays

Electronic apparatus, including readable arrays comprising at least one predictive marker of the present invention is also contemplated for use in conjunction with the methods of the invention. As used herein, "electronic apparatus readable media" refers to any suitable medium for storing, holding or containing data or information that can be read and accessed directly by an electronic apparatus. As used herein, the term "electronic apparatus" is intended to include any suitable computing or processing apparatus or other device configured or adapted for storing data or information.

Examples of electronic apparatus suitable for use with the present invention and monitoring of the recorded information include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems. As used herein, "recorded" refers to a process for storing or encoding information on the electronic apparatus readable medium. Those skilled in the art can readily adopt any of the presently known methods for recording information on known media to generate manufactures comprising the markers of the present invention.

For example, microarray systems are well known and used in the art for assessment of samples, whether by assessment gene expression (e.g., RNA detection, protein detection), or metabolite production, for example. Microarrays for use according to the invention include one or more probes of predictive marker(s) of the invention characteristic of response and/or non-response to a therapeutic regimen as described herein. In one embodiment, the microarray comprises one or more probes corresponding to one or more of markers selected from the group consisting of markers which demonstrate increased expression in short term survivors, and genes which demonstrate increased expression in long term survivors in patients. A number of different microarray configurations and methods for their production are known to those of skill in the art and are disclosed, for example, in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 5,981,185; 6,022,963; 6,077,674; 6,156,501; 6,261,776; 6,346,413; 6,440,677; 6,451,536; 6,576,424; 6,610,482; 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; Shena, et al., Tibtech 16:301, 1998; Duggan, et al., Nat. Genet. 21:10, 1999; Bowtell, et al., Nat. Genet. 21:25, 1999; Lipshutz, et al., 21 Nature Genet. 20-24, 1999; Blanchard, et al., 11 Biosensors and Bioelectronics, 687-90, 1996; Maskos, et al., 21 Nucleic Acids Res. 4663-69, 1993; Hughes, et al., Nat. Biotechol. 19:342, 2001; each of which are herein incorporated by reference. A tissue microarray can be used for protein identification (see Hans et al *Blood* 103:275-282 (2004)). A phage-epitope microarray can be used to identify one or more proteins in a sample based on whether the protein or proteins induce auto-antibodies in the patient (Bradford et al. *Urol. Oncol.* 24:237-242 (2006)).

A microarray thus comprises one or more probes corresponding to one or more predictive markers identified in Table 1 and Table 2. The microarray may comprise probes corresponding to, for example, at least 10, at least 15, at least 20, at least 25, at least 30, at least 35, at least 40, at least 45, at least 50, at least 75, at least 100, at least 200, at least 300, or at least 400 predictive markers of the invention predictive of short term or long term survival of a cancer patient. The microarray may comprise probes corresponding to one or more predictive markers as set forth herein. Still further, the microarray may comprise complete marker sets as set forth herein and which may be selected and compiled according to the methods set forth herein. The microarray can be used to assay expression of one or more predictive markers or predictive marker sets in the array. In one example, the array can be used to assay more than one predictive marker or marker set expression in a sample to ascertain an expression profile of markers in the array. In this manner, up to about 44,000 markers can be simultaneously assayed for expression. This allows a profile to be developed showing a battery of markers specifically expressed in one or more samples. Still further, this allows a profile to be developed to assess overall survival.

The array is also useful for ascertaining differential expression patterns of one or more markers in normal and abnormal (e.g., sample, e.g., tumor) cells. This provides a battery of predictive markers that could serve as a tool for ease of identification of short term or long term survival patients. Further, the array is useful for ascertaining expression of reference markers for reference expression levels. In another example, the array can be used to monitor the time course of expression of one or more predictive markers in the array.

In addition to such qualitative determination, the invention allows the quantitation of marker expression. Thus, predictive markers can be grouped on the basis of marker sets or short term or long term survival indications by the level of expression in the sample. This is useful, for example, in ascertaining the short term or long term survival indication of the sample by virtue of scoring the expression levels according to the methods provided herein.

The array is also useful for ascertaining the effect of the expression of a marker on the expression of other predictive markers in the same cell or in different cells. This provides, for example, a selection of alternate molecular targets for therapeutic intervention if patient is predicted to be a short term survivor.

Reagents and Kits

The invention also encompasses kits for detecting the presence of a polypeptide or nucleic acid corresponding to a marker of the invention in a sample (e.g. a tumor sample). Such kits can be used to determine if a subject is likely to demonstrate faster or slower progression to death. In another aspect, the invention provides a test kit for monitoring the efficacy of a compound or therapeutic in a sample. For example, the kit may comprise a labeled probe capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits may further include instructions for use of the provided kits and interpreting the results obtained using the kit; additional reagents for preparation of probes for use in the methods provided; and detectable label, alone or conjugated to the provided probe(s).

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention; (2) a pair of primers useful for amplifying a nucleic acid molecule corresponding to a marker of the invention; or (3) a marker set comprising oligonucleotides which hybridize to at least two nucleic acid sequences encoding polypeptide predictive markers of the invention.

The kit can also comprise, e.g., a buffering agent, a preservative, or a protein stabilizing agent. The kit can further comprise components necessary for detecting the detectable label (e.g., an enzyme or a substrate). For marker sets, the kit can comprise a marker set array or chip for use in detecting the predictive markers. The kit can also contain a reference sample or a series of reference samples which can be assayed and compared to the test sample. Each component of the kit can be enclosed within an individual container and all of the various containers can be within a single package, along with instructions for interpreting the results of the assays performed using the kit.

Therapeutic Agents

The markers and marker sets of the present invention assess the likelihood of short or long term survival in cancer patients, e.g., patients having multiple myeloma. Using this prediction, cancer therapies can be evaluated to design a therapy regimen best suitable for patients in either category.

Therapeutic agents for use in the methods of the invention include a class of therapeutic agents known as proteosome inhibitors As used herein, the term "proteasome inhibitor" refers to any substance which directly inhibits enzymatic activity of the 20S or 26S proteasome in vitro or in vivo. In some embodiments, the proteasome inhibitor is a peptidyl boronic acid. Examples of peptidyl boronic acid proteasome inhibitors suitable for use in the methods of the invention are disclosed in Adams et al., U.S. Pat. Nos. 5,780,454 (1998), 6,066,730 (2000), 6,083,903 (2000); 6,297,217 (2001), 6,465,433 (2002), 6,548,668 (2003), 6,617,317 (2003), and 6,747,150 (2004), each of which is hereby incorporated by reference in its entirety, including all compounds and formulae disclosed therein. Preferably, the peptidyl boronic acid proteasome inhibitor is selected from the group consisting of: N(4 morpholine)carbonyl-.beta.-(1-naphthyl)-L-alanine-L-leucine boronic acid; N(8 quinoline)sulfonyl-.beta.-(1-naphthyl)-L-alanine-L-alanine-L-leucine boronic acid; N(pyrazine)carbonyl-L-phenylalanine-L-leucine boronic acid, and N(4 morpholine)-carbonyl-[O-(2-pyridyl-methyl)]-L-tyrosine-L-leucine boronic acid. In a particular embodiment, the proteasome inhibitor is N (pyrazine)carbonyl-L-phenylalanine-L-leucine boronic acid (bortezomib; VELCADE®; formerly known as MLN341 or PS-341).

Additional peptidyl boronic acid proteasome inhibitors are disclosed in Siman et al., international patent publication WO 99/30707; Bernareggi et al., international patent publication WO 05/021558; Chatterjee et al., international patent publication WO 05/016859; Furet et al., U.S. patent publication 2004/0167337; Furet et al., international patent publication 02/096933; Attwood et al., U.S. Pat. No. 6,018,020 (2000); Magde et al., international patent publication WO 04/022070; and Purandare and Laing, international patent publication WO 04/064755.

Additionally, proteasome inhibitors include peptide aldehyde proteasome inhibitors, such as those disclosed in Stein et al., U.S. Pat. No. 5,693,617 (1997); Siman et al., international patent publication WO 91/13904; Iqbal et al., J. Med. Chem. 38:2276-2277 (1995); and Iinuma et al., international patent publication WO 05/105826, each of which is hereby incorporated by reference in its entirety.

Additionally, proteasome inhibitors include peptidyl epoxy ketone proteasome inhibitors, examples of which are disclosed in Crews et al., U.S. Pat. No. 6,831,099; Smyth et al., international patent publication WO 05/111008; Bennett et al., international patent publication WO 06/045066; Spaltenstein et al. Tetrahedron Lett. 37:1343 (1996); Meng, Proc. Natl. Acad. Sci. 96: 10403 (1999); and Meng, Cancer Res. 59: 2798 (1999), each of which is hereby incorporated by reference in its entirety.

Additionally, proteasome inhibitors include alpha-keto-amide proteasome inhibitors, examples of which are disclosed in Chatterjee and Mallamo, U.S. Pat. Nos. 6,310,057 (2001) and 6,096,778 (2000); and Wang et al., U.S. Pat. Nos. 6,075,150 (2000) and 6,781,000 (2004), each of which is hereby incorporated by reference in its entirety.

Additional proteasome inhibitors include peptidyl vinyl ester proteasome inhibitors, such as those disclosed in Marastoni et al., J. Med. Chem. 48:5038 (2005), and peptidyl vinyl sulfone and 2-keto-1,3,4-oxadiazole proteasome inhibitors, such as those disclosed in Rydzewski et al., J. Med. Chem. 49:2953 (2006); and Bogyo et al., Proc. Natl. Acad. Sci. 94:6629 (1997), each of which is hereby incorporated by reference in its entirety.

Additional proteasome inhibitors include azapeptoids and hydrazinopeptoids, such as those disclosed in Bouget et al., Bioorg. Med. Chem. 11:4881 (2003); Baudy-Floc'h et al., international patent publication WO 05/030707; and Bonnemains et al., international patent publication WO 03/018557, each of which is hereby incorporated by reference in its entirety.

Furthermore, proteasome inhibitors include peptide derivatives, such as those disclosed in Furet et al., U.S. patent publication 2003/0166572, and efrapeptin oligopeptides, such as those disclosed in Papathanassiu, international patent publication WO 05/115431, each of which is hereby incorporated by reference in its entirety.

Further, proteasome inhibitors include lactacystin and salinosporamide and analogs thereof, which have been disclosed in Fenteany et al., U.S. Pat. Nos. 5,756,764 (1998), 6,147,223 (2000), 6,335,358 (2002), and 6,645,999 (2003); Fenteany et al., Proc. Natl. Acad. Sci. USA (1994) 91:3358; Fenical et al., international patent publication WO 05/003137; Palladino et al., international patent publication WO 05/002572; Stadler et al., international patent publication WO 04/071382; Xiao and Patel, U.S. patent publication 2005/023162; and Corey, international patent publication WO 05/099687, each of which is hereby incorporated by reference in its entirety.

Still further, naturally occurring compounds have been recently shown to have proteasome inhibition activity, and can be used in the present methods. For example, TMC-95A, a cyclic peptide, and gliotoxin, a fungal metabolite, have been identified as proteasome inhibitors. See, e.g., Koguchi, Antibiot. (Tokyo) 53:105 (2000); Kroll M, Chem. Biol. 6:689 (1999); and Nam S, J. Biol. Chem. 276: 13322 (2001), each of which is hereby incorporated by reference in its entirety. Additional proteasome inhibitors include polyphenol proteasome inhibitors, such as those disclosed in Nam et al., J. Biol. Chem. 276:13322 (2001); and Dou et al., U.S. patent publication 2004/0186167, each of which is hereby incorporated by reference in its entirety.

Additional therapeutic agents for use in the methods of the invention comprise a known class of therapeutic agents comprising glucocorticoid steroids. Glucocorticoid therapy, generally comprises at least one glucocorticoid agent (e.g., dexamethasone). In certain applications of the invention, the agent used in methods of the invention is a glucocorticoid agent. One example of a glucocorticoid utilized in the treatment of multiple myeloma patients as well as other cancer therapies is dexamethasone. Additional glucocorticoids utilized in treatment of hematological and combination therapy in solid tumors include hydrocortisone, predisolone, prednisone, and triamcinolone. Glucocorticoid therapy regimens can be used alone, or can be used in conjunction with additional chemotherapeutic agents. Chemotherapeutic agents are known in the art and described in further detail herein. Examples of chemotherapeutic agents are set forth in Table A. As with proteasome inhibition therapy, new classes of cancer therapies may be combined with glucocorticoid therapy regimens as they are developed. Finally, the methods of the invention include combination of proteasome inhibition therapy with glucocorticoid therapy, either alone, or in conjunction with further agents.

Further to the above, the language, proteasome inhibition therapy regimen and/or glucocorticoid therapy regimen can include additional agents in addition to proteasome inhibition agents, including chemotherapeutic agents. A "chemotherapeutic agent" is intended to include chemical reagents which inhibit the growth of proliferating cells or tissues wherein the growth of such cells or tissues is undesirable. Chemotherapeutic agents such as anti-metabolic agents, e.g., Ara AC, 5-FU and methotrexate, antimitotic agents, e.g., taxane, vinblastine and vincristine, alkylating agents, e.g., melphanlan, Carmustine (BCNU) and nitrogen mustard, Topoisomerase II inhibitors, e.g., VW-26, topotecan and Bleomycin, strand-breaking agents, e.g., doxorubicin and Mitoxantrone (DHAD), cross-linking agents, e.g., cisplatin and carboplatin (CBDCA), radiation and ultraviolet light. In a preferred embodiment, the agent is a proteasome inhibitor (e.g., bortezomib or other related compounds) are well known in the art (see e.g., Gilman A. G., et al., *The Pharmacological Basis of Therapeutics*, 8th Ed., Sec 12:1202-1263 (1990)), and are typically used to treat neoplastic diseases. The chemotherapeutic agents generally employed in chemotherapy treatments are listed below in Table A.

The agents tested in the present methods can be a single agent or a combination of agents. For example, the present methods can be used to determine whether a single chemotherapeutic agent, such as methotrexate, can be used to treat a cancer or whether a combination of two or more agents can be used in combination with a proteasome inhibitor (e.g., bortezomib) and/or a glucocorticoid agent (e.g., dexamethasone). Preferred combinations will include agents that have different mechanisms of action, e.g., the use of an antimitotic agent in combination with an alkylating agent and a proteasome inhibitor.

The agents disclosed herein may be administered by any route, including intradermally, subcutaneously, orally, intraarterially or intravenously. Preferably, administration will be by the intravenous route. Preferably parenteral administration may be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

TABLE A

Chemotherapeutic Agents

| CLASS | TYPE OF AGENT | NONPROPRIETARY NAMES (OTHER NAMES) |
|---|---|---|
| Alkylating | Nitrogen Mustards | Mechlorethamine ($HN_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| Alkylating | Triazenes | Decarbazine (DTIC; dimethyltriazenoimidazolecarboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | Purine Analogs and Related Inhibitors | Mercaptopuine (6-mercaptopurine; 6-MP) |
| | | Thioguanine (6-thioguanine; TG) |
| | | Pentostatin (2'-deoxycoformycin) |
| | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| Natural Products | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |

TABLE A-continued

Chemotherapeutic Agents

| CLASS | TYPE OF AGENT | NONPROPRIETARY NAMES (OTHER NAMES) |
|---|---|---|
| | | TAXOL |
| | | Taxotere |
| | Enzymes | L-Asparaginase |
| | Biological Response Modifiers | Interfon alfa |
| | | Interleukin 2 |
| | Platinum Coordination Complexes | cis-diamminedichloroplatinum II (CDDP) |
| | | Carboplatin |
| | Anthracendione | Mitoxantrone |
| | Substituted Urea | Hydroxyurea |
| Miscellaneous Agents | Methyl Hydraxzine Derivative | Procarbazine (N-methylhydrazine,(MIH) |
| | Adrenocortical Suppressant | Mitotane (o,p'-DDD) |
| | | Aminoglutethimide |
| Hormones and Antagonists | Progestins | Hydroxyprogesterone caproate |
| | | Medroxyprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

Isolated Nucleic Acid Molecules, Vectors and Host Cells

One aspect of the invention pertains to isolated nucleic acid molecules that correspond to a predictive marker of the invention, including nucleic acids which encode a polypeptide corresponding to a predictive marker of the invention or a portion of such a polypeptide. Isolated nucleic acids of the invention also include nucleic acid molecules sufficient for use as hybridization probes to identify nucleic acid molecules that correspond to a predictive marker of the invention, including nucleic acids which encode a polypeptide corresponding to a predictive marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid encoding a protein corresponding to a marker listed in any one of Table 1 and Table 2, can be isolated and manipulated (e.g., amplified, cloned, synthesized, etc.) using standard molecular biology techniques and the sequence information in the database records described herein. (e.g., described in Sambrook et al., ed., *Molecular Cloning: A Laboratory Manual*, 2nd ed., Cold Spring Harbor Laboratory Press, Cold Spring Harbor, N.Y., 1989).

Moreover, a nucleic acid molecule of the invention can comprise only a portion of a nucleic acid sequence, wherein the full length nucleic acid sequence comprises a predictive marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions, e.g., hybridize under conditions of hybridization of 6×SSC at 45° C. and washing in 0.2× SSC, 0.1% SDS at 65° C., to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more predictive markers of the invention. The probe comprises a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to naturally occurring allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the terms "gene" and "recombinant gene" refer to nucleic acid molecules comprising an open reading frame encoding a polypeptide corresponding to a marker of the invention, including, e.g., sequences which differ, due to degeneracy of the genetic code, from the nucleotide sequence of nucleic acids encoding a protein which corresponds to a marker of the invention, and thus encode the same protein.

As used herein, the phrase "allelic variant" refers to a nucleotide sequence which occurs at a given locus or to a polypeptide encoded by the nucleotide sequence. Such naturally occurring allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of naturally occurring allelic variation and that do not alter the functional activity are intended to be within the scope of the invention.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another aspect, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

The oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a marker of the invention, such that the molecular beacon is useful for quantitating the presence of the predictive marker of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Vectors, including expression vectors, containing a nucleic acid encoding a polypeptide corresponding to a predictive marker of the invention can be used for production of nucleic acid and proteins corresponding to predictive markers of the invention; as well as for production of compositions relating to the predictive markers. Useful vectors further comprise promoter and/or regulatory sequences for effective expression of the nucleic acid and/or protein corresponding to the predictive marker of interest. In certain instances, promoters can include constitutive promoter/regulatory sequences, inducible promoter/regulatory sequences, tissue specific promoter/regulatory sequences, or the naturally occurring endogenous promoter/regulatory sequences corresponding to the predictive marker of interest, as required. Various expression vectors are well known in the art and can be adapted to suit the particular system for expression. For example, recombinant expression vectors of the invention can be designed for expression of a polypeptide corresponding to a marker of the invention in prokaryotic (e.g., E. coli) or eukaryotic cells (e.g., insect cells {using baculovirus expression vectors}, yeast cells or mammalian cells). Suitable host cells are known in the art and include those discussed in Goeddel, supra. Alternatively, the recombinant expression vector can be transcribed and translated in vitro, for example using T7 promoter regulatory sequences and T7 polymerase. Vectors and host cells can be produced using routine methodology known in the art. Furthermore, use of vectors and host cells can be utilized for production of nucleic acids, polypeptides and fragments thereof corresponding to markers of the invention.

Isolated Proteins and Antibodies

One aspect of the invention pertains to isolated proteins which correspond to predictive markers of the invention, and biologically active portions thereof, as well as polypeptide fragments suitable for use as immunogens to raise antibodies directed against a polypeptide corresponding to a predictive marker of the invention. Polypeptides for use in the invention can be isolated, purified, or produced using the gene identification information provided herein in combination with routine molecular biology, protein purification and recombinant DNA techniques well known in the art.

Preferred polypeptides have the amino acid sequence listed in the one of the GenBank and Entrez database records described herein. Other useful proteins are substantially identical (e.g., at least about 70%, preferably 80%, 90%, 95%, or 99%) to one of these sequences and retain the functional activity of the protein of the corresponding naturally-occurring protein yet differ in amino acid sequence due to natural allelic variation or mutagenesis.

The determination of percent identity between two sequences can be accomplished using a mathematical algorithm determining the number of identical positions shared between two sequences. Determination can be carried out using any known method in the art for comparison of identity and similarity. Examples of methods used can include for example, a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used (see the website maintained by the National Center for Biotechnology Information (NCBI), Bethesda, Md.). Another example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2. The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention. Useful fusion proteins can include a His$_6$ tag, a FLAG tag, a c-myc tag, glutathione-S-transferase (GST) tag, a hemagglutinin (HA) tag, a phage T7 gene 10 tag, a V5 tag, an herpes simplex virus (HSV) tag, and a vesicular stomatitis virus (VSV)-G tag, and any other well known heterologous tag for use in fusion protein production. Such fusion proteins can facilitate the purification of a recombinant polypeptide of the invention.

In addition, fusion proteins can include a signal sequence from another protein such as gp67, melittin, human placental alkaline phosphatase, and phoA. In yet another aspect, the fusion protein is an immunoglobulin fusion protein in which all or part of a polypeptide corresponding to a predictive marker of the invention is fused to sequences derived from a member of the immunoglobulin protein family. The immunoglobulin fusion proteins of the invention can be used as immunogens to produce antibodies directed against a polypeptide of the invention in a subject, to purify ligands and in screening assays to identify molecules which inhibit the interaction of receptors with ligands.

An isolated polypeptide corresponding to a predictive marker of the invention, or a fragment thereof, can be used as an immunogen to generate antibodies using standard techniques for polyclonal and monoclonal antibody preparation. For example, an immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. Synthetic and genetically engineered variants (See U.S. Pat. No. 6,331,415) of any of the foregoing are also contemplated by the present invention. Polyclonal and monoclonal antibodies can be produced by a variety of techniques, including conventional murine monoclonal antibody methodology e.g., the standard somatic cell hybridization technique of Kohler and Milstein, *Nature* 256: 495 (1975) the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. See generally, Harlow, E. and Lane, D. (1988) *Antibodies: A Laboratory Manual*, Cold Spring Harbor Laboratory Press, Cold Spring Harbor, N.Y.; and *Current Protocols in Immunology*, Coligan et al. ed., John Wiley & Sons, New York, 1994. Preferably, for diagnostic applications, the antibodies are monoclonal antibodies. Additionally, for use in in vivo applications the antibodies of the present invention are preferably human or humanized antibodies. Hybridoma cells producing a monoclonal antibody of the invention are detected by screening the hybridoma culture supernatants for antibodies that bind the polypeptide of interest, e.g., using a standard ELISA assay.

If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Methods for making human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibody fragments may be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; (vii) a single domain functional heavy chain antibody, which consists of a VHH domain (known as a nanobody) see e.g., Cortez-Retamozo, et al., *Cancer Res.* 64: 2853-2857 (2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. *Science* 242:423-426 (1988); and Huston et al. *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

An antibody directed against a polypeptide corresponding to a predictive marker of the invention (e.g., a monoclonal antibody) can be used to detect the predictive marker (e.g., in a cellular sample) in order to evaluate the level and pattern of expression of the predictive marker. The antibodies can also be used diagnostically to monitor protein levels in tissues or body fluids (e.g. in an tumor sample) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Accordingly, in one aspect, the invention provides substantially purified antibodies or fragments thereof, and non-human antibodies or fragments thereof, which antibodies or fragments specifically bind to a polypeptide comprising an amino acid sequence encoded by a predictive marker identified herein. The substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence which is encoded by a nucleic acid molecule of a predictive marker of the invention. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or antigen binding fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 8, 10, 12, 15, 20 or 25 amino acid residues of an amino acid sequence of the present invention, an amino acid sequence which is at least 95%, 96%, 97%, 98% or 99% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. The substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

The invention also provides a kit containing an antibody of the invention conjugated to a detectable substance, and instructions for use. Still another aspect of the invention is a diagnostic composition comprising an antibody of the invention and a pharmaceutically acceptable carrier. In certain aspects, the diagnostic composition contains an antibody of the invention, a detectable moiety, and a pharmaceutically acceptable carrier.

Sensitivity Assays

A sample of cancerous cells is obtained from a patient. An expression level is measured in the sample for a marker corresponding to at least one of the predictive markers set forth in Table 1 and Table 2. Preferably a marker set is utilized comprising markers identified in Table 1 and/or Table 2, and put together in a marker set using the methods described herein. Such analysis is used to obtain an expression profile of the tumor in the patient. Evaluation of the expression profile is then used to determine whether the patient is a long term survivor and would benefit from proteasome inhibition therapy (e.g., treatment with a proteasome inhibitor (e.g., bortezomib) alone, or in combination with additional agents) and/or glucocorticoid therapy (e.g., treatment with a glucocorticoid (e.g., dexamethasone) alone, or in combination with additional agents), or an alternative agent expected to have a similar effect on survival. Evaluation of the expression profile can also be used to determine whether a patient is a short term survivor and would benefit from a cancer therapy other than proteasome inhibition and/or glucocorticoid therapy or would benefit from an altered proteasome inhibition therapy regimen and/or glucocorticoid therapy regimen. Evaluation can include use of one marker set prepared using any of the methods provided or other similar scoring methods known in the art (e.g., weighted voting, combination of threshold features (CTF), Cox proportional hazards analysis, principal components scoring, linear predictive score, K-nearest neighbor, etc), e.g., using expression values deposited with the Gene Expression Omnibus (GEO) program at the National Center for Biotechnology Information (NCBI, Bethesda, Md.). Data values from this and additional studies are being submitted to this repository for search and retrieval for such statistical methods. Still further, evaluation can comprise use of more than one prepared marker set. A proteasome inhibition therapy and/or glucocorticoid therapy will be identified as appropriate to treat the cancer when the outcome of the evaluation demonstrates a long term survivor or a more aggressive therapy regimen will be identified for a short term survivor.

In one aspect, the invention features a method of evaluating a patient, e.g., a patient with cancer, e.g. a hematological cancer (e.g., multiple myeloma, leukemias, lymphoma, etc) or cancer from a solid tumor (e.g., in lung, breast, prostate, ovary, colon, kidney, or liver) for short term or long term survival. The method includes providing an evaluation of the expression of the markers in a predictive marker set of markers in the patient, wherein the predictive marker set has the following properties: it includes a plurality of genes, each of which is differentially expressed as between patients short term and long term survivor patients and non-afflicted subjects and it contains a sufficient number of differentially expressed markers such that differential expression (e.g., as compared to a level in a non-afflicted reference sample) of each of the markers in the predictive marker set in a subject is predictive of short term or long term survival with no more than about 15%, about 10%, about 5%, about 2.5%, or about 1% false positives (wherein false positive means predicting that a patient as responsive or non-responsive when the subject is not); and providing a comparison of the expression of each of the markers in the set from the patient with a reference value, thereby evaluating the patient.

Examining the expression of one or more of the identified markers or marker sets in a tumor sample taken from a patient during the course of proteasome inhibition therapy and/or glucocorticoid treatment, it is also possible to determine whether the therapeutic agent is continuing to work or whether the cancer has become non-responsive (refractory) to the treatment protocol. For example, a patient receiving a treatment of bortezomib would have tumor cells removed and monitored for the expression of a marker or marker set. If the expression profile of one or more marker sets identified in Table 1 and/or Table 2 more typifies long term survival in the presence of the agent, the treatment with proteasome inhibitor would continue. However, if the expression profile of one or more marker sets identified in Table 1 and/or Table 2 more typifies short term survival in the presence of the agent, then the cancer may have become resistant to proteasome inhibition therapy and/or glucocorticoid therapy, and another treatment protocol should be initiated to treat the patient.

Importantly, these determinations can be made on a patient by patient basis or on an agent by agent (or combinations of agents). Thus, one can determine whether or not a particular proteasome inhibition therapy and/or glucocorticoid therapy is likely to benefit a particular patient or group/class of patients, or whether a particular treatment should be continued.

Use of Information

In one method, information, e.g., about the patient's marker expression levels (e.g., the result of evaluating a predictive marker or predictive marker set described herein), or about whether a patient is expected to be a short term or long term survivor, is provided (e.g., communicated, e.g., electronically communicated) to a third party, e.g., a hospital, clinic, a government entity, reimbursing party or insurance company (e.g., a life insurance company). For example, choice of medical procedure, payment for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information. In the method, informative expression level of a predictive marker or a predictive marker set selected from or derived from Table 1 and/or Table 2 is determined.

In one embodiment, a premium for insurance (e.g., life or medical) is evaluated as a function of information about one or more marker expression levels, e.g., a predictive marker or predictive marker set, e.g., a level of expression associated with short term or long term survival (e.g., the informative expression level). For example, premiums can be increased (e.g., by a certain percentage) if the markers of a patient or a patient's predictive marker set described herein are differentially expressed between an insured candidate (or a candidate seeking insurance coverage) and a reference value (e.g., a non-afflicted person). Premiums can also be scaled depending on marker expression levels, e.g., the result of evaluating a predictive marker or predictive marker set described herein. For example, premiums can be assessed to distribute risk, e.g., as a function of marker expression levels, e.g., the result of evaluating a predictive marker or predictive marker set described herein. In another example, premiums are assessed as a function of actuarial data that is obtained from patients that are short term or long term survivors.

Information about marker expression levels, e.g., the result of evaluating a predictive marker or predictive marker set described herein (e.g., the informative expression level), can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on marker expression levels, e.g., the result of evaluating a predictive marker or predictive marker set described herein, along with one or more other items of information in the profile. An insurance premium or risk assessment can also be evaluated as function of the predictive marker or predictive marker set information. In one implementation, points are assigned on the basis of being a short term or long term survivor.

In one embodiment, information about marker expression levels, e.g., the result of evaluating a predictive marker or predictive marker set described herein, is analyzed by a function that determines whether to authorize the transfer of funds to pay for a service or treatment provided to a subject (or make another decision referred to herein). For example, the results of analyzing a expression of a predictive marker or predictive marker set described herein may indicate that a subject is a short term or long term survivor, suggesting that a treatment course is needed, thereby triggering an outcome that indicates or causes authorization to pay for a service or treatment provided to a subject. In one example, informative expression level of a predictive marker or a predictive marker set selected from or derived from Table 1 and/or Table 2 is determined and payment is authorized if the informative expression level identifies a long term survivor. For example, an entity, e.g., a hospital, care giver, government entity, or an insurance company or other entity which pays for, or reimburses medical expenses, can use the outcome of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payor, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In another aspect, the disclosure features a record (e.g., computer readable record) which includes a list and value of expression for the predictive marker or predictive marker set for a patient. In some embodiments, the record includes more than one value for each marker.

EXEMPLIFICATION

Based on positive findings in multiple myeloma in Phase 1 clinical trials (Orlowski, J Clin Oncol. 2002 Nov. 15; 20(22):4420-7., Aghajanian, Clin Cancer Res. 2002 August; 8(8):2505-11) Phase 2 myeloma studies were conducted in order to allow a more precise estimate of anti-tumor activity of bortezomib in a more homogeneous population of patients. The safety and efficacy of bortezomib in subjects with multiple myeloma was investigated in two phase 2 clinical studies, M34100-024 (subjects with first relapse) and M34100-025 (subjects with second or greater relapse and refractory to their last prior therapy). In Study M34100-025, the CR+PR rate to bortezomib alone was 27% (53 of 193 patients), and the overall response rate (CR+PR+MR) to bortezomib alone was 35% (67 of 193 patients). See Richardson P G, et al. *N Engl J Med.,* 348:2609-17 (2003). In Study M34100-024 CR+PR rates of were 30% and 38% were seen among patients with relapsed multiple myeloma treated with bortezomib 1.0 mg/m$^2$ and 1.3 mg/m$^2$, respectively. See Jagannath, *Br J Haematol.* 127:165-72 (2004). Patient samples and response criteria from patients participating in these studies, as well as the following additional studies described below were sought for use in pharmacogenomic analyses to identify markers associated with patient survival.

An Open-Label Study Comparison of Bortezomib Versus High Dose Dexamethasone in Patients with Relapsed and Refractory Myeloma A multicenter, open-label, randomized study was conducted, comprising 627 enrolled patients with relapsed or refractory multiple myeloma (Protocol M34101-039). See Richardson et. al., *N. Engl. J. Med.,* 352:2487-2498 (2005). Patients were treated with either bortezomib (315 patients) or high-dose dexamethasone (312 patients).

Treatment Dosage and Administration

Drug Supply and Storage

Bortezomib for injection (VELCADE™ Millennium Pharmaceuticals, Inc., Cambridge, Mass.), a sterile lyophilized powder for reconstitution, was supplied in vials containing 2.5 mg bortezomib and 25 mg mannitol USP. Each vial was reconstituted with 2.5 mL of normal (0.9%) saline, Sodium Chloride Injection USP, such that the reconstituted solution contained bortezomib at a concentration of 1 mg/mL. The reconstituted solution was clear and colorless with a final pH between 5 and 6.

Dexamethasome tablets (DECADRON® Merck & Co., Inc.).

TABLE B

| Drug Information | | |
|---|---|---|
| Chemical Name | N-Pyrazinecarbonyl-L-phenylalanine-L-leucineboronic acid | |
| Research Name | MLN341 or PS-341 | |
| Generic Name | Bortezomib | dexamethasone |
| Proprietary Name | VELCADE ™ | Decadron ® |
| CAS Registry No. | 179324-69-7 | 312-93-6 |
| U.S. Pat. No. | 5,780,454 | |
| Classification | Proteasome Inhibitor | Steroid |
| Molecular Formula | $C_{19}H_{25}BN_4O_4$ | $C_{22}H_{29}FO_5$ |
| Molecular Weight | 384.25 | 392.47 |
| Structure | Boronic acid derivative of a leucine phenylalanine dipeptide | Synthetic adrenocorticosteroid |

Patients were assigned to receive bortezomib or high-dose dexamethasone by random allocation at a 1:1 ratio. Randomization was to be stratified, based on the number of lines of prior therapy (one prior line versus more than one prior line of therapy), time of progression relative to treatment (progression while on their most recent therapy or within 6 months of stopping their most recent therapy, or relapse >6 months after receiving their most recent therapy), and screening $\beta_2$-microglobulin levels (>2.5 mg/L versus ≤2.5 mg/L).

Patients assigned to the bortezomib group received treatment for a maximum of 273 days. Patients in this treatment group received up to eight 3-week treatment cycles followed by up to three 5-week treatment cycles of bortezomib.

Within each 3-week treatment cycle, the patient received bortezomib 1.3 mg/m$^2$/dose alone as a bolus intravenous (IV) injection twice weekly for two weeks (on Days 1, 4, 8, and 11) of a 21-day cycle. Within each 5-week treatment cycle, the patient received bortezomib 1.3 mg/m$^2$/dose alone as a bolus IV injection once weekly (on Days 1, 8, 15, and 22) of a 35-day cycle.

Patients assigned to the high-dose dexamethasone group received treatment for a maximum of 280 days. Patients in this treatment group received up to four 5-week treatment cycles, followed by up to five 4-week treatment cycles. Within each 5-week treatment cycle, the patient received dexamethasone 40 mg/day PO, once daily on Days 1 to 4, 9 to 12, and 17 to 20 of a 35-day cycle. Within each 4-week treatment cycle, the patient received dexamethasone 40 mg/day PO once daily on Days 1 to 4 of a 28 day cycle. The protocol provided for patients in the dexamethasone group who experienced confirmed progressive disease (PD) to receive bortezomib on a companion study (An International, Non-Comparative, Open-Label Study of PS-341 Administered to Patients with Multiple Myeloma Who Received High-dose Dexamethasone or Experienced Progressive Disease after Receiving at Least Four Previous Therapies, (Protocol M34101-040). An additional 240 patients who did not participate in this study, enrolled in the companion study and according to the protocol would have received at least four prior therapies. Pharmacogenomic samples were also sought for these 240 patients.

During the study, disease response was assessed according to the European Group for Blood and Marrow Transplant (EBMT) criteria as presented in Table C.

Table C. Disease Response Criteria

TABLE C

| Response | Criteria for response |
|---|---|
| Disease Response Criteria[1] | |
| Complete response (CR)[2] | Requires all of the following: Disappearance of the original monoclonal protein from the blood and urine on at least two determinations for a minimum of six weeks by immunofixation studies. <5% plasma cells in the bone marrow[3]. No increase in the size or number of lytic bone lesions (development of a compression fracture does not exclude response). Disappearance of soft tissue plasmacytomas for at least six weeks. |
| Partial response (PR) | PR includes patients in whom some, but not all, criteria for CR are fulfilled providing the remaining criteria satisfy the requirements for PR. Requires all of the following: ≥50% reduction in the level of serum monoclonal protein for at least two determinations six weeks apart. If present, reduction in 24-hour urinary light chain excretion by either ≥90% or to <200 mg for at least two determinations six weeks apart. ≥50% reduction in the size of soft tissue plasmacytomas (by clinical or radiographic examination) for at least six weeks. No increase in size or number of lytic bone lesions (development of compression fracture does not exclude response). |
| Minimal response (MR) | MR includes patients in whom some, but not all, criteria for PR are fulfilled providing the remaining criteria satisfy the requirements for MR. Requires all of the following: ≥25% to ≤50% reduction in the level of serum monoclonal protein for at least two determinations six weeks apart. If present, a 50 to 89% reduction in 24-hour light chain excretion, which still exceeds 200 mg/24 h, for at least two determinations six weeks apart. 25-49% reduction in the size of plasmacytomas (by clinical or radiographic examination (e.g., 2D MRI, CT scan). No increase in size or number of lytic bone lesions (development of compression fracture does not exclude response). |
| No change (NC) | Not meeting the criteria for MR or PD. |
| Progressive disease (PD) (for patients not in CR) | Requires one or more of the following: >25% increase in the level of serum monoclonal paraprotein, which must also be an absolute increase of at least 5 g/L and confirmed on a repeat investigation one to three weeks later[4,5]. >25% increase in 24-hour urinary light chain excretion, which must also be an absolute increase of at least 200 mg/24 h and confirmed on a repeat investigation one to three weeks later[4,5]. >25% increase in plasma cells in a bone marrow aspirate or on trephine biopsy, which must also be an absolute increase of at least 10%. Definite increase in the size of existing lytic bone lesions or soft tissue plasmacytomas. Development of new bone lesions or soft tissue plasmacytomas (not including compression fracture). Development of hypercalcemia (corrected serum calcium >11.5 mg/dL or 2.8 mmol/L not attributable to any other cause)[4]. |
| Relapse from CR | Requires at least one of the following: Reappearance of serum or urine monoclonal paraprotein on immunofixation or routine electrophoresis to an absolute value of >5 g/L for serum and >200 mg/24 hours for urine, and excluding oligoclonal immune reconstitution. Reappearance of monoclonal paraprotein must be confirmed by at least one follow-up. |

TABLE C-continued

Disease Response Criteria[1]

| Response | Criteria for response |
|---|---|
| | ≥5% plasma cells in the bone marrow aspirate or biopsy. Development of new lytic bone lesions or soft tissue plasmacytomas or definite increase in the size of residual bone lesions (not including compression fracture). Development of hypercalcemia (corrected serum calcium >11.5 mg/dL or 2.8 mmol/L not attributable to any other cause). |

[1]Based on the EBMT criteria. See, Blade J, et al. Br J Haematol; 102(5): 1115-23 (1998).
[2]For proper evaluation of CR, bone marrow should be ≥20% cellular and serum calcium should be within normal limits.
[3]A bone marrow collection and evaluation is required to document CR. Repeat collection and evaluation of bone marrow is not required to confirm CR for patients with secretory myeloma who have a sustained absence of monoclonal protein on immunofixation for a minimum of 6 weeks; however, repeat collection and evaluation of bone marrow is required at the Response Confirmation visit for patients with non-secretory myeloma.
[4]The need for urgent therapy may require repeating these tests earlier or eliminating a repeat examination.
[5]For determination of PD, increase in paraprotein is relative to the nadir.

Patients were evaluable for response if they had received at least one dose of study drug and had measurable disease at baseline (627 total patients: 315 in the bortezomib group and 312 in the dexamethasone group). The evaluation of confirmed response to treatment with bortezomib or dexamethasone according to the European Group for Blood and Marrow Transplant (EBMT) criteria is provided in Table D. Response and date of disease progression was determined by computer algorithm that integrated data from a central laboratory and case report forms from each clinical site, according to the Bladé criteria (Table C). The response rate (complete plus partial response (CR+PR)) in the bortezomib group was 38 percent; and in the dexamethasone group was 18 percent (P<0.0001). Complete response was achieved in 20 patients (6 percent) who received bortezomib, and in 2 patients (<1 percent) who received dexamethasone (P<0.001), with complete response plus near-complete response in 13 and 2 percent (P<0.0001) in patients receiving bortezomib and dexamethasone, respectively. These data have been submitted for publication. See Richardson P G, et al. [submitted NEJM].

Disease progression was determined by Blade criteria as described in Table C and above. The median time to disease progression in the bortezomib group was 6.2 month (189 days); and the in the dexamethasone group was 3.5 months (106 days) (hazard ratio 0.55, P<0.0001). The date of progression was determined by computer algorithm. P-value from log-rank test adjusted by actual randomization factors. See, Richardson et al., New Engl J Med., submitted.

Median time to response was 43 days for patients in both groups. Median duration of response was 8 months in the bortezomib group and 5.6 months in the dexamethasone group.

Patients given bortezomib had a superior overall survival. One-year survival was 80% on bortezomib and 66% on dexamethasone (P<0.0030). This represents a 41% decrease in risk of death in the bortezomib group during the first year after enrollment. The hazard ratio for overall survival was 0.57 (P<0.0013), favoring bortezomib. The analysis of overall survival includes data from 147 patients (44 percent) in the dexamethasone group who had disease progression and subsequently crossed over to receive bortezomib in a companion study.

TABLE D

Summary of Best Confirmed Response to Treatment[1,2] (Population, N = 627)

| Best Confirmed Response | bortezomib n (%) (n = 315) | dexamethasone n (%) (n = 312) | Difference (95% CI)[a] | p-value[b] |
|---|---|---|---|---|
| Overall Response Rate (CR + PR) | 121 (38) | 56 (18) | 0.20 (0.14, 0.27) | <0.0001 |
| Complete Response | 20 (6) | 2 (<1) | 0.06 (0.03, 0.09) | 0.0001 |
| Partial Response | 101 (32) | 54 (17) | 0.15 (0.08, 0.21) | <0.0001 |
| Near CR: IF+ | 21 (7) | 3 (<1) | 0.06 (0.03, 0.09) | |
| SWOG Remission | 46 (15) | 17 (5) | 0.09 (0.05, 0.14) | |
| Minor Response | 25 (8) | 52 (17) | −0.09 (−0.14, −0.04) | |
| CR + PR + MR | 146 (46) | 108 (35) | 0.12 (0.04, 0.19) | |
| No Change | 137 (43) | 149 (48) | −0.04 (−0.12, 0.04) | |
| Progressive Disease | 22 (7) | 41 (13) | −0.06 (−0.11, −0.01) | |
| Not Evaluable | 10 (3) | 14 (4) | −0.01 (−0.04, 0.02) | |

[1]Response based on computer algorithm using the protocol-specified EBMT criteria.
[2]Percents calculated for the statistical output in section 14 are 'rounded' to the nearest integer including percents ≥0.5% but <1% rounding to 1%; these are reported in the in-text tables as <1%.
[a]Asymptotic confidence interval for the difference in response rates.
[b]P-value from the Cochran-Mantel-Haenszel chi-square test adjusted for the actual randomization stratification factors.

Quality of Life assessment can be analyzed to determine if response to therapy was accompanied by measurable improvement in quality of life. Analysis is performed on summary scores as well as individual items, with specific analytical methods outlined in a formal statistical analysis plan developed prior to database lock.

Pharmacogenomic Samples Collected

Pharmacogenomic tumor samples (bone marrow aspirate) were collected from patients for evaluation of the expression of global mRNA levels.

Statistical Procedures

Summary tabulations were presented that displayed the number of observations, mean, standard deviation, median, minimum, and maximum for continuous variables, and the number and percent per category for categorical data. The categories for summarization were the two assigned treatment groups.

For those patients who participated in the pharmacogenomic portion of the study, correlation between RNA expression levels and survival was evaluated.

TABLE E

Summary of Pharmacogenomic Patient Response

| Study | CR | PR | MR | NC | PD | IE | TOTAL with evaluable response |
|---|---|---|---|---|---|---|---|
| All | 10 | 69 | 25 | 59 | 61 | 22 | 246 |
| 024 | 1 | 1 | 0 | 1 | 4 | 0 | 7 |
| 025 | 2 | 10 | 3 | 10 | 14 | 5 | 44 |
| 040 | 1 | 20 | 6 | 13 | 8 | 2 | 50 |
| 039 341 | 5 | 25 | 5 | 19 | 13 | 9 | 76 |
| 039 Dex | 1 | 13 | 11 | 16 | 22 | 6 | 69 |

A total of 264 patient samples were assessed for pharmacogenomic analyses. These patient samples were collected from the clinical trials of bortezomib for the treatment of multiple myeloma (see Table E). The overall response rate to bortezomib in this set of patients was 42.3% (CR+PR rate of 32%). The overall response rate to dexamethasone was 39.7% (CR+PR rate of 22.2%). All pharmacogenomic analyses relied on the European Group for Blood and Marrow Transplant (EBMT) criteria of response category.

Survival information was collected for the studies. Some patients were followed for at least 30 months. For example, the patients in the –039 study were followed for a median of 22 months. Table F provides the number of patients evaluable from each study provided herein. The markers identified in the samples from each patient were studied to identify predictive markers of short or long term survival.

TABLE F

Number of Patients Evaluated for Long-Term Survival

| Study | Patients evaluable for survival |
|---|---|
| -024 | 7 |
| -025 | 44 |
| -040 | 57 |
| -039 Bortezomib | 80 |
| Bortez-pool of all studies | 188 |
| -039 Dexamethasone | 76 |
| TOTAL | 264 |

The level of expression of predictive markers in any bortezomib study alone, or in combination, can be used to develop classifiers for prediction of short or long term survival after proteasome inhibition therapy, using statistical methods known in the art. The level of expression of markers in the –039 dexamethasone study can be used to develop classifiers for short or long term survival after glucocorticoid therapy.

Identification of Short Term and Long Term Survival Predictive Markers

Biopsies from 264 multiple myeloma patients with survival information resulted in generation of high quality gene expression data which was used to identify predictive markers. Candidate markers that are associated with the survival of multiple myeloma patients receiving proteasome inhibition (e.g., bortezomib) therapy or glucocorticoid (e.g., dexamethasone) therapy were selected by using Cox proportional hazards modeling.

Upon collection of patient bone marrow aspirate, the myeloma cells were enriched via rapid negative selection (FIG. 1A). The enrichment procedure employs a cocktail of cell-type specific antibodies coupled with an antibody that binds red blood cells RosetteSep (Stem Cell Technologies). The antibody cocktail has antibodies with the following specificity: CD14 (monocytes), CD2 (T and NK cells), CD33 (myeloid progenitors and monocytes), CD41 (platelets and megakaryocytes), CD45RA (naïve B and T cells) and CD66b (granulocytes). The antibodies cross-linked the non-myeloma cell types to the red blood cells in the samples. The bound cell types were removed using a modified ficoll density gradient. Myeloma cells were then collected and frozen. In the international studies, the first two samples from each site were collected and subjected to RNA isolation so that feedback on quantity and quality could be provided; ultimately Phase 2 and 3 trials provided a similar percentage of informative samples. Control bone marrow plasma cell samples were obtained from normal donors (AllCells, Berkeley Calif.).

Total RNA was isolated using a QIAGEN® Group RNEASY® isolation kit (Valencia, Calif.) and quantified by spectrophotometry. 2.0 µg of RNA (if available) was converted to biotinylated cRNA by a standard T7 based amplification protocol (AFFYMETRIX® Inc., Santa Clara, Calif.). A small number of samples with ≥0.5-2.0 µg were also labeled and subsequently hybridized if 6 µg of cRNA was produced. Samples from clinical trials 025 and 040 were randomized by clinical site and operator, assigned to batches of 24 samples and labeled by manual T7 amplification (Batch1). Samples from clinical trial 039 were randomized by clinical site and assigned to 95 sample batches and labeled by an automated T7 amplification procedure (Batch 2). For the automated T7 amplification procedure the cDNA and the biotin labeled cRNA were purified using AMPURE® PCR Purification System, following the manufacturer's protocol (AGENCOURT® Bioscience Corporation, Beverly, Mass.). The cRNA yield was assessed by spectrophotometry and 10 µg of cRNA was fragmented and further processed for triplicate hybridization on the AFFYMETRIX® Human Genome HG-U133A and HG-U133B GENECHIP® arrays. In cases where cRNA yield ranged between 6 µg to 10 µg, the entire cRNA sample was fragmented.

cRNA for each sample was hybridized to the U133A/B arrays in triplicate; operators, chip lots, clinical sites and scanners (GENECHIP® Scanner 3000) were controlled throughout. Background subtraction, smoothing adjustment, noise corrections, and signal calculations were performed with AFFYMETRIX® MAS5.0. Quality control metrics determined by AFFYMETRIX® analysis and MPI included:

percent present call (>25) scale factor (<11), β-actin 3':5' ratio (<15) and background (<120). Samples that fell outside these metrics were excluded from subsequent analysis.

Figure 1B:
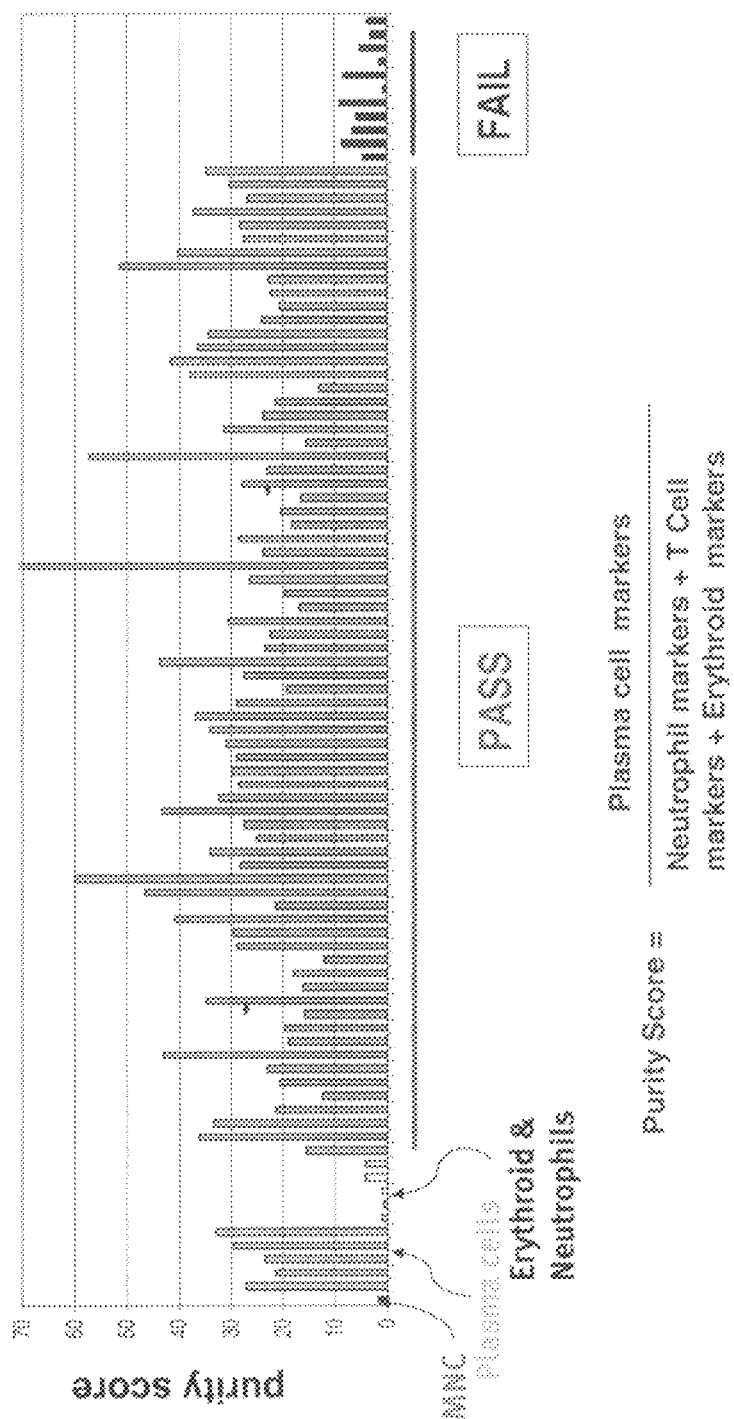

The myeloma purity score examines expression of genes known in the literature to be expressed highly in myeloma cells (and their normal plasma precursor cells), to expression of genes known to be expressed highly in erythroid cells, neutrophils and T cells—see list of 14 markers below). The myeloma score=expression of myeloma markers (#1-4 below)/erythroid (#5-7)+neutrophil (#8-11)+T cell (#12-14 below):
1. 205692_s_at CD38 CD38 antigen (p45) myeloma/plasma cell
2. 201286_at SDC1 syndecan-1 myeloma/plasma cell
3. 201891_s_at B2M beta-2 microglobulin myeloma/plasma cell
4. 211528_x_at B2M beta-2 microglobulin myeloma/plasma cell
5. 37986_at EpoR erythropoetin receptor erythroid cell
6. 209962_at EpoR erythropoetin receptor erythroid cell
7. 205838_at GYPA glycophorinA erythroid cell
8. 203948_s_at MPO myeloperoxidase neutrophil
9. 203591_s_at CSFR3colony stimulating factor 3receptor (granulocyte) neutrophil
10. 204039_at CEBPACCAAT/enhancer binding protein (C/EBP), alpha neutrophil
11. 214523_at CEBPECCAAT/enhancer binding protein (C/EBP), epsilon neutrophil
12. 209603_at GATA3 GATA binding protein 3 T lymphocyte
13. 209604_s_at GATA4 GATA binding protein 4 T lymphocyte
14. 205456_at CD3ECD3E antigen, epsilon polypeptide T lymphocyte Myeloma purity scores of representative samples are illustrated in FIG. 1B. Samples with a myeloma purity score less than 10 were excluded from further analysis.

Normalization and Logarithmic Transformation.

Expression values for all markers on each microarray were normalized to a trimmed mean of 150. Expression values were determined using MAS5 gene expression analysis data processing software (AFFYMETRIX® Inc., Santa Clara, Calif.). These values will be referred to as the "normalized expression" in the remainder of this section. In a further processing step, the median expression level was determined across repeated expression measurements for the same sample. The median expression level values for the markers are being submitted to the Gene Expression Omnibus (GEO) program, a gene expression/molecular abundance repository, at the National Center for Biotechnology Information (NCBI, Bethesda, Md.) and will be searchable and retrievable at the NCBI website. These median expression level values are incorporated herein by reference. The logarithm base 2 was taken of the resulting median expression level, and this value will be referred to as the "log expression" in the remainder of this section.

Variance Components Analysis.

There were up to six replicate hybridizations for each patient: three replicate hybridizations for each of two T7 RNA labelings. To identify within-patient and between-patient expression variance for each probe set, a mixed effects linear model was used. For each probe set, a model was fit which included the patient specific random effect representing the deviation from the overall mean intensity, and the replicate hybridization random effect. These random effects are referred to as the variance components of the model. Model fitting includes assessing the variance due to these two random effects, resulting in estimates of between-patient sample variance and replicate, or within-patient variance.

Removal of Genes with Low Inter-Patient Variance.

The probe sets were reduced in number to include only those having more than 65% of their variance due to patient sample variance. Of 44,928 probe sets, 9,200 passed this filter and were carried on to further analysis.

Single Marker Selection.

Single gene transcripts that are associated with patient survival can be identified using the survival analysis methodology described below. Predictive markers identified using the methodology described herein are set forth in Table 1 and Table 2. Table 1 markers were identified using bortezomib-treated patients across studies 025, 039 and 040. Table 2 markers were identified using patients in studies 025 and 040, and were used to predict survival outcome in 039, as shown in FIG. 3 and described below.

Model Selection.

A set of one or more gene transcripts that together classify samples into short term and long term survivors, in the context of a particular classifier algorithm, is referred to as a "model." The gene transcripts are referred to as "features." Determining which combination of gene transcript(s) best classifies samples into sensitive and resistant groups is referred to as "model selection." The following section describes the process of how the models of the present invention were identified. The methods provided herein along with the single marker identification or predictive markers can be used to identify additional models comprising markers of the invention. There are many other classification methods for building models to classify samples based on their features, which can be used with the markers in Table 1 or 2 to build predictive models. For example, predictors are based on linear combinations of the expression values (Golub et al., Science, 286:531-7 (1999), Radmacher et al. J. Comput. Biol., 9:505-12 (2002)). Other predictors are based on neural networks, which can be used to predict survival time directly or to develop reduced dimensionality representations of the expression data which can then be fed into a Cox proportional hazards model (Khan et al., Nat. Med. 7:673-9 (2001), Nguyen et al., *Bioinformatics* 18:39-50 (2002), Lundina et al., Oncology 57:281-286 (1999)). There are many other methods for defining a multivariate predictor, all of which can be adapted to use with survival data (Ripley B D. Pattern recognition and neural networks (Cambridge (U.K.): Cambridge University Press; (1996), Dudoit et al., J Am. Stat. Assoc. 97:77-87 (2002)). These can be used for survival by threshold the survival time to turn it into a classification problem (low- and high-risk)

Feature Ranking and Filtering

The first step in predictive model selection is to filter the 9,200 features down to a smaller number which show a correspondence with the sample classifications. Filtering involves first ranking the features by a scoring method, and then taking only the highest ranking features for further analysis. The filtering algorithm used in the present invention was Cox proportional hazards modeling to determine a p-value for the association of a feature with time to progression and death.

A Cox proportional hazard analysis was performed to determine predictors of time until death in patients with relapsed and refractory multiple myeloma after treatment. This methodology is designed to analyze time to event data where some of the data may be censored (see E. T. Lee, Statistical Methods for Survival Data Analysis, $2^{nd}$ ed. 1992, John Wiley & Sons, Inc.).

We estimated Cox proportional hazard models for each of the 9200 transcripts passing the variance filter. That is, 9200 models were estimated where each model contained 1 transcript. From each model, we obtained estimates of relative risk, 95% confidence intervals and p-values for the association of each transcript to survival. From the 9200 models, we found several transcripts which had p-values of less than 0.01 in analyzing the patients analyzed. These transcripts were significantly associated with survival. These probe sets are listed in Table 1 (analysis of samples from 188 patients) and Table 2 (analysis of samples from 101 patients).

Table 1 is ordered by the hazard ratio from the Cox proportional hazards model built on all Velcade-treated samples in the dataset, using the given probe set. High expression levels of the markers at the beginning of the table are most strongly associated with shorter survival; high expression levels of the markers at the end of the table are most strongly associated with longer survival.

Specific Application of Class Prediction

The method of Bair and Tibshirani (2004) PLoS Biol. 2(4), E108: 0511-0522) was used to illustrate how to combine expression data from probesets associated with survival outcome into a predictive model. Principle components of the expression data for the probe sets most closely associated with survival are computed. We illustrate the method with the 100 probe sets with lowest p-values from the single-gene analysis; other numbers of genes are also predictive. A Cox proportional hazards model is then built on the expression data mapped into the space defined by the principle components. To test whether the model has predictive value, the dataset was applied to a test set; the principle components were computed only using the training set, and applied to the test set. The p-value of the Cox proportional hazards model built on the transformed test data indicates whether the selected genes have predictive value. Using the linear predictor from the Cox model, patients can be divided into low- and high-risk groups. A log-rank test is applied to the outcome data of these groups of patients to determine whether the difference between the predicted high- and low-risk groups is significant.

Exemplification of Model Selection for Table 2

A classifier was developed from analysis of the level of expression of the markers in the –025 and the –040 studies using the Principal Components algorithm. The expression levels in samples from these studies were combined to build a model using the 100 probesets with strongest superpc scores listed in column 2 of Table 2. This set of probes (Table 2; "survival classifier") was applied as a training set to the –039 studies.

Figure 3A:
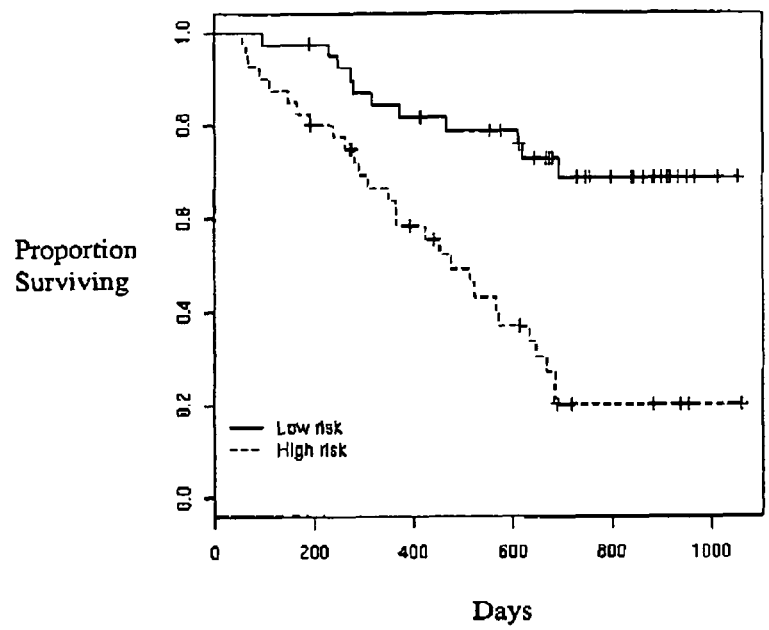
FIG. 3 provides prediction of survival using Super PC. An 025+040 based survival classifier was used to identify short term and long term survival risk groups within an independent test dataset derived from trial 039 patients. Kaplan-Meir analyses of the actual survival of these predicted short term/long term risk patient groups is shown for test set (A) the 039 bortezomib arm patients, P=0.00006; (B) the 039 dexamethasone arm patients, P=0.0001; (C) the ISS stage 1 patients from 039 (bortez+dex), P=0.01; (D) the ISS stage 2 or 3 patients from 039 (bortez+dex), P=0.00002.
Figure 3B:
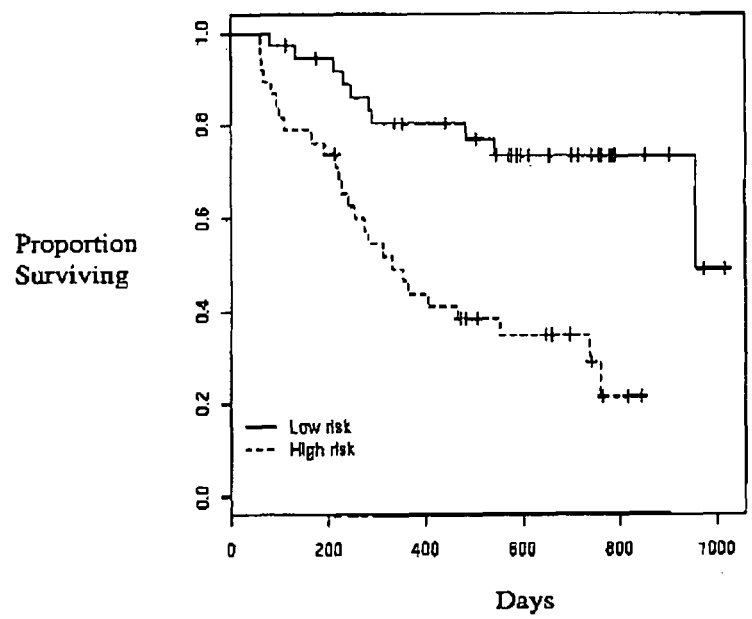

Cox models were significant in both 039V and 039D, though more significant in 039V (p=0.00000437 vs p=0.00119). The survival classifier exemplified in Table 2 stratified the 039 bortezomib patients into high and low risk groups which were significantly associated with their risk of death (P<0.000004, FIG. 3). In FIGS. 3A and B, the models are visualized by dividing the test samples into two equally sized sets representing long term and short term survivors.

Effect of Varying the Model Size

In this round of analysis, only the first principal component (PC) of the training gene data were used, and test samples were classified into two roughly equal groups based on the projection of their gene data onto that PC vector. A log rank test determines whether those two groups have different survival risk.

TABLE G

Varying Probeset Number
Survival models built on 025 + 040

| Threshold | # probesets | LR p-value on 039V | LR p-value on 039D |
|---|---|---|---|
| 1 | 2025 | 0.00297 | 0.0188 |
| 1.1 | 1656 | 0.000517 | 0.0135 |
| 1.2 | 1343 | 0.000517 | 0.0135 |
| 1.3 | 1082 | 0.000916 | 0.00694 |
| 1.4 | 841 | 0.000217 | 0.00694 |
| 1.5 | 647 | 0.000633 | 0.0103 |
| 1.6 | 496 | 0.000332 | 0.0103 |
| 1.7 | 390 | 0.00226 | 0.012 |
| 1.8 | 311 | 0.00443 | 0.012 |
| 1.9 | 242 | 0.00186 | 0.012 |
| 2 | 191 | 0.000329 | 0.012 |
| 2.1 | 145 | 0.000527 | 0.012 |
| 2.2 | 115 | 0.0011 | 0.0203 |
| 2.3 | 95 | 0.000447 | 0.0348 |
| 2.4 | 72 | 0.000952 | 0.0306 |
| 2.5 | 53 | 0.000952 | 0.0306 |
| 2.6 | 37 | 0.00107 | 0.0176 |
| 2.7 | 23 | 0.000497 | 0.0216 |
| 2.8 | 16 | 0.00458 | 0.00125 |
| 2.9 | 8 | 0.000847 | 0.0132 |
| 3 | 3 | 0.0507 | 0.0289 |

The above Table G summarizes the number of probesets included in the 025+040 model as the threshold on superpc score was varied. The ability to distinguish long term survivors from short term survivors was retained throughout near all (but the smallest) models. Assignments were determined to be quite stable: most samples are assigned to the same class (long term survivor or short term survivor) regardless of the number of probesets included in the model.

Summary of the Data Provided in the Tables

The following terms are used throughout the Tables:

"No." or "Number" corresponds to an identification number for the predictive markers.

"Probeset ID" corresponds to the AFFYMETRIX® Inc. (Santa Clara, Calif.) identifier from the Human Genome U133A, B set oligonucleotide arrays which were used;

"Rep Public ID" refers to a Representative Public identifier for the gene corresponding to the probe set, and was taken from HG-U133A and HG-U133B annotation files, dated Apr. 12, 2005, which was available and downloaded from the Human Genome U133 GENECHIP® array support area of the AFFYMETRDX® Inc. web site (support/technical/byproduct.affx?product=hgu 133);

"Title" corresponds to a common description, where available, and was also taken from the AFFYMETRIX® Inc. annotation files;

"Gene symbol" corresponds to a symbol the gene is commonly known by, and was also taken from the AFFYMETRIX® Inc. annotation files;

"Entrez Gene ID" corresponds to a NCBI Unigene unique gene identifier (Entrez Gene database, gene-specific information; National Center for Biotechnology Information, Bethesda, Md.), of a gene recognized by the probeset, as annotated by AFFYMETRIX® Inc. and was taken from HG-U133A and HG-U133B annotation files, Release 20, dated Jul. 17, 2006, which was publicly available and downloaded from the Human Genome U133 Set technical support documentation on the AFFYMETRIX® Inc. web site (support/technical/byproduct.affx?product=hgu 133);

"TTP Marker" or "TTP" represents indication of predictive marker which is significantly upregulated in samples with a correlation to longer time to progression (+), or are significantly upregulated in samples with a correlation to shorter time to progression (−). The "V" represents bortezomib and "D" represents dexamethasone. A "+" represents good prognosis for time to progression, a "−" represents a poor prognosis for time to progression;

"Response Marker" or "Resp" represents indication of predictive marker which is significantly upregulated in samples which are responsive to therapy (+), or are significantly upregulated in samples which are non-responsive to therapy (−). The "V" represents bortezomib and "D" represents dexamethasone. A "+" represents responsive, a "−" represents non responsive.

"Super PC 025+040" represents the superPC score for each probeset upon analysis of expression levels in samples from the 025 and 040 studies. Probesets with positive values are associated with shorter survival time and probesets with negative values are associated with longer survival time.

Predictive markers of the invention are provided in Tables 1 and 2. Table 1 sets forth predictive markers identified which are specific identifiers of long term and short term survival. Marker nos. 225 to 403 in Table 1 are upregulated in long term survivors; marker nos. 1 to 224 are upregulated in short term survivors. Table 1 also indicates markers which are correlated with time to progression or response to a treatment (see, International Patent Publication No. WO04053066, published Jun. 24, 2004, or U.S. patent application Ser. No. 11/449,195, filed Jun. 8, 2006). Table 2 also sets forth predictive markers identified which are specific identifiers of long term or short term survival. Marker nos. 38 to 100 in Table 2 are upregulated in long term survivors; marker nos. 1 to 37 in Table 2 are upregulated in short term survivors.

Among the predictive markers identified in Table 1 and Table 2, are a subset of markers which correspond to genes whose putative biological function or functions are particularly interesting, including function(s) particularly relevant to the use of proteasome inhibitors for the treatment of cancers, including myeloma. Some of the genes are known to be involved in the initiation or progression of myeloma, the growth, survival or signaling of lymphoid cells, the regulation of drug metabolism or apoptotic pathways or encode components of the ubiquitin/proteasome pathway that is directly targeted by proteasome inhibitors. Table H below lists the categories and functions and provides the key to understanding the "Biol. Cat." column in the Tables.

TABLE H

Biological categories for Annotating the Markers in Tables 1 and 2

| Biological Category | Code |
|---|---|
| Myeloma Translocation | A |
| Oncogene | B |
| Tumor Suppressor Pathway | C |
| Cancer Antigen | D |
| NF-κB Pathway | E |
| Hematopoiesis | F |
| Apoptotic Signaling | G |
| Myeloma Signaling | H |
| Mitogenic Signaling | I |
| Protein Homeostasis | J |
| Oncogenic Signaling | K |
| Adhesion | L |
| Cell Cycle | M |
| Drug Metabolism | N |
| Drug Resistance | O |
| Ubiquitin/proteasome Pathway | P |
| Stem Cell | Q |
| Mitochondria Function | R |
| Rapamycin Regulated | S |
| Expressed in Lymphoma (DLBCL) | T |
| Expressed in Proliferative Breast Cancer | U |
| Expressed in Renal Cancer | V |
| RNA Processing | W |

TABLE 1

Short Term and Long Term Survival Markers

| No | Probe Set ID | Chip | Rep Pub ID | Title |
|---|---|---|---|---|
| 1 | 209852_x_at | HG-U133A | | |
| 2 | 201726_at | HG-U133A | BC003376 | ELAV (embryonic lethal, abnormal vision, *Drosophila*)-like 1 (Hu antigen R) |
| 3 | 202244_at | HG-U133A | NM_002796 | proteasome (prosome, macropain) subunit, beta type, 4 |
| 4 | 202469_s_at | HG-U133A | AU149367 | cleavage and polyadenylation specific factor 6, 68 kDa |
| 5 | 211946_s_at | HG-U133A | AL096857 | BAT2 domain containing 1 |
| 6 | 220642_x_at | HG-U133A | NM_016334 | G protein-coupled receptor 89 |
| 7 | 203344_s_at | HG-U133A | NM_002894 | retinoblastoma binding protein 8 |
| 8 | 208114_s_at | HG-U133A | | |
| 9 | 212742_at | HG-U133A | | |
| 10 | 209644_x_at | HG-U133A | U38945 | cyclin-dependent kinase inhibitor 2A (melanoma, p16, inhibits CDK4) |
| 11 | 232219_x_at | HG-U133B | | |
| 12 | 225463_x_at | HG-U133B | BF941168 | G protein-coupled receptor 89 |

TABLE 1-continued

| | | | Short Term and Long Term Survival Markers | |
|---|---|---|---|---|
| 13 | 222140_s_at | HG-U133A | AK021758 | G protein-coupled receptor 89 |
| 14 | 208758_at | HG-U133A | D89976 | 5-aminoimidazole-4-carboxamide ribonucleotide formyltransferase/IMP cyclohydrolase |
| 15 | 226434_at | HG-U133B | BF000655 | hypothetical protein MGC22793 |
| 16 | 202824_s_at | HG-U133A | NM_005648 | transcription elongation factor B (SIII), polypeptide 1 (15 kDa, elongin C) |
| 17 | 223531_x_at | HG-U133B | AF151035 | G protein-coupled receptor 89 |
| 18 | 201966_at | HG-U133A | NM_004550 | NADH dehydrogenase (ubiquinone) Fe—S protein 2, 49 kDa (NADH-coenzyme Q reductase) |
| 19 | 201771_at | HG-U133A | NM_005698 | secretory carrier membrane protein 3 |
| 20 | 220607_x_at | HG-U133A | NM_016397 | TH1-like (*Drosophila*) |
| 21 | 218016_s_at | HG-U133A | | |
| 22 | 208694_at | HG-U133A | U47077 | protein kinase, DNA-activated, catalytic polypeptide |
| 23 | 200057_s_at | HG-U133B | NM_007363 | non-POU domain containing, octamer-binding |
| 24 | 226177_at | HG-U133B | AI052020 | glycolipid transfer protein |
| 25 | 218336_at | HG-U133A | NM_012394 | prefoldin 2 |
| 26 | 209814_at | HG-U133A | | |
| 27 | 208972_s_at | HG-U133A | AL080089 | ATP synthase, H+ transporting, mitochondrial F0 complex, subunit c (subunit 9), isoform 1 |
| 28 | 221761_at | HG-U133A | | |
| 29 | 225291_at | HG-U133B | AI967971 | polyribonucleotide nucleotidyltransferase 1 |
| 30 | 209523_at | HG-U133A | | |
| 31 | 201872_s_at | HG-U133A | AI002002 | ATP-binding cassette, sub-family E (OABP), member 1 |
| 32 | 209609_s_at | HG-U133A | BC004517 | mitochondrial ribosomal protein L9 |
| 33 | 206656_s_at | HG-U133A | BC000353 | chromosome 20 open reading frame 3 |
| 34 | 210131_x_at | HG-U133A | D49737 | |
| 35 | 224632_at | HG-U133B | BE794289 | G patch domain containing 4 |
| 36 | 201612_at | HG-U133A | | |
| 37 | 210543_s_at | HG-U133A | U34994 | protein kinase, DNA-activated, catalytic polypeptide |
| 38 | 225006_x_at | HG-U133B | AJ238379 | TH1-like (*Drosophila*) |
| 39 | 214526_x_at | HG-U133A | NM_005394 | |
| 40 | 217835_x_at | HG-U133A | NM_018840 | chromosome 20 open reading frame 24 |
| 41 | 201157_s_at | HG-U133A | AF020500 | N-myristoyltransferase 1 |
| 42 | 225204_at | HG-U133B | AA521311 | T-cell activation protein phosphatase 2C |
| 43 | 208833_s_at | HG-U133A | AF119662 | ataxin 10 |
| 44 | 218389_s_at | HG-U133A | NM_016022 | anterior pharynx defective 1 homolog A (*C. elegans*) |
| 45 | 219960_s_at | HG-U133A | | |
| 46 | 201652_at | HG-U133A | NM_006837 | COP9 constitutive photomorphogenic homolog subunit 5 (*Arabidopsis*) |
| 47 | 202004_x_at | HG-U133A | NM_003001 | succinate dehydrogenase complex, subunit C, integral membrane protein, 15 kDa |
| 48 | 201068_s_at | HG-U133A | NM_002803 | proteasome (prosome, macropain) 26S subunit, ATPase, 2 |
| 49 | 209044_x_at | HG-U133A | | |
| 50 | 215088_s_at | HG-U133A | | |
| 51 | 218566_s_at | HG-U133A | | |
| 52 | 201754_at | HG-U133A | NM_004374 | cytochrome c oxidase subunit VIc |
| 53 | 208775_at | HG-U133A | D89729 | exportin 1 (CRM1 homolog, yeast) |
| 54 | 226883_at | HG-U133B | | |

TABLE 1-continued

| | | Short Term and Long Term Survival Markers | | |
|---|---|---|---|---|
| 55 | 218270_at | HG-U133A | NM_024540 | mitochondrial ribosomal protein L24 |
| 56 | 222610_s_at | HG-U133B | | |
| 57 | 203033_x_at | HG-U133A | NM_000143 | fumarate hydratase |
| 58 | 201144_s_at | HG-U133A | NM_004094 | eukaryotic translation initiation factor 2, subunit 1 alpha, 35 kDa |
| 59 | 225865_x_at | HG-U133B | AJ238374 | TH1-like (*Drosophila*) |
| 60 | 218605_at | HG-U133A | NM_022366 | transcription factor B2, mitochondrial |
| 61 | 207614_s_at | HG-U133A | NM_003592 | cullin 1 |
| 62 | 200600_at | HG-U133A | NM_002444 | moesin |
| 63 | 208644_at | HG-U133A | M32721 | poly (ADP-ribose) polymerase family, member 1 |
| 64 | 221020_s_at | HG-U133A | NM_030780 | mitochondrial folate transporter/carrier |
| 65 | 210386_s_at | HG-U133A | BC001906 | metaxin 1 |
| 66 | 200975_at | HG-U133A | NM_000310 | palmitoyl-protein thioesterase 1 (ceroid-lipofuscinosis, neuronal 1, infantile) |
| 67 | 201128_s_at | HG-U133A | NM_001096 | ATP citrate lyase |
| 68 | 200882_s_at | HG-U133A | NM_002810 | proteasome (prosome, macropain) 26S subunit, non-ATPase, 4 |
| 69 | 202272_s_at | HG-U133A | | |
| 70 | 212279_at | HG-U133A | BE779865 | hypothetical protein MAC30 |
| 71 | 212502_at | HG-U133A | AV713053 | chromosome 10 open reading frame 22 |
| 72 | 226116_at | HG-U133B | | |
| 73 | 201275_at | HG-U133A | NM_002004 | farnesyl diphosphate synthase (farnesyl pyrophosphate synthetase, dimethylallyltranstransferase, geranyltranstransferase) |
| 74 | 213893_x_at | HG-U133A | AA161026 | postmeiotic segregation increased 2-like 5 |
| 75 | 218156_s_at | HG-U133A | | |
| 76 | 219933_at | HG-U133A | NM_016066 | glutaredoxin 2 |
| 77 | 222654_at | HG-U133B | AI302253 | myo-inositol monophosphatase A3 |
| 78 | 203800_s_at | HG-U133A | BG254653 | mitochondrial ribosomal protein S14 |
| 79 | 201786_s_at | HG-U133A | NM_001111 | adenosine deaminase, RNA-specific |
| 80 | 218984_at | HG-U133A | NM_019042 | hypothetical protein FLJ20485 |
| 81 | 201381_x_at | HG-U133A | AF057356 | calcyclin binding protein |
| 82 | 208822_s_at | HG-U133A | U18321 | death associated protein 3 |
| 83 | 212371_at | HG-U133A | AL049397 | CGI-146 protein |
| 84 | 225261_x_at | HG-U133B | AJ238376 | TH1-like (*Drosophila*) |
| 85 | 202613_at | HG-U133A | | |
| 86 | 225676_s_at | HG-U133B | BE409290 | DKFZP564O0463 protein |
| 87 | 226219_at | HG-U133B | AW575123 | hypothetical protein LOC257106 |
| 88 | 222622_at | HG-U133B | | |
| 89 | 223040_at | HG-U133B | BC005181 | N-acetyltransferase 5 (ARD1 homolog, *S. cerevisiae*) |
| 90 | 223114_at | HG-U133B | | |
| 91 | 218167_at | HG-U133A | NM_016627 | hypothetical protein LOC51321 |
| 92 | 226073_at | HG-U133B | BE857362 | hypothetical protein LOC219854 |
| 93 | 224593_at | HG-U133B | BE965646 | zinc finger protein ZFOC1 |
| 94 | 230618_s_at | HG-U133B | BF110903 | |
| 95 | 224743_at | HG-U133B | BF674724 | myo-inositol monophosphatase A3 |
| 96 | 218151_x_at | HG-U133A | NM_024531 | G protein-coupled receptor 172A |
| 97 | 218592_s_at | HG-U133A | NM_017829 | cat eye syndrome chromosome region, candidate 5 |
| 98 | 222212_s_at | HG-U133A | AK001105 | LAG1 longevity assurance homolog 2 (*S. cerevisiae*) |
| 99 | 224523_s_at | HG-U133B | BC006475 | hypothetical protein MGC4308 |
| 100 | 214170_x_at | HG-U133A | AA669797 | fumarate hydratase |

TABLE 1-continued

Short Term and Long Term Survival Markers

| | | | | |
|---|---|---|---|---|
| 101 | 218774_at | HG-U133A | NM_014026 | decapping enzyme, scavenger |
| 102 | 218401_s_at | HG-U133A | NM_012482 | zinc finger protein 281 |
| 103 | 222443_s_at | HG-U133B | AF182415 | RNA binding motif protein 8A |
| 104 | 212296_at | HG-U133A | NM_005805 | Transmembrane anchor protein 1 |
| 105 | 201520_s_at | HG-U133A | BF034561 | G-rich RNA sequence binding factor 1 |
| 106 | 225317_at | HG-U133B | AL574669 | acyl-Coenzyme A binding domain containing 6 |
| 107 | 217900_at | HG-U133A | NM_018060 | mitochondrial isoleucine tRNA synthetase |
| 108 | 202282_at | HG-U133A | NM_004493 | hydroxyacyl-Coenzyme A dehydrogenase, type II |
| 109 | 215171_s_at | HG-U133A | AK023063 | translocase of inner mitochondrial membrane 17 homolog A (yeast) |
| 110 | 202243_s_at | HG-U133A | NM_002796 | proteasome (prosome, macropain) subunit, beta type, 4 |
| 111 | 57082_at | HG-U133A | AA169780 | LDL receptor adaptor protein |
| 112 | 225881_at | HG-U133B | AL513639 | solute carrier family 35, member B4 |
| 113 | 224634_at | HG-U133B | AI911518 | G patch domain containing 4 |
| 114 | 200090_at | HG-U133B | BG168896 | farnesyltransferase, CAAX box, alpha |
| 115 | 228357_at | HG-U133B | | |
| 116 | 212160_at | HG-U133A | AI984005 | exportin, tRNA (nuclear export receptor for tRNAs) |
| 117 | 201066_at | HG-U133A | NM_001916 | cytochrome c-1 |
| 118 | 208805_at | HG-U133A | BC002979 | proteasome (prosome, macropain) subunit, alpha type, 6 |
| 119 | 209186_at | HG-U133A | M23114 | ATPase, Ca++ transporting, cardiac muscle, slow twitch 2 |
| 120 | 200910_at | HG-U133A | NM_005998 | chaperonin containing TCP1, subunit 3 (gamma) |
| 121 | 212282_at | HG-U133A | BF038366 | hypothetical protein MAC30 |
| 122 | 218728_s_at | HG-U133A | | |
| 123 | 225479_at | HG-U133B | AL524175 | CDNA FLJ32247 fis, clone PROST1000120 |
| 124 | 202642_s_at | HG-U133A | NM_003496 | transformation/transcription domain-associated protein |
| 125 | 211609_x_at | HG-U133A | U51007 | proteasome (prosome, macropain) 26S subunit, non-ATPase, 4 |
| 126 | 213189_at | HG-U133A | BE66695 | MYC induced nuclear antigen |
| 127 | 202715_at | HG-U133A | NM_004341 | carbamoyl-phosphate synthetase 2, aspartate transcarbamylase, and dihydroorotase |
| 128 | 225153_at | HG-U133B | AI814295 | G elongation factor, mitochondrial 1 |
| 129 | 209093_s_at | HG-U133A | | |
| 130 | 228095_at | HG-U133B | AA608749 | |
| 131 | 209218_at | HG-U133A | AF098865 | squalene epoxidase |
| 132 | 212449_s_at | HG-U133A | BG288007 | lysophospholipase I |
| 133 | 209187_at | HG-U133A | AW516932 | down-regulator of transcription 1, TBP-binding (negative cofactor 2) |
| 134 | 230257_s_at | HG-U133B | | |
| 135 | 222619_at | HG-U133B | AU150752 | Zinc finger protein 281 |
| 136 | 225213_at | HG-U133B | AW300598 | T-cell activation protein phosphatase 2C |
| 137 | 227212_s_at | HG-U133B | | |
| 138 | 222646_s_at | HG-U133A | AW268365 | ERO1-like (*S. cerevisiae*) |
| 139 | 212316_at | HG-U133A | AA502912 | nucleoporin 210 kDa |
| 140 | 222155_s_at | HG-U133A | AK021918 | G protein-coupled receptor 172A |
| 141 | 212281_s_at | HG-U133A | BF038366 | hypothetical protein MAC30 |
| 142 | 207622_s_at | HG-U133A | | |
| 143 | 226740_x_at | HG-U133B | BF740216 | hypothetical protein DJ328E19.C1.1 /// hypothetical protein LOC200030 /// hypothetical |

TABLE 1-continued

Short Term and Long Term Survival Markers

| | | | | |
|---|---|---|---|---|
| | | | | protein MGC8902 /// hypothetical gene supported by AB051480; NM_017940 /// AG1 protein |
| 144 | 218812_s_at | HG-U133A | NM_025156 | chromosome 7 open reading frame 19 |
| 145 | 205367_at | HG-U133A | NM_020979 | adaptor protein with pleckstrin homology and src homology 2 domains |
| 146 | 225253_s_at | HG-U133B | AI632244 | methyltransferase like 2 /// hypothetical protein FLJ12760 |
| 147 | 205214_at | HG-U133A | | |
| 148 | 211098_x_at | HG-U133A | AF277194 | putative membrane protein |
| 149 | 222477_s_at | HG-U133B | BC005176 | transmembrane 7 superfamily member 3 |
| 150 | 225401_at | HG-U133B | BF977145 | kidney predominant protein NCU-G1 |
| 151 | 201821_s_at | HG-U133A | BC004439 | translocase of inner mitochondrial membrane 17 homolog A (yeast) |
| 152 | 218237_s_at | HG-U133A | NM_030674 | solute carrier family 38, member 1 |
| 153 | 225399_at | HG-U133B | AF288394 | chromosome 1 open reading frame 19 |
| 154 | 223244_s_at | HG-U133B | AF217092 | 13 kDa differentiation-associated protein |
| 155 | 209435_s_at | HG-U133A | BC000265 | rho/rac guanine nucleotide exchange factor (GEF) 2 |
| 156 | 201764_at | HG-U133A | NM_024056 | hypothetical protein MGC5576 |
| 157 | 201897_s_at | HG-U133A | NM_001826 | CDC28 protein kinase regulatory subunit 1B |
| 158 | 210243_s_at | HG-U133A | AF038661 | UDP-Gal:betaGlcNAc beta 1,4-galactosyltransferase, polypeptide 3 |
| 159 | 218058_at | HG-U133A | NM_014593 | CXXC finger 1 (PHD domain) |
| 160 | 203258_at | HG-U133A | NM_006442 | DR1-associated protein 1 (negative cofactor 2 alpha) |
| 161 | 200742_s_at | HG-U133A | BG231932 | tripeptidyl peptidase I |
| 162 | 209340_at | HG-U133A | S73498 | UDP-N-acteylglucosamine pyrophosphorylase 1 |
| 163 | 213947_s_at | HG-U133A | AI867102 | nucleoporin 210 kDa |
| 164 | 231715_s_at | HG-U133B | NM_013328 | pyrroline-5-carboxylate reductase family, member 2 |
| 165 | 202605_at | HG-U133A | NM_000181 | glucuronidase, beta |
| 166 | 227558_at | HG-U133B | AI570531 | chromobox homolog 4 (Pc class homolog, *Drosophila*) |
| 167 | 222997_s_at | HG-U133B | BC004566 | mitochondrial ribosomal protein S21 |
| 168 | 227985_at | HG-U133B | AI928513 | |
| 169 | 208966_x_at | HG-U133A | AF208043 | interferon, gamma-inducible protein 16 |
| 170 | 210460_s_at | HG-U133A | AB033605 | proteasome (prosome, macropain) 26S subunit, non-ATPase, 4 |
| 171 | 217871_s_at | HG-U133A | NM_002415 | macrophage migration inhibitory factor (glycosylation-inhibiting factor) |
| 172 | 208103_s_at | HG-U133A | | |
| 173 | 224579_at | HG-U133B | BF247552 | Solute carrier family 38, member 1 |
| 174 | 203182_s_at | HG-U133A | NM_003138 | SFRS protein kinase 2 |
| 175 | 208743_s_at | HG-U133A | BC001359 | tyrosine 3-monooxygenase/tryptophan 5-monooxygenase activation protein, beta polypeptide |
| 176 | 212766_s_at | HG-U133A | AW294587 | hypothetical protein FLJ12671 |
| 177 | 208716_s_at | HG-U133A | AB020980 | putative membrane protein |
| 178 | 223474_at | HG-U133B | AI932310 | chromosome 14 open reading frame 4 |
| 179 | 217752_s_at | HG-U133A | NM_018235 | CNDP dipeptidase 2 (metallopeptidase M20 family) |
| 180 | 226482_s_at | HG-U133B | AI814545 | F11 receptor |

TABLE 1-continued

| | | Short Term and Long Term Survival Markers | | |
|---|---|---|---|---|
| 181 | 224233_s_at | HG-U133B | BC002535 | misato |
| 182 | 209151_x_at | HG-U133A | | |
| 183 | 203550_s_at | HG-U133A | | |
| 184 | 218826_at | HG-U133A | NM_017515 | solute carrier family 35, member F2 |
| 185 | 203739_at | HG-U133A | NM_006526 | zinc finger protein 217 |
| 186 | 227211_at | HG-U133B | | |
| 187 | 201251_at | HG-U133A | NM_002654 | pyruvate kinase, muscle |
| 188 | 219032_x_at | HG-U133A | NM_014322 | opsin 3 (encephalopsin, panopsin) |
| 189 | 202704_at | HG-U133A | AA675892 | transducer of ERBB2, 1 |
| 190 | 203560_at | HG-U133A | NM_003878 | gamma-glutamyl hydrolase (conjugase, folylpolygammaglutamyl hydrolase) |
| 191 | 226525_at | HG-U133B | N51102 | Serine/threonine kinase 17b (apoptosis-inducing) |
| 192 | 223819_x_at | HG-U133B | | |
| 193 | 223243_s_at | HG-U133B | BF439488 | chromosome 1 open reading frame 22 |
| 194 | 210467_x_at | HG-U133A | BC003408 | melanoma antigen family A, 12 |
| 195 | 218695_at | HG-U133A | NM_019037 | exosome component 4 |
| 196 | 211425_x_at | HG-U133A | | |
| 197 | 213222_at | HG-U133A | | |
| 198 | 236152_at | HG-U133B | | |
| 199 | 201565_s_at | HG-U133A | NM_002166 | inhibitor of DNA binding 2, dominant negative helix-loop-helix protein |
| 200 | 221601_s_at | HG-U133A | AI084226 | regulator of Fas-induced apoptosis |
| 201 | 225400_at | HG-U133B | | |
| 202 | 222632_s_at | HG-U133B | | |
| 203 | 203828_s_at | HG-U133A | NM_004221 | interleukin 32 |
| 204 | 214219_x_at | HG-U133A | BE646618 | mitogen-activated protein kinase kinase kinase kinase 1 |
| 205 | 210394_x_at | HG-U133A | | |
| 206 | 212396_s_at | HG-U133A | AI143233 | KIAA0090 protein |
| 207 | 221602_s_at | HG-U133A | AF057557 | regulator of Fas-induced apoptosis |
| 208 | 225105_at | HG-U133B | BF969397 | hypothetical protein |
| 209 | 210589_s_at | HG-U133A | | |
| 210 | 216471_x_at | HG-U133A | X79200 | synovial sarcoma, X breakpoint 2 |
| 211 | 227126_at | HG-U133B | AI857788 | Transcribed locus |
| 212 | 241224_x_at | HG-U133B | AA770014 | Down syndrome critical region gene 8 |
| 213 | 210497_x_at | HG-U133A | BC002818 | synovial sarcoma, X breakpoint 2 |
| 214 | 207666_x_at | HG-U133A | | |
| 215 | 227174_at | HG-U133B | | |
| 216 | 227194_at | HG-U133B | | |
| 217 | 206626_x_at | HG-U133A | BC001003 | synovial sarcoma, X breakpoint 1 |
| 218 | 228851_s_at | HG-U133B | | |
| 219 | 204944_at | HG-U133A | NM_002841 | protein tyrosine phosphatase, receptor type, G |
| 220 | 204411_at | HG-U133A | NM_017596 | kinesin family member 21B |
| 221 | 217339_x_at | HG-U133A | AJ275978 | cancer/testis antigen 1B |
| 222 | 220057_at | HG-U133A | NM_020411 | X antigen family, member 1 |
| 223 | 211674_x_at | HG-U133A | AF038567 | cancer/testis antigen 1B /// cancer/testis antigen 1A |
| 224 | 210546_x_at | HG-U133A | U87459 | cancer/testis antigen 1B /// cancer/testis antigen 1A |
| 225 | 240336_at | HG-U133B | AI242749 | hemoglobin mu chain |
| 226 | 210746_s_at | HG-U133A | M30646 | erythrocyte membrane protein band 4.2 |
| 227 | 205837_s_at | HG-U133A | BC005319 | glycophorin A (includes MN blood group) |
| 228 | 209301_at | HG-U133A | M36532 | carbonic anhydrase II |
| 229 | 211821_x_at | HG-U133A | U00178 | glycophorin A (includes MN blood group) |
| 230 | 223669_at | HG-U133B | AF130060 | hemogen |
| 231 | 205950_s_at | HG-U133A | NM_001738 | carbonic anhydrase I |
| 232 | 222529_at | HG-U133B | BG251467 | mitochondrial solute carrier protein |

TABLE 1-continued

| | | Short Term and Long Term Survival Markers | | |
|---|---|---|---|---|
| 233 | 228766_at | HG-U133B | AW299226 | CD36 antigen (collagen type I receptor, thrombospondin receptor) |
| 234 | 211820_x_at | HG-U133A | U00179 | glycophorin A (includes MN blood group) |
| 235 | 202219_at | HG-U133A | NM_005629 | solute carrier family 6 (neurotransmitter transporter, creatine), member 8 |
| 236 | 205268_s_at | HG-U133A | NM_017488 | adducin 2 (beta) |
| 237 | 205592_at | HG-U133A | X77737 | Solute carrier family 4, anion exchanger, member 1 (erythrocyte membrane protein band 3, Diego blood group) |
| 238 | 209555_s_at | HG-U133A | M98399 | CD36 antigen (collagen type I receptor, thrombospondin receptor) |
| 239 | 209930_s_at | HG-U133A | L13974 | nuclear factor (erythroid-derived 2), 45 kDa |
| 240 | 210215_at | HG-U133A | AF067864 | transferrin receptor 2 |
| 241 | 210586_x_at | HG-U133A | AF312679 | Rhesus blood group, D antigen |
| 242 | 219672_at | HG-U133A | NM_016633 | erythroid associated factor |
| 243 | 206145_at | HG-U133A | NM_000324 | Rhesus blood group-associated glycoprotein |
| 244 | 214464_at | HG-U133A | NM_003607 | CDC42 binding protein kinase alpha (DMPK-like) |
| 245 | 225061_at | HG-U133B | N45231 | DnaJ (Hsp40) homolog, subfamily A, member 4 |
| 246 | 235916_at | HG-U133B | | |
| 247 | 242197_x_at | HG-U133B | | |
| 248 | 205391_x_at | HG-U133A | M28880 | ankyrin 1, erythrocytic |
| 249 | 210430_x_at | HG-U133A | L08429 | Rhesus blood group, D antigen |
| 250 | 218872_at | HG-U133A | NM_017899 | hypothetical protein FLJ20607 |
| 251 | 223670_s_at | HG-U133B | AF322875 | hemogen |
| 252 | 219073_s_at | HG-U133A | NM_017784 | oxysterol binding protein-like 10 |
| 253 | 227654_at | HG-U133B | AI056877 | similar to KIAA0386 |
| 254 | 234980_at | HG-U133B | AI004375 | Hypothetical protein FLJ31842 |
| 255 | 205389_s_at | HG-U133A | AI659683 | ankyrin 1, erythrocytic |
| 256 | 237403_at | HG-U133B | AI097490 | growth factor independent 1B (potential regulator of CDKN1A, translocated in CML) |
| 257 | 207459_x_at | HG-U133A | NM_002100 | glycophorin B (includes Ss blood group) |
| 258 | 204249_s_at | HG-U133A | NM_005574 | LIM domain only 2 (rhombotin-like 1) |
| 259 | 207677_s_at | HG-U133A | NM_013416 | neutrophil cytosolic factor 4, 40 kDa |
| 260 | 208352_x_at | HG-U133A | NM_020479 | ankyrin 1, erythrocytic |
| 261 | 208886_at | HG-U133A | BC000145 | H1 histone family, member 0 |
| 262 | 230788_at | HG-U133B | BF059748 | glucosaminyl (N-acetyl) transferase 2, I-branching enzyme |
| 263 | 201952_at | HG-U133A | AA156721 | |
| 264 | 214407_x_at | HG-U133A | AI240545 | glycophorin B (includes Ss blood group) |
| 265 | 220751_s_at | HG-U133A | NM_016348 | chromosome 5 open reading frame 4 |
| 266 | 203662_s_at | HG-U133A | | |
| 267 | 226751_at | HG-U133B | | |
| 268 | 205262_at | HG-U133A | NM_000238 | potassium voltage-gated channel, subfamily H (eag-related), member 2 |
| 269 | 208416_s_at | HG-U133A | NM_000347 | spectrin, beta, erythrocytic (includes spherocytosis, clinical type I) |
| 270 | 208691_at | HG-U133A | BC001188 | |
| 271 | 205390_s_at | HG-U133A | NM_000037 | ankyrin 1, erythrocytic |
| 272 | 232232_s_at | HG-U133B | | |
| 273 | 206937_at | HG-U133A | NM_003126 | spectrin, alpha, erythrocytic 1 (elliptocytosis 2) |

TABLE 1-continued

| | | Short Term and Long Term Survival Markers | | |
|---|---|---|---|---|
| 274 | 215449_at | HG-U133A | AI052224 | Benzodiazapine receptor (peripheral)-like 1 |
| 275 | 215819_s_at | HG-U133A | N53959 | Rhesus blood group, CcEe antigens /// Rhesus blood group, D antigen |
| 276 | 209160_at | HG-U133A | AB018580 | aldo-keto reductase family 1, member C3 (3-alpha hydroxysteroid dehydrogenase, type II) |
| 277 | 203196_at | HG-U133A | | |
| 278 | 206488_s_at | HG-U133A | NM_000072 | CD36 antigen (collagen type I receptor, thrombospondin receptor) |
| 279 | 207332_s_at | HG-U133A | NM_003234 | transferrin receptor (p90, CD71) |
| 280 | 210044_s_at | HG-U133A | BC002796 | lymphoblastic leukemia derived sequence 1 |
| 281 | 211922_s_at | HG-U133A | AY028632 | catalase |
| 282 | 217202_s_at | HG-U133A | U08626 | glutamate-ammonia ligase (glutamine synthase) |
| 283 | 205154_at | HG-U133A | | |
| 284 | 200697_at | HG-U133A | NM_000188 | hexokinase 1 |
| 285 | 208981_at | HG-U133A | AA702701 | platelet/endothelial cell adhesion molecule (CD31 antigen) |
| 286 | 208982_at | HG-U133A | AW574504 | platelet/endothelial cell adhesion molecule (CD31 antigen) |
| 287 | 210504_at | HG-U133A | U65404 | Kruppel-like factor 1 (erythroid) |
| 288 | 215001_s_at | HG-U133A | AL161952 | glutamate-ammonia ligase (glutamine synthase) |
| 289 | 213451_x_at | HG-U133A | | |
| 290 | 206093_x_at | HG-U133A | NM_007116 | tenascin XB |
| 291 | 202201_at | HG-U133A | NM_000713 | biliverdin reductase B (flavin reductase (NADPH)) |
| 292 | 216333_x_at | HG-U133A | | |
| 293 | 224970_at | HG-U133B | AA419275 | nuclear factor I/A |
| 294 | 205859_at | HG-U133A | NM_004271 | lymphocyte antigen 86 |
| 295 | 216833_x_at | HG-U133A | U05255 | glycophorin B (includes Ss blood group) /// glycophorin E |
| 296 | 208335_s_at | HG-U133A | NM_002036 | Duffy blood group |
| 297 | 210036_s_at | HG-U133A | AB044806 | potassium voltage-gated channel, subfamily H (eag-related), member 2 |
| 298 | 212614_at | HG-U133A | BG285011 | AT rich interactive domain 5B (MRF1-like) |
| 299 | 236981_at | HG-U133B | AI242058 | Clone DNA57836 GLPG464 (UNQ464) mRNA, complete cds |
| 300 | 37986_at | HG-U133A | M60459 | erythropoietin receptor |
| 301 | 202931_x_at | HG-U133A | | |
| 302 | 228278_at | HG-U133B | | |
| 303 | 206077_at | HG-U133A | NM_000420 | Kell blood group |
| 304 | 208353_x_at | HG-U133A | NM_020480 | ankyrin 1, erythrocytic |
| 305 | 210395_x_at | HG-U133A | AF116676 | myosin, light polypeptide 4, alkali; atrial, embryonic |
| 306 | 218729_at | HG-U133A | NM_020169 | latexin |
| 307 | 209894_at | HG-U133A | | |
| 308 | 205147_x_at | HG-U133A | NM_000631 | neutrophil cytosolic factor 4, 40 kDa |
| 309 | 206283_s_at | HG-U133A | NM_003189 | T-cell acute lymphocytic leukemia 1 |
| 310 | 207087_x_at | HG-U133A | NM_020478 | ankyrin 1, erythrocytic |
| 311 | 60471_at | HG-U133A | AA625133 | Ras and Rab interactor 3 |
| 312 | 31874_at | HG-U133A | | |
| 313 | 202151_s_at | HG-U133A | NM_016172 | ubiquitin associated domain containing 1 |
| 314 | 204319_s_at | HG-U133A | NM_002925 | regulator of G-protein signalling 10 |
| 315 | 201432_at | HG-U133A | NM_001752 | catalase |
| 316 | 209047_at | HG-U133A | AL518391 | aquaporin 1 (channel-forming integral protein, 28 kDa) |
| 317 | 210088_x_at | HG-U133A | M36172 | myosin, light polypeptide 4, alkali; atrial, embryonic |
| 318 | 210986_s_at | HG-U133A | Z24727 | tropomyosin 1 (alpha) |

TABLE 1-continued

| | | Short Term and Long Term Survival Markers | | |
|---|---|---|---|---|
| 319 | 212372_at | HG-U133A | AK026977 | myosin, heavy polypeptide 10, non-muscle |
| 320 | 209276_s_at | HG-U133A | AF162769 | glutaredoxin (thioltransferase) |
| 321 | 220558_x_at | HG-U133A | | |
| 322 | 210835_s_at | HG-U133A | AF222711 | C-terminal binding protein 2 |
| 323 | 211993_at | HG-U133A | AI768512 | WNK lysine deficient protein kinase 1 |
| 324 | 212699_at | HG-U133A | BE222801 | secretory carrier membrane protein 5 |
| 325 | 221636_s_at | HG-U133A | | |
| 326 | 235396_at | HG-U133B | | |
| 327 | 239492_at | HG-U133B | | |
| 328 | 226726_at | HG-U133B | W63676 | O-acyltransferase (membrane bound) domain containing 2 |
| 329 | 211074_at | HG-U133A | | |
| 330 | 206896_s_at | HG-U133A | NM_005145 | guanine nucleotide binding protein (G protein), gamma 7 |
| 331 | 207269_at | HG-U133A | NM_001925 | defensin, alpha 4, corticostatin |
| 332 | 229740_at | HG-U133B | BF478120 | RecQ protein-like 5 /// PP12104 |
| 333 | 221824_s_at | HG-U133A | AA770170 | membrane-associated ring finger (C3HC4) 8 |
| 334 | 216054_x_at | HG-U133A | X58851 | myosin, light polypeptide 4, alkali; atrial, embryonic |
| 335 | 203845_at | HG-U133A | AV727449 | p300/CBP-associated factor |
| 336 | 217274_x_at | HG-U133A | X52005 | myosin, light polypeptide 4, alkali; atrial, embryonic |
| 337 | 211105_s_at | HG-U133A | | |
| 338 | 218394_at | HG-U133A | | |
| 339 | 48031_r_at | HG-U133A | | |
| 340 | 225373_at | HG-U133B | BE271644 | PP2135 protein |
| 341 | 202947_s_at | HG-U133A | NM_002101 | glycophorin C (Gerbich blood group) |
| 342 | 218450_at | HG-U133A | NM_015987 | heme binding protein 1 |
| 343 | 212739_s_at | HG-U133A | AL523860 | non-metastatic cells 4, protein expressed in |
| 344 | 201250_s_at | HG-U133A | NM_006516 | solute carrier family 2 (facilitated glucose transporter), member 1 |
| 345 | 218456_at | HG-U133A | NM_023925 | C1q domain containing 1 |
| 346 | 215811_at | HG-U133A | AF238870 | |
| 347 | 226599_at | HG-U133B | AA527080 | KIAA1727 protein |
| 348 | 221627_at | HG-U133A | AF220123 | tripartite motif-containing 10 |
| 349 | 201220_x_at | HG-U133A | NM_001329 | C-terminal binding protein 2 |
| 350 | 218066_at | HG-U133A | NM_006598 | solute carrier family 12 (potassium/chloride transporters), member 7 |
| 351 | 203124_s_at | HG-U133A | | |
| 352 | 204294_at | HG-U133A | NM_000481 | aminomethyltransferase (glycine cleavage system protein T) |
| 353 | 208866_at | HG-U133A | BF510713 | casein kinase 1, alpha 1 |
| 354 | 208971_at | HG-U133A | M14016 | uroporphyrinogen decarboxylase |
| 355 | 218208_at | HG-U133A | NM_025078 | PQ loop repeat containing 1 |
| 356 | 202449_s_at | HG-U133A | NM_002957 | retinoid X receptor, alpha |
| 357 | 203123_s_at | HG-U133A | AU154469 | solute carrier family 11 (proton-coupled divalent metal ion transporters), member 2 |
| 358 | 210944_s_at | HG-U133A | BC003169 | calpain 3, (p94) |
| 359 | 210778_s_at | HG-U133A | | |
| 360 | 37590_g_at | HG-U133A | | |
| 361 | 205927_s_at | HG-U133A | NM_001910 | cathepsin E |
| 362 | 228831_s_at | HG-U133B | AL039870 | guanine nucleotide binding protein (G protein), gamma 7 |
| 363 | 218552_at | HG-U133A | | |
| 364 | 217889_s_at | HG-U133A | NM_024843 | cytochrome b reductase 1 |
| 365 | 202587_s_at | HG-U133A | BC001116 | adenylate kinase 1 |
| 366 | 212632_at | HG-U133A | N32035 | Syntaxin 7 |
| 367 | 213288_at | HG-U133A | AI761250 | O-acyltransferase (membrane bound) domain containing 2 |
| 368 | 237568_at | HG-U133B | H67156 | Mitochondrial solute carrier protein |

TABLE 1-continued

Short Term and Long Term Survival Markers

| | | | | |
|---|---|---|---|---|
| 369 | 53987_at | HG-U133A | AL041852 | RAN binding protein 10 |
| 370 | 209380_s_at | HG-U133A | | |
| 371 | 201865_x_at | HG-U133A | AI432196 | nuclear receptor subfamily 3, group C, member 1 (glucocorticoid receptor) |
| 372 | 203668_at | HG-U133A | NM_006715 | mannosidase, alpha, class 2C, member 1 |
| 373 | 213657_s_at | HG-U133A | BE858194 | Hypothetical protein DKFZp547K1113 |
| 374 | 210987_x_at | HG-U133A | M19267 | Tropomyosin 1 (alpha) |
| 375 | 231616_at | HG-U133B | | |
| 376 | 202492_at | HG-U133A | NM_024085 | APG9 autophagy 9-like 1 (*S. cerevisiae*) |
| 377 | 204151_x_at | HG-U133A | NM_001353 | aldo-keto reductase family 1, member C1 (dihydrodiol dehydrogenase 1; 20-alpha (3-alpha)-hydroxysteroid dehydrogenase) |
| 378 | 213327_s_at | HG-U133A | AI820101 | |
| 379 | 213572_s_at | HG-U133A | AI554300 | serine (or cysteine) proteinase inhibitor, clade B (ovalbumin), member 1 |
| 380 | 35160_at | HG-U133A | | |
| 381 | 209018_s_at | HG-U133A | BF432478 | PTEN induced putative kinase 1 |
| 382 | 212284_x_at | HG-U133A | BG498776 | tumor protein, translationally-controlled 1 |
| 383 | 203633_at | HG-U133A | | |
| 384 | 210844_x_at | HG-U133A | D14705 | catenin (cadherin-associated protein), alpha 1, 102 kDa |
| 385 | 216231_s_at | HG-U133A | AW188940 | beta-2-microglobulin |
| 386 | 200765_x_at | HG-U133A | NM_001903 | catenin (cadherin-associated protein), alpha 1, 102 kDa |
| 387 | 201871_s_at | HG-U133A | NM_015853 | ORF |
| 388 | 208908_s_at | HG-U133A | AF327443 | calpastatin |
| 389 | 218603_at | HG-U133A | NM_016217 | headcase homolog (*Drosophila*) |
| 390 | 202334_s_at | HG-U133A | | |
| 391 | 216594_x_at | HG-U133A | S68290 | aldo-keto reductase family 1, member C1 (dihydrodiol dehydrogenase 1; 20-alpha (3-alpha)-hydroxysteroid dehydrogenase) /// aldo-keto reductase family 1, member C2 (dihydrodiol dehydrogenase 2; bile acid binding protein; 3-alpha hydroxysteroid dehydrogenase, type III) |
| 392 | 209475_at | HG-U133A | AF106069 | ubiquitin specific protease 15 |
| 393 | 213601_at | HG-U133A | AB011537 | slit homolog 1 (*Drosophila*) |
| 394 | 201886_at | HG-U133A | NM_025230 | WD repeat domain 23 |
| 395 | 218126_at | HG-U133A | NM_018145 | hypothetical protein FLJ10579 |
| 396 | 207467_x_at | HG-U133A | NM_001750 | calpastatin |
| 397 | 213477_x_at | HG-U133A | AL515273 | eukaryotic translation elongation factor 1 alpha 1 |
| 398 | 225235_at | HG-U133B | AW007710 | transmembrane 4 superfamily member 17 |
| 399 | 213614_x_at | HG-U133A | BE786672 | eukaryotic translation elongation factor 1 alpha 1 |
| 400 | 216326_s_at | HG-U133A | | |
| 401 | 204892_x_at | HG-U133A | NM_001402 | eukaryotic translation elongation factor 1 alpha 1 |
| 402 | 45749_at | HG-U133A | AA400206 | hypothetical protein FLJ13725 |
| 403 | 201643_x_at | HG-U133A | | |

| No | Gene symbol | Entrez ID | Short Term | Long Term | Hazard Ratio | Resp | TTP | Biol Cat |
|---|---|---|---|---|---|---|---|---|
| 1 | PSME3 | 10197 | X | | 4.54 | | | P, U, V |
| 2 | ELAVL1 | 1994 | X | | 4.37 | | V− | M |
| 3 | PSMB4 | 5692 | X | | 3.65 | V− | V− D− | P, Q |
| 4 | CPSF6 | 11052 | X | | 3.57 | V− | V− | W |
| 5 | BAT2D1 | 23215 | X | | 3.55 | | V− | |

TABLE 1-continued

Short Term and Long Term Survival Markers

| | | | | | | | |
|---|---|---|---|---|---|---|---|
| 6 | GPR89 | 51463 /// 653519 | X | 3.51 | D- | V- D- | |
| 7 | RBBP8 | 5932 | X | 3.48 | | V- | M, T |
| 8 | ISG20L2 | 81875 | X | 3.47 | | | |
| 9 | ZNF364 | 27246 | X | 3.36 | | | P |
| 10 | CDKN2A | 1029 | X | 3.35 | D- | V- D- | C, U, V |
| 11 | USP21 | 27005 | X | 3.23 | | | |
| 12 | GPR89 | 51463 /// 653519 | X | 3.21 | | V- D- | |
| 13 | GPR89 | 51463 /// 653519 | X | 3.2 | D- | V- D- | |
| 14 | ATIC | 471 | X | 3.17 | | V- | K |
| 15 | MGC22793 | 221908 | X | 3.17 | V- | V- | |
| 16 | TCEB1 | 6921 | X | 3.08 | | | P |
| 17 | GPR89 | 51463 /// 653519 | X | 3.05 | D- | V- D- | |
| 18 | NDUFS2 | 4720 | X | 3.04 | | D- | R |
| 19 | SCAMP3 | 10067 | X | 3.02 | | | P, Q |
| 20 | TH1L | 51497 | X | 3 | V- | | |
| 21 | POLR3E | 55718 | X | 2.91 | | | |
| 22 | PRKDC | 5591 | X | 2.89 | | V- | M, U, V |
| 23 | NONO | 4841 | X | 2.88 | V- | | U |
| 24 | GLTP | 51228 | X | 2.86 | | | |
| 25 | PFDN2 | 5202 | X | 2.86 | V- D- | V- | J, K |
| 26 | ZNF330 | 27309 | X | 2.85 | | | |
| 27 | ATP5G1 | 516 | X | 2.83 | D- | V- D- | R, K |
| 28 | ADSS | 159 | X | 2.82 | | | |
| 29 | PNPT1 | 87178 | X | 2.81 | | | R |
| 30 | TAF2 | 6873 | X | 2.81 | | | K |
| 31 | ABCE1 | 6059 | X | 2.79 | | | K, Q |
| 32 | MRPL9 | 65005 | X | 2.79 | V- | V- | R |
| 33 | C20orf3 | 57136 | X | 2.78 | D- | | |
| 34 | SDHC | 6391 | X | 2.77 | | D- | R |
| 35 | GPATC4 | 54865 | X | 2.74 | | | |
| 36 | ALDH9A1 | 223 | X | 2.74 | | V- | R |
| 37 | PRKDC | 5591 | X | 2.73 | | V- | M, U, V |
| 38 | TH1L | 51497 | X | 2.73 | V- | V- | |
| 39 | PMS2L1 | 5379 | X | 2.72 | | V- | |
| 40 | C20orf24 | 55969 | X | 2.71 | | | T |
| 41 | NMT1 | 4836 | X | 2.71 | D- | | S, Q |
| 42 | TA-PP2C | 160760 | X | 2.7 | | | |
| 43 | ATXN10 | 25814 | X | 2.7 | V- | V- | V, Q |
| 44 | APH1A | 51107 | X | 2.67 | | | T |
| 45 | UCHL5 | 51377 | X | 2.67 | | | P, Q |
| 46 | COPS5 | 10987 | X | 2.66 | | V- | P, Q |
| 47 | SDHC | 6391 /// 642502 | X | 2.66 | | D- | R |
| 48 | PSMC2 | 5701 | X | 2.64 | | | P, Q |
| 49 | SF3B4 | 10262 | X | 2.64 | | | W |
| 50 | SDHC | 6391 | X | 2.63 | | | R |
| 51 | CHORDC1 | 26973 | X | 2.59 | | | |
| 52 | COX6C | 1345 | X | 2.58 | V- | V- | R, Q |
| 53 | XPO1 | 7514 | X | 2.58 | | V- | V, Q |
| 54 | KLHL11 | | X | 2.58 | | | |
| 55 | MRPL24 | 79590 | X | 2.57 | | | M, Q |
| 56 | S100PBPR | 64766 | X | 2.57 | | | |
| 57 | FH | 2271 | X | 2.55 | | | R, Q |
| 58 | EIF2S1 | 1965 | X | 2.54 | V- D- | V- D- | P, Q |
| 59 | TH1L | 51497 | X | 2.54 | V- | V- | |
| 60 | TFB2M | 64216 | X | 2.53 | | | R |
| 61 | CUL1 | 8454 | X | 2.53 | V- | V- | P, K |
| 62 | MSN | 4478 | X | 2.52 | | | V, T |
| 63 | PARP1 | 142 | X | 2.52 | | | U, Q |
| 64 | SLC25A32 | 81034 | X | 2.51 | | | R |
| 65 | MTX1 | 4580 | X | 2.51 | D- | D- | R, Q |
| 66 | PPT1 | 5538 | X | 2.5 | | | |
| 67 | ACLY | 47 | X | 2.48 | | V- | K |
| 68 | PSMD4 | 5710 | X | 2.47 | | V- | P, Q |
| 69 | FBXO28 | 23219 | X | 2.47 | | | T |
| 70 | MAC30 | 27346 | X | 2.46 | V- | V- | |
| 71 | C10orf22 | 84890 | X | 2.44 | | | |
| 72 | | | X | 2.44 | | | |
| 73 | FDPS | 2224 | X | 2.43 | D- | V- D- | V, Q |

TABLE 1-continued

| | | Short Term and Long Term Survival Markers | | | | | |
|---|---|---|---|---|---|---|---|
| 74 | PMS2L5 | 441259 /// 5383 /// 641799 /// 641800 /// 645243 /// 645248 | X | 2.4 | | V− | |
| 75 | FLJ10534 | 55720 | X | 2.37 | | | |
| 76 | GLRX2 | 51022 | X | 2.35 | | | R, K |
| 77 | IMPAD1 | 54928 | X | 2.35 | | V− | |
| 78 | MRPS14 | 63931 | X | 2.33 | | | R, Q |
| 79 | ADAR | 103 | X | 2.32 | | | M |
| 80 | FLJ20485 | 54517 | X | 2.32 | | | |
| 81 | CACYBP | 27101 | X | 2.32 | D− | | Q |
| 82 | DAP3 | 7818 | X | 2.32 | V− | V− | R |
| 83 | C1orf121 | 51029 | X | 2.31 | | D− | S, T |
| 84 | TH1L | 51497 | X | 2.31 | V− | V− | |
| 85 | CTPS | 1503 | X | 2.31 | | | K, Q |
| 86 | WDSOF1 | 25879 | X | 2.3 | | | K |
| 87 | ARHGAP30 | 257106 | X | 2.3 | D− | D− | |
| 88 | LOC283871 | 79118 | X | 2.3 | | | |
| 89 | NAT5 | 51126 | X | 2.29 | | | |
| 90 | MGC4767 | 84274 | X | 2.29 | | | |
| 91 | AMZ2 | 51321 | X | 2.28 | | | |
| 92 | LOC219854 | 219854 | X | 2.28 | V− | | |
| 93 | ZNF664 | 144348 | X | 2.27 | | | V |
| 94 | BAT2D1 | | X | 2.26 | | | |
| 95 | IMPAD1 | 54928 | X | 2.25 | | | |
| 96 | GPR172A | 79581 | X | 2.25 | D− | D− | |
| 97 | CECR5 | 27440 | X | 2.25 | D− | D− | |
| 98 | LASS2 | 29956 | X | 2.25 | V− | | |
| 99 | MGC4308 | 84319 | X | 2.25 | V− | | |
| 100 | FH | 2271 | X | 2.24 | | D− | R |
| 101 | DCPS | 28960 | X | 2.24 | V− | | K, Q |
| 102 | ZNF281 | 23528 | X | 2.23 | V− | | |
| 103 | RBM8A | 9939 | X | 2.23 | | V− D− | W |
| 104 | PSMD14 | 10213 | X | 2.22 | | | S, Q |
| 105 | GRSF1 | 2926 | X | 2.21 | V− | | |
| 106 | ACBD6 | 84320 | X | 2.21 | V− | V− | |
| 107 | IARS2 | 55699 | X | 2.2 | | D− | R, T |
| 108 | HADH2 | 3028 | X | 2.19 | V− | | R, Q |
| 109 | TIMM17A | 10440 | X | 2.19 | | D− | R, S |
| 110 | PSMB4 | 5692 | X | 2.17 | | | P, Q |
| 111 | LDLRAP1 | 26119 | X | 2.17 | | | |
| 112 | SLC35B4 | 84912 | X | 2.17 | | | |
| 113 | GPATC4 | 54865 | X | 2.17 | D− | | |
| 114 | FNTA | 2339 | X | 2.15 | | V− | K |
| 115 | ZC3H5 | 85451 | X | 2.15 | | | K |
| 116 | XPOT | 11260 | X | 2.13 | | | W |
| 117 | CYC1 | 1537 | X | 2.12 | V− | V− | R |
| 118 | PSMA6 | 5687 | X | 2.11 | | | P, Q |
| 119 | ATP2A2 | 488 | X | 2.11 | | | K, U |
| 120 | CCT3 | 7203 | X | 2.1 | V− | V− | K, Q |
| 121 | MAC30 | 27346 | X | 2.1 | V− | | |
| 122 | CNIH4 | 29097 | X | 2.1 | | | |
| 123 | | 116064 | X | 2.09 | | | |
| 124 | TRRAP | 8295 | X | 2.09 | | V− | T |
| 125 | PSMD4 | 5710 | X | 2.08 | | V− | P, Q |
| 126 | MINA | 84864 | X | 2.06 | | | |
| 127 | CAD | 790 | X | 2.06 | | V− | U, Q |
| 128 | GFM1 | 85476 | X | 2.05 | | | R, Q |
| 129 | GBA; GBAP | 2629 /// 2630 | X | 2.04 | | | |
| 130 | PHF14 | 9678 | X | 2.02 | V− | | |
| 131 | SQLE | 6713 | X | 2.01 | | | S |
| 132 | LYPLA1 | 10434 | X | 2.01 | | | Q |
| 133 | DR1 | 1810 | X | 2.01 | V− | V− | T |
| 134 | C1orf19 | 116461 | X | 1.98 | | | Q |
| 135 | ZNF281 | 23528 | X | 1.96 | V− | | |
| 136 | TA-PP2C | 160760 | X | 1.95 | | | |
| 137 | PHF19 | 26147 | X | 1.95 | | | K |
| 138 | ERO1L | 30001 | X | 1.94 | | | J |
| 139 | NUP210 | 23225 | X | 1.94 | V− | | |
| 140 | GPR172A | 79581 | X | 1.93 | | | |
| 141 | MAC30 | 27346 | X | 1.93 | V− | | |

TABLE 1-continued

| Short Term and Long Term Survival Markers | | | | | | | |
|---|---|---|---|---|---|---|---|
| 142 | ABCF2 | 10061 | X | 1.93 | | | R |
| 143 | AG1 | 149013 /// 200030 /// 25832 /// 284565 /// 440670 /// 440673 /// 440675 /// 55672 /// 644291 | X | 1.92 | | | |
| 144 | C7orf19 | 80228 | X | 1.91 | | | |
| 145 | APS | 10603 | X | 1.91 | D- | V- | I |
| 146 | METTL2; FLJ12760 | 339175 /// 55798 | X | 1.9 | | | |
| 147 | STK17B | 9262 | X | 1.89 | | | G |
| 148 | TMCO1 | 54499 | X | 1.88 | | | |
| 149 | TM7SF3 | 51768 | X | 1.88 | | | |
| 150 | C1orf85 | 112770 | X | 1.88 | D- | | |
| 151 | TIMM17A | 10440 | X | 1.87 | | | R, S |
| 152 | SLC38A1 | 81539 | X | 1.87 | | | T, V |
| 153 | C1orf19 | 116461 | X | 1.86 | | | Q |
| 154 | NDUFA12 | 55967 | X | 1.86 | V- | | R |
| 155 | ARHGEF2 | 9181 | X | 1.85 | | | M |
| 156 | MGC5576 | 79022 | X | 1.85 | D- | V- | D- |
| 157 | CKS1B | 1163 | X | 1.85 | D- | V- D- | M, Q |
| 158 | B4GALT3 | 8703 | X | 1.85 | V- | V- | K |
| 159 | CXXC1 | 30827 | X | 1.85 | D- | D- | |
| 160 | DRAP1 | 10589 | X | 1.84 | V- | | |
| 161 | TPP1 | 1200 | X | 1.83 | | | |
| 162 | UAP1 | 6675 | X | 1.82 | D- | D- | |
| 163 | NUP210 | 23225 | X | 1.82 | V- | V- | |
| 164 | PYCR2 | 29920 | X | 1.82 | | V- | |
| 165 | GUSB | 2990 | X | 1.81 | V- | V- | Q |
| 166 | CBX4 | 8535 | X | 1.81 | V- | | |
| 167 | MRPS21 | 54460 | X | 1.8 | V- | V- D- | R, Q |
| 168 | | | X | 1.79 | | | |
| 169 | IFI16 | 3428 | X | 1.78 | | | M, K |
| 170 | PSMD4 | 5710 | X | 1.78 | | V- | P, Q |
| 171 | MIF | 4282 | X | 1.77 | V- D- | D- | T |
| 172 | ANP32E | 81611 | X | 1.77 | | | T |
| 173 | SLC38A1 | | X | 1.76 | | | T, V |
| 174 | SRPK2 | 6733 | X | 1.76 | D- | D- | |
| 175 | YWHAB | 7529 | X | 1.76 | V- | V- | I |
| 176 | ISG20L2 | 81875 | X | 1.75 | V- | | |
| 177 | TMCO1 | 54499 | X | 1.74 | | | |
| 178 | C14orf4 | 64207 | X | 1.74 | V- | V- | |
| 179 | CNDP2 | 55748 | X | 1.73 | | | K |
| 180 | F11R | 50848 | X | 1.72 | | | L |
| 181 | MSTO1 | 55154 | X | 1.7 | | D- | R, G |
| 182 | TCF3 | 6929 | X | 1.7 | | | M, V |
| 183 | C1orf2 | 10712 | X | 1.66 | | | |
| 184 | SLC35F2 | 54733 | X | 1.63 | | | |
| 185 | ZNF217 | 7764 | X | 1.63 | V- | V- | |
| 186 | PHF19 | 26147 | X | 1.63 | | | K |
| 187 | PKM2 | 5315 | X | 1.59 | | | K, V |
| 188 | OPN3 | 23596 | X | 1.56 | | | |
| 189 | TOB1 | 10140 | X | 1.54 | | | K |
| 190 | GGH | 8836 | X | 1.53 | V- | V- | K, U |
| 191 | STK17B | | X | 1.51 | D- | V- | G |
| 192 | COMMD5 | 28991 | X | 1.51 | | | |
| 193 | C1orf22 | 653815 /// 80267 | X | 1.48 | | | |
| 194 | MAGEA12 | 4111 | X | 1.44 | | V- | D, V |
| 195 | EXOSC4 | 54512 | X | 1.44 | D- | | T |
| 196 | SSX4 | 548313 /// 6759 | X | 1.44 | | | D |
| 197 | PLCB1 | 23236 | X | 1.44 | | | |
| 198 | PAGE5 | 90737 | X | 1.44 | | | D |

TABLE 1-continued

Short Term and Long Term Survival Markers

| # | Name | ID | ST | LT | Value | C1 | C2 | C3 | Letters |
|---|---|---|---|---|---|---|---|---|---|
| 199 | ID2 | 3398 | X | | 1.43 | | | | K, S |
| 200 | FAIM3 | 9214 | X | | 1.43 | | V− | | G, E |
| 201 | C1orf19 | 116461 | X | | 1.42 | | | | Q |
| 202 | LZTFL1 | 54585 | X | | 1.41 | | | | C |
| 203 | IL32 | 9235 | X | | 1.39 | | | | L, E |
| 204 | MAP4K1 | 11184 | X | | 1.39 | | | | M, T |
| 205 | SSX4 | 548313 /// 6759 | X | | 1.38 | | | | D |
| 206 | KIAA0090 | 23065 | X | | 1.37 | | | | |
| 207 | FAIM3 | 9214 | X | | 1.36 | | V− | | G, E |
| 208 | LOC387882 | 387882 | X | | 1.34 | D− | D− | | |
| 209 | GBA; GBAP | 2629 /// 2630 | X | | 1.34 | | | | |
| 210 | SSX2 | 653088 /// 6757 | X | | 1.32 | V− | D− | D− | D |
| 211 | | | X | | 1.3 | V− | | | |
| 212 | DSCR8 | 84677 | X | | 1.3 | D− | V− | | |
| 213 | SSX2 | 653088 /// 6757 | X | | 1.29 | V− | D− | D− | D |
| 214 | SSX3 | 10214 | X | | 1.29 | | | | D |
| 215 | WDR72 | 256764 | X | | 1.29 | | | | |
| 216 | FAM3B | 54097 | X | | 1.29 | | | | |
| 217 | SSX1 | 652630 /// 6756 | X | | 1.28 | V− | D− | D− | D |
| 218 | ENSA | 2029 | X | | 1.28 | | | | K |
| 219 | PTPRG | 5793 | X | | 1.27 | V− | | | V |
| 220 | KIF21B | 23046 | X | | 1.24 | | | | |
| 221 | CTAG1B | 653387 | X | | 1.21 | V− | V− | | D |
| 222 | XAGE1 | 653048 /// 653067 /// 653219 /// 653220 /// 9503 | X | | 1.2 | D− | V− | D− | D |
| 223 | CTAG1B; CTAG1A | 1485 /// 246100 /// 653387 | X | | 1.18 | V− | V− | | D |
| 224 | CTAG1B; CTAG1A | 1485 /// 246100 /// 653387 | X | | 1.16 | V− | V− | | D |
| 225 | HBM | 3042 | | X | 0.86 | | | | F |
| 226 | EPB42 | 2038 | | X | 0.85 | | | | F |
| 227 | GYPA | 2993 | | X | 0.83 | | | | F |
| 228 | CA2 | 760 | | X | 0.83 | | | | |
| 229 | GYPA | 2993 | | X | 0.83 | | | | F |
| 230 | HEMGN | 55363 | | X | 0.83 | | | | F, Q |
| 231 | CA1 | 759 | | X | 0.82 | | | | |
| 232 | SLC25A37 | 51312 | | X | 0.82 | | | | R |
| 233 | CD36 | | | X | 0.82 | | | | L, F |
| 234 | GYPA | 2993 | | X | 0.81 | D+ | | | F |
| 235 | SLC6A8 | 6535 | | X | 0.8 | | | | |
| 236 | ADD2 | 119 | | X | 0.8 | | | | |
| 237 | SLC4A1 | 6521 | | X | 0.8 | | | | F |
| 238 | CD36 | 948 | | X | 0.8 | | | | F, L |
| 239 | NFE2 | 4778 | | X | 0.8 | D+ | | | F |
| 240 | TFR2 | 7036 | | X | 0.79 | | | | |
| 241 | RHD | 6007 | | X | 0.79 | | | | F |
| 242 | ERAF | 51327 | | X | 0.79 | | | | F |
| 243 | RHAG | 6005 | | X | 0.78 | | | | F, Q |
| 244 | CDC42BPA | 8476 | | X | 0.78 | | | | K |
| 245 | DNAJA4 | 55466 | | X | 0.78 | | | | J |
| 246 | YPEL4 | 219539 | | X | 0.78 | | | | |
| 247 | CD36 | 948 | | X | 0.78 | | | | F |
| 248 | ANK1 | 286 | | X | 0.77 | | | | F |
| 249 | RHD | 6007 | | X | 0.77 | | | | F |
| 250 | TSC | 54997 | | X | 0.77 | | | | |
| 251 | HEMGN | 55363 | | X | 0.77 | | | | F, Q |
| 252 | OSBPL10 | 114884 | | X | 0.77 | V+ | V+ | | |
| 253 | LOC200230 | 200230 | | X | 0.76 | | | | |
| 254 | TMEM56 | 148534 | | X | 0.76 | | | | K, Q |
| 255 | ANK1 | 286 | | X | 0.76 | D+ | | | F, Q |
| 256 | GFI1B | 8328 | | X | 0.75 | | | | G |
| 257 | GYPB | 2994 | | X | 0.75 | D+ | | | F |
| 258 | LMO2 | 4005 | | X | 0.74 | | | | T |

TABLE 1-continued

| | | Short Term and Long Term Survival Markers | | | | | |
|---|---|---|---|---|---|---|---|
| 259 | NCF4 | 4689 | X | 0.74 | | | Q |
| 260 | ANK1 | 286 | X | 0.74 | | | F |
| 261 | H1F0 | 3005 | X | 0.74 | | | P, Q |
| 262 | GCNT2 | 2651 | X | 0.74 | | | T |
| 263 | ALCAM | 214 | X | 0.74 | | D+ | |
| 264 | GYPB | 2994 | X | 0.74 | D+ | | F |
| 265 | C5orf4 | 10826 | X | 0.74 | D+ | | V |
| 266 | TMOD1 | 7111 | X | 0.74 | | | F |
| 267 | C2orf32 | 25927 | X | 0.74 | | | |
| 268 | KCNH2 | 3757 | X | 0.73 | | | F |
| 269 | SPTB | 6710 | X | 0.73 | | | F |
| 270 | TFRC | 7037 | X | 0.73 | | | S, U |
| 271 | ANK1 | 286 | X | 0.73 | D+ | | F, T |
| 272 | SLC22A16 | 85413 | X | 0.73 | | | |
| 273 | SPTA1 | 6708 | X | 0.72 | | | F |
| 274 | BZRPL1 | 222642 | X | 0.72 | | | |
| 275 | RHCE; RHD | 6006 /// 6007 | X | 0.72 | | | F |
| 276 | AKR1C3 | 8644 | X | 0.72 | D+ | | V |
| 277 | ABCC4 | 10257 | X | 0.72 | | | K, U |
| 278 | CD36 | 948 | X | 0.71 | | | F |
| 279 | TFRC | 7037 | X | 0.71 | | | S, U |
| 280 | LYL1 | 4066 | X | 0.71 | | | Q |
| 281 | CAT | 847 | X | 0.71 | | | V |
| 282 | GLUL | 2752 | X | 0.71 | V+ | | |
| 283 | LRRN5 | 10446 | X | 0.71 | | | L |
| 284 | HK1 | 3098 | X | 0.7 | | | F |
| 285 | PECAM1 | 5175 | X | 0.7 | | | L, V |
| 286 | PECAM1 | 5175 | X | 0.7 | | | L, V |
| 287 | KLF1 | 10661 | X | 0.7 | D+ | | V, Q |
| 288 | GLUL | 2752 | X | 0.7 | V+ D+ | | |
| 289 | TNXB | 7148 | X | 0.7 | | | L |
| 290 | TNXB | 7148 | X | 0.69 | | | L |
| 291 | BLVRB | 645 | X | 0.69 | V+ | | F |
| 292 | TNXB | 7148 | X | 0.69 | | | L |
| 293 | NFIA | 4774 | X | 0.68 | | | |
| 294 | LY86 | 9450 | X | 0.68 | D+ | | T, Q |
| 295 | GYPB; GYPE | 2994 /// 2996 | X | 0.68 | D+ | | F |
| 296 | FY | 2532 | X | 0.67 | | | |
| 297 | KCNH2 | 3757 | X | 0.67 | | | F |
| 298 | ARID5B | 84159 | X | 0.67 | | | P |
| 299 | | | X | 0.67 | | | |
| 300 | EPOR | 2057 | X | 0.67 | V+ | | F |
| 301 | BIN1 | 274 | X | 0.67 | | | Q |
| 302 | NFIX | 4784 | X | 0.67 | | | V |
| 303 | KEL | 3792 | X | 0.66 | | | |
| 304 | ANK1 | 286 | X | 0.66 | | | F |
| 305 | MYL4 | 4635 | X | 0.66 | | | F |
| 306 | LXN | 56925 | X | 0.66 | | | |
| 307 | LEPR | 3953 | X | 0.66 | | | |
| 308 | NCF4 | 4689 | X | 0.65 | | | |
| 309 | TAL1 | 6886 | X | 0.65 | | | E, V |
| 310 | ANK1 | 286 | X | 0.65 | | | F |
| 311 | RIN3 | 79890 | X | 0.65 | V+ | | |
| 312 | GAS2L1 | 10634 | X | 0.65 | | | |
| 313 | UBADC1 | 10422 | X | 0.64 | | | P, Q |
| 314 | RGS10 | 6001 | X | 0.64 | | | |
| 315 | CAT | 847 | X | 0.64 | D+ | | V |
| 316 | AQP1 | 358 | X | 0.64 | V+ | | |
| 317 | MYL4 | 4635 | X | 0.64 | D+ | | F |
| 318 | TPM1 | 7168 | X | 0.63 | | | |
| 319 | MYH10 | 4628 | X | 0.63 | | | |
| 320 | GLRX | 2745 | X | 0.62 | | V+ | K, T |
| 321 | TSPAN32 | 10077 | X | 0.62 | | | |
| 322 | CTBP2 | 1488 | X | 0.61 | V+ | | |
| 323 | WNK1 | 65125 | X | 0.61 | V+ | | T |
| 324 | SCAMP5 | 192683 | X | 0.61 | | V+ | T |
| 325 | MOSC2 | 54996 | X | 0.61 | | | M, Q |
| 326 | DKFZp761P1121 | 128989 | X | 0.61 | | | |
| 327 | SEC14L4 | 284904 | X | 0.61 | | | |
| 328 | OACT2 | 129642 | X | 0.6 | | | |
| 329 | FOLR1 | 2348 | X | 0.6 | | | |
| 330 | GNG7 | 2788 | X | 0.58 | | | |
| 331 | DEFA4 | 1669 | X | 0.58 | | | |
| 332 | RECQL5 | 643008 | X | 0.58 | | | |
| 333 | 8-Mar | 220972 | X | 0.58 | D+ | | P |
| 334 | MYL4 | 4635 | X | 0.57 | | | F |

TABLE 1-continued

Short Term and Long Term Survival Markers

| # | Name | ID | | Value | | | |
|---|---|---|---|---|---|---|---|
| 335 | PCAF | 8850 | X | 0.57 | D+ | D+ | V, K |
| 336 | MYL4 | 4635 | X | 0.57 | D+ | | F |
| 337 | NFATC1 | 4772 | X | 0.57 | | | T, S |
| 338 | FLJ22386 | 79641 | X | 0.57 | | | |
| 339 | C5orf4 | 10826 | X | 0.57 | | | V |
| 340 | C10orf54 | 64115 | X | 0.56 | V+ | V+ | |
| 341 | GYPC | 2995 | X | 0.55 | | | |
| 342 | HEBP1 | 50865 | X | 0.55 | | | F |
| 343 | NME4 | 4833 | X | 0.55 | | V+ | R, Q |
| 344 | SLC2A1 | 6513 | X | 0.54 | | | F, V |
| 345 | C1QDC1 | 65981 | X | 0.54 | | | |
| 346 | SNCA | 6622 | X | 0.54 | V+ | | |
| 347 | KIAA1727 | 85462 | X | 0.54 | V+ | | |
| 348 | TRIM10 | 10107 | X | 0.53 | | | P |
| 349 | CTBP2 | 1488 | X | 0.53 | V+ | | |
| 350 | SLC12A7 | 10723 | X | 0.53 | V+ | | |
| 351 | SLC11A2 | 4891 | X | 0.53 | | | |
| 352 | AMT | 275 | X | 0.52 | | | K, R |
| 353 | CSNK1A1 | 1452 | X | 0.52 | | | G, V |
| 354 | UROD | 7389 | X | 0.52 | | | M, Q |
| 355 | PQLC1 | 80148 | X | 0.52 | | | |
| 356 | RXRA | 6256 | X | 0.52 | V+ | | V |
| 357 | SLC11A2 | 4891 | X | 0.52 | V+ | | |
| 358 | CAPN3 | 825 | X | 0.52 | V+ | V+ | |
| 359 | MXD4 | 10608 | X | 0.52 | | | V |
| 360 | ZNF710 | 374655 | X | 0.52 | | | |
| 361 | CTSE | 1510 | X | 0.51 | | | |
| 362 | GNG7 | 2788 | X | 0.51 | | D+ | |
| 363 | ECHDC2 | 55268 | X | 0.51 | | | |
| 364 | CYBRD1 | 79901 | X | 0.5 | V+ | | R |
| 365 | AK1 | 203 | X | 0.49 | V+ | | K |
| 366 | STX7 | 8417 | X | 0.48 | | | T |
| 367 | OACT2 | | X | 0.48 | | | |
| 368 | SLC25A37 | 51312 | X | 0.48 | | | R |
| 369 | RANBP10 | 57610 | X | 0.48 | V+ | | |
| 370 | ABCC5 | 10057 | X | 0.48 | | | |
| 371 | NR3C1 | 2908 | X | 0.47 | | | G |
| 372 | MAN2C1 | 4123 | X | 0.47 | | | |
| 373 | ZNF710 | 374655 | X | 0.47 | | | |
| 374 | TPM1 | 7168 | X | 0.47 | V+ | | |
| 375 | GYPA | 2993 | X | 0.47 | | | F |
| 376 | ABCB6; ATG9A | 10058 /// 79065 | X | 0.45 | | | |
| 377 | AKR1C1 | 1645 | X | 0.45 | V+ | | V |
| 378 | USP12 | 219333 | X | 0.45 | V+ | | P, K |
| 379 | SERPINB1 | 1992 | X | 0.45 | V+ | | K |
| 380 | LDB1 | 8861 | X | 0.44 | | | |
| 381 | PINK1 | 65018 | X | 0.43 | V+ | | K |
| 382 | TPT1 | 7178 | X | 0.42 | | | |
| 383 | CPT1A | 1374 | X | 0.42 | | | R |
| 384 | CTNNA1 | 1495 | X | 0.41 | | | L, V |
| 385 | B2M | 567 | X | 0.41 | | V+ | M, V |
| 386 | CTNNA1 | 1495 | X | 0.4 | | | V |
| 387 | LOC51035 | 51035 | X | 0.4 | | D+ | K |
| 388 | CAST | 831 | X | 0.4 | D+ | D+ | |
| 389 | HECA | 51696 | X | 0.4 | D+ | V+ D+ | |
| 390 | UBE2B | 7320 | X | 0.4 | | | P |
| 391 | AKR1C1 | 1645 | X | 0.38 | | | V |
| 392 | USP15 | 9958 | X | 0.38 | V+ | V+ | P |
| 393 | SLIT1 | 6585 | X | 0.38 | V+ | V+ | |
| 394 | WDR23 | 80344 | X | 0.37 | | D+ | |
| 395 | FAM82C | 55177 | X | 0.36 | | | |
| 396 | CAST | 831 | X | 0.36 | D+ | D+ | |
| 397 | EEF1A1 | 1915 | X | 0.35 | | | T, V |
| 398 | TSPAN17 | 26262 | X | 0.35 | | | |
| 399 | EEF1A1 | 1915 | X | 0.33 | | | T, J |
| 400 | HDAC3 | 8841 | X | 0.33 | | | M |
| 401 | EEF1A1 | 1915 | X | 0.3 | | | T, J |
| 402 | FAM65A | 79567 | X | 0.25 | V+ | | |
| 403 | JMJD1B | 51780 | X | 0.21 | | | |

TABLE 2

| | | | Rep Public | |
|---|---|---|---|---|
| No. | ProbeSet ID | Chip | ID | Title |
| 1 | 204944_at | HG-U133A | NM_002841 | protein tyrosine phosphatase, receptor type, G |
| 2 | 210394_x_at | HG-U133A | | synovial sarcoma, X breakpoint 4 |
| 3 | 225105_at | HG-U133B | BF969397 | hypothetical protein |
| 4 | 204430_s_at | | | solute carrier family 2 (facilitated glucose/fructose transporter), member 5 |
| 5 | 227126_at | HG-U133A | NM_002841 | protein tyrosine phosphatase, receptor type, G |
| 6 | 221601_s_at | HG-U133A | AI084226 | Fas apoptotic inhibitory molecule 3 |
| 7 | 206626_x_at | HG-U133A | BC001003 | synovial sarcoma, X breakpoint 1 |
| 8 | 211425_x_at | HG-U133A | | synovial sarcoma, X breakpoint 4 |
| 9 | 210497_x_at | HG-U133A | BC002818 | synovial sarcoma, X breakpoint 2 |
| 10 | 211674_x_at | HG-U133A | AF038567 | cancer/testis antigen 1B /// cancer/testis antigen 1A |
| 11 | 218695_at | HG-U133A | NM_019037 | exosome component 4 |
| 12 | 216471_x_at | HG-U133A | X79200 | synovial sarcoma, X breakpoint 2 |
| 13 | 203828_s_at | HG-U133A | NM_004221 | interleukin 32 |
| 14 | 226219_at | HG-U133B | AW575123 | Rho GTPase activating protein 30 |
| 15 | 232231_at | | | runt-related transcription factor 2 |
| 16 | 225548_at | | | shroom |
| 17 | 205718_at | | | integrin, beta 7 |
| 18 | 221602_s_at | HG-U133A | AF057557 | Fas apoptotic inhibitory molecule 3 |
| 19 | 220565_at | | | chemokine (C-C motif) receptor 10 |
| 20 | 209942_x_at | | | melanoma antigen family A, 3 |
| 21 | 218529_at | | | CD320 antigen |
| 22 | 207666_x_at | HG-U133A | | synovial sarcoma, X breakpoint 3 |
| 23 | 212281_s_at | HG-U133A | BF038366 | hypothetical protein MAC30 |
| 24 | 223743_s_at | | | mitochondrial ribosomal protein L4 |
| 25 | 241224_x_at | HG-U133B | AA770014 | Down syndrome critical region gene 8 |
| 26 | 225213_at | HG-U133B | AW300598 | T-cell activation protein phosphatase 2C |
| 27 | 223625_at | | | down-regulated by Ctnnb1, a |
| 28 | 227212_s_at | HG-U133B | | PHD finger protein 19 |
| 29 | 214612_x_at | | | melanoma antigen family A, 6 |
| 30 | 212680_x_at | | | protein phosphatase 1, regulatory (inhibitor) subunit 14B |
| 31 | 224579_at | HG-U133B | BF247552 | solute carrier family 38, member 1 |
| 32 | 225400_at | HG-U133B | | chromosome 1 open reading frame 19 |
| 33 | 218826_at | HG-U133A | NM_017515 | solute carrier family 35, member F2 |
| 34 | 206640_x_at | | | G antigen 2 /// G antigen 4 /// G antigen 5 /// G antigen 6 /// G antigen 7 /// G antigen 7B |
| 35 | 229826_at | | | similar to CG32736-PA |
| 36 | 212750_at | | | protein phosphatase 1, regulatory (inhibitor) subunit 16B |
| 37 | 220448_at | | | potassium channel, subfamily K, member 12 |
| 38 | 208416_s_at | HG-U133A | NM_000347 | spectrin, beta, erythrocytic (includes spherocytosis, clinical type I) |
| 39 | 205592_at | HG-U133A | X77737 | solute carrier family 4, anion exchanger, member 1 (erythrocyte membrane protein band 3, Diego blood group) |
| 40 | 223670_s_at | HG-U133B | AF322875 | hemogen |
| 41 | 210746_s_at | HG-U133A | M30646 | erythrocyte membrane protein band 4.2 |
| 42 | 201131_s_at | | | cadherin 1, type 1, E-cadherin (epithelial) |
| 43 | 227654_at | HG-U133B | AI056877 | similar to KIAA0386 |
| 44 | 211820_x_at | HG-U133A | U00179 | glycophorin A (includes MN blood group) |
| 45 | 205838_at | | | glycophorin A (includes MN blood group) |
| 46 | 208335_s_at | HG-U133A | NM_002036 | Duffy blood group |
| 47 | 209930_s_at | HG-U133A | L13974 | nuclear factor (erythroid-derived 2), 45 kDa |
| 48 | 209301_at | HG-U133A | M36532 | carbonic anhydrase II |
| 49 | 215811_at | HG-U133A | AF238870 | synuclein, alpha (non A4 component of amyloid precursor) |
| 50 | 205268_s_at | HG-U133A | NM_017488 | adducin 2 (beta) |
| 51 | 232232_s_at | HG-U133B | | solute carrier family 22 (organic cation transporter), member 16 |
| 52 | 223669_at | HG-U133B | AF130060 | hemogen |
| 53 | 202219_at | HG-U133A | NM_005629 | solute carrier family 6 (neurotransmitter transporter, creatine), member 8 |
| 54 | 205950_s_at | HG-U133A | NM_001738 | carbonic anhydrase I |
| 55 | 205837_s_at | HG-U133A | BC005319 | glycophorin A (includes MN blood group) |
| 56 | 211821_x_at | HG-U133A | U00178 | glycophorin A (includes MN blood group) |
| 57 | 210395_x_at | HG-U133A | AF116676 | myosin, light polypeptide 4, alkali |
| 58 | 219672_at | HG-U133A | NM_016633 | erythroid associated factor |
| 59 | 206488_s_at | HG-U133A | NM_000072 | CD36 antigen (collagen type I receptor, thrombospondin receptor) |
| 60 | 215819_s_at | HG-U133A | N53959 | Rhesus blood group, CcEe antigens /// Rhesus blood group, D antigen |
| 61 | 205671_s_at | | | major histocompatibility complex, class II, DO beta |

TABLE 2-continued

Short Term and Long Term Survival Markers

| | | | | |
|---|---|---|---|---|
| 62 | 210504_at | HG-U133A | U65404 | Kruppel-like factor 1 (erythroid) |
| 63 | 216054_x_at | HG-U133A | X58851 | myosin, light polypeptide 4, alkali |
| 64 | 236981_at | HG-U133B | AI242058 | Clone DNA57836 GLPG464 (UNQ464) mRNA, complete cds |
| 65 | 226751_at | HG-U133B | | chromosome 2 open reading frame 32 |
| 66 | 235916_at | HG-U133B | | yippee-like 4 (*Drosophila*) |
| 67 | 204249_s_at | HG-U133A | NM_005574 | LIM domain only 2 (rhombotin-like 1) |
| 68 | 205033_s_at | | | defensin, alpha 1 /// defensin, alpha 3, neutrophil-specific |
| 69 | 206937_at | HG-U133A | NM_003126 | spectrin, alpha, erythrocytic 1 (elliptocytosis 2) |
| 70 | 242197_x_at | HG-U133B | | CD36 antigen (collagen type I receptor, thrombospondin receptor) |
| 71 | 210036_s_at | HG-U133A | AB044806 | potassium voltage-gated channel, subfamily H (eag-related), member 2 |
| 72 | 210215_at | HG-U133A | AF067864 | transferrin receptor 2 |
| 73 | 208352_x_at | HG-U133A | NM_020479 | ankyrin 1, erythrocytic |
| 74 | 210986_s_at | HG-U133A | Z24727 | tropomyosin 1 (alpha) |
| 75 | 217865_at | | | ring finger protein 130 |
| 76 | 37986_at | HG-U133A | M60459 | erythropoietin receptor |
| 77 | 200934_at | | | DEK oncogene (DNA binding) |
| 78 | 210430_x_at | HG-U133A | L08429 | Rhesus blood group, D antigen |
| 79 | 214464_at | HG-U133A | NM_003607 | CDC42 binding protein kinase alpha (DMPK-like) |
| 80 | 206093_x_at | HG-U133A | NM_007116 | tenascin XB |
| 81 | 203662_s_at | HG-U133A | | tropomodulin 1 |
| 82 | 210586_x_at | HG-U133A | AF312679 | Rhesus blood group, D antigen |
| 83 | 209555_s_at | HG-U133A | M98399 | CD36 antigen (collagen type I receptor, thrombospondin receptor) |
| 84 | 215449_at | HG-U133A | AI052224 | benzodiazapine receptor (peripheral)-like 1 |
| 85 | 202201_at | HG-U133A | NM_000713 | biliverdin reductase B (flavin reductase (NADPH)) |
| 86 | 206283_s_at | HG-U133A | NM_003189 | T-cell acute lymphocytic leukemia 1 |
| 87 | 221627_at | HG-U133A | AF220123 | tripartite motif-containing 10 |
| 88 | 206145_at | HG-U133A | NM_000324 | Rhesus blood group-associated glycoprotein |
| 89 | 206077_at | HG-U133A | NM_000420 | Kell blood group |
| 90 | 205390_s_at | HG-U133A | NM_000037 | ankyrin 1, erythrocytic |
| 91 | 205391_x_at | HG-U133A | M28880 | ankyrin 1, erythrocytic |
| 92 | 208886_at | HG-U133A | BC000145 | H1 histone family, member 0 |
| 93 | 237403_at | HG-U133B | AI097490 | growth factor independent 1B (potential regulator of CDKN1A, translocated in CML) |
| 94 | 225061_at | HG-U133B | N45231 | DnaJ (Hsp40) homolog, subfamily A, member 4 |
| 95 | 216333_x_at | HG-U133A | | tenascin XB |
| 96 | 208353_x_at | HG-U133A | NM_020480 | ankyrin 1, erythrocytic |
| 97 | 213451_x_at | HG-U133A | | tenascin XB |
| 98 | 207087_x_at | HG-U133A | NM_020478 | ankyrin 1, erythrocytic |
| 99 | 209160_at | HG-U133A | AB018580 | aldo-keto reductase family 1, member C3 (3-alpha hydroxysteroid dehydrogenase, type II) |
| 100 | 205262_at | HG-U133A | NM_000238 | potassium voltage-gated channel, subfamily H (eag-related), member 2 |

| Gene No. | Gene Symbol | Entrez Gene ID | Short Term | Long Term | SuperPC 025 + 040 | Biol Cat |
|---|---|---|---|---|---|---|
| 1 | PTPRG | 5793 | X | | 3.05 | V |
| 2 | SSX4 | 6759 | X | | 2.96 | D |
| 3 | LOC387882 | 387882 | X | | 2.94 | |
| 4 | SLC2A5 | 6518 | X | | 2.90 | |
| 5 | PTPRG | 5793 | X | | 2.87 | |
| 6 | FAIM3 | 9214 | X | | 2.85 | G, E |
| 7 | SSX1 | 6756 | X | | 2.82 | D |
| 8 | SSX4 | 6759 | X | | 2.80 | D |
| 9 | SSX2 | 6757 | X | | 2.76 | D |
| 10 | CTAG1B | 1485 | X | | 2.66 | D |
| 11 | EXOSC4 | 54512 | X | | 2.63 | T |
| 12 | SSX2 | 6757 | X | | 2.61 | D |
| 13 | IL32 | 9235 | X | | 2.58 | L, E |
| 14 | ARHGAP30 | 257106 | X | | 2.57 | |
| 15 | RUNX2 | 860 | X | | 2.55 | |
| 16 | SHRM | 57619 | X | | 2.52 | |
| 17 | ITGB7 | 3695 | X | | 2.52 | L |
| 18 | FAIM3 | 9214 | X | | 2.51 | G, E |
| 19 | CCR10 | 2826 | X | | 2.50 | |
| 20 | MAGEA3 | 4102 | X | | 2.48 | D |
| 21 | CD320 | 51293 | X | | 2.47 | L, I |
| 22 | SSX3 | 10214 | X | | 2.46 | D |

TABLE 2-continued

Short Term and Long Term Survival Markers

| | | | | | | |
|---|---|---|---|---|---|---|
| 23 | MAC30 | 27346 | X | | 2.45 | |
| 24 | MRPL4 | 51073 | X | | 2.45 | R |
| 25 | DSCR8 | 84677 | X | | 2.42 | |
| 26 | TA-PP2C | 160760 | X | | 2.40 | |
| 27 | DRCTNNB1A | 84668 | X | | 2.39 | |
| 28 | PHF19 | 26147 | X | | 2.37 | K |
| 29 | MAGEA6 | 4105 | X | | 2.34 | D |
| 30 | PPP1R14B | 26472 | X | | 2.34 | |
| 31 | SLC38A1 | 81539 | X | | 2.33 | T, V |
| 32 | C1orf19 | 116461 | X | | 2.33 | Q |
| 33 | SLC35F2 | 54733 | X | | 2.32 | U |
| 34 | GAGE2 | 2574 | X | | 2.32 | D |
| 35 | LOC440957 | 440957 | X | | 2.31 | |
| 36 | PPP1R16B | 26051 | X | | 2.29 | |
| 37 | KCNK12 | 56660 | X | | 2.28 | |
| 38 | SPTB | 6710 | | X | −2.29 | F |
| 39 | SLC4A1 | 6521 | | X | −2.30 | F |
| 40 | HEMGN | 55363 | | X | −2.30 | F, Q |
| 41 | EPB42 | 2038 | | X | −2.35 | |
| 42 | CDH1 | 999 | | X | −2.35 | L, K |
| 43 | LOC200230 | 200230 | | X | −2.35 | |
| 44 | GYPA | 2993 | | X | −2.36 | F |
| 45 | GYPA | 2993 | | X | −2.36 | F |
| 46 | FY | 2532 | | X | −2.37 | |
| 47 | NFE2 | 4778 | | X | −2.37 | F |
| 48 | CA2 | 760 | | X | −2.37 | |
| 49 | SNCA | 6622 | | X | −2.38 | |
| 50 | ADD2 | 119 | | X | −2.38 | |
| 51 | SLC22A16 | 85413 | | X | −2.39 | |
| 52 | HEMGN | 55363 | | X | −2.39 | F, Q |
| 53 | SLC6A8 | 6535 | | X | −2.40 | |
| 54 | CA1 | 759 | | X | −2.40 | |
| 55 | GYPA | 2993 | | X | −2.42 | F |
| 56 | GYPA | 2993 | | X | −2.42 | F |
| 57 | MYL4 | 4635 | | X | −2.43 | F |
| 58 | ERAF | 51327 | | X | −2.44 | F |
| 59 | CD36 | 948 | | X | −1.73 | L, F |
| 60 | RHCE | 6006 | | X | −2.47 | F |
| 61 | HLA-DOB | 3112 | | X | −2.47 | |
| 62 | KLF1 | 10661 | | X | −2.48 | V, Q |
| 63 | MYL4 | 4635 | | X | −2.49 | F |
| 64 | | | | X | −2.49 | |
| 65 | C2orf32 | 25927 | | X | −2.50 | |
| 66 | YPEL4 | 219539 | | X | −2.52 | |
| 67 | LMO2 | 4005 | | X | −2.52 | T |
| 68 | DEFA1 | 1667 | | X | −2.53 | |
| 69 | SPTA1 | 6708 | | X | −2.53 | F |
| 70 | CD36 | 948 | | X | −2.54 | L, F |
| 71 | KCNH2 | 3757 | | X | −2.55 | F |
| 72 | TFR2 | 7036 | | X | −2.55 | |
| 73 | ANK1 | 286 | | X | −2.56 | F |
| 74 | TPM1 | 7168 | | X | −2.57 | |
| 75 | RNF130 | 55819 | | X | −2.57 | P |
| 76 | EPOR | 2057 | | X | −2.61 | F |
| 77 | DEK | 7913 | | X | −2.61 | E, B, G |
| 78 | RHD | 6007 | | X | −2.61 | F |
| 79 | CDC42BPA | 8476 | | X | −2.62 | K |
| 80 | TNXB | 7148 | | X | −2.64 | L |
| 81 | TMOD1 | 7111 | | X | −2.65 | F |
| 82 | RHD | 6007 | | X | −2.67 | F |
| 83 | CD36 | 948 | | X | −2.68 | F, L |
| 84 | BZRPL1 | 222642 | | X | −2.69 | |
| 85 | BLVRB | 645 | | X | −2.69 | F |
| 86 | TAL1 | 6886 | | X | −2.69 | E, V |
| 87 | TRIM10 | 10107 | | X | −2.70 | K, T |
| 88 | RHAG | 6005 | | X | −2.72 | F, Q |
| 89 | KEL | 3792 | | X | −2.74 | |
| 90 | ANK1 | 286 | | X | −2.77 | F, U |
| 91 | ANK1 | 286 | | X | −2.78 | F |
| 92 | H1F0 | 3005 | | X | −2.79 | P, Q |
| 93 | GFI1B | 8328 | | X | −2.82 | G |
| 94 | DNAJA4 | 55466 | | X | −2.88 | K |
| 95 | TNXB | 7148 | | X | −2.88 | L |
| 96 | ANK1 | 286 | | X | −2.91 | F |
| 97 | TNXB | 7148 | | X | −2.96 | L |
| 98 | ANK1 | 286 | | X | −2.97 | F |

TABLE 2-continued

Short Term and Long Term Survival Markers

| 99 | AKR1C3 | 8644 | X | −3.07 | V |
| 100 | KCNH2 | 3757 | X | −3.22 | F |

Various algorithms are currently available that can be used to classify patient samples using a given set of features. Therefore, the combination of markers selected through the features selection process may be used in any of the available algorithms in order to derive a prediction equation for patient survival.

The Linear Predictive Score was implemented as described by Wright et al., "A gene-expression based method to diagnose clinically distinct groups of diffuse large B cell lymphoma." PNAS 100(17):9991-9996 (2003), the contents of which are incorporated herein by reference. As described by Wright et al., the LPS score for a vector X is computed as:

$$LPS(X) = \sum_j a_j X_j$$

where $X_j$ represents the log expression value for the $j^{th}$ feature in the set, and $a_j$ is a scaling factor representing the degree to which the $j^{th}$ feature is associated with the outcome to be predicted. As in Wright et al., we used the t-statistics of the features for the scaling factors. Given the LPS score, the likelihood that a sample is in the first of the two classes is determined using this formula:

$$P(X \in S_1) = \frac{\phi(LPS(X); \hat{\mu}_1, \hat{\sigma}_1^2)}{\phi(LPS(X); \hat{\mu}_1, \hat{\sigma}_1^2) + \phi(LPS(X); \hat{\mu}_2, \hat{\sigma}_2^2)},$$

where $\phi(x; \mu, \text{or } \sigma^2)$ represents the normal density function with mean $\mu$ and variance $\sigma^2$, and $\hat{\mu}_1$, $\hat{\sigma}_1^2$, $\hat{\mu}_2$ and $\hat{\sigma}_2^2$ are the observed means and variances of the LPS scores for category 1 and category 2. In our case, for example, category 1 would be responders, and category 2 would be non-responders. Then the prediction for a new sample would be that it would be in the first class with probability $P(X \in S_1)$ and in the second class with probability $P(X \in S_2)=1-P(X \in S_1)$.

The K-nearest neighbor classification method computes the similarity between a query profile and each of the profiles in the training set [Introduction to Machine Learning by Ethem ALPAYDIN, The MIT Press, October 2004, ISBN 0-262-01211-1]. The k most similar profiles are selected, and a vote is taken amongst their class labels to determine the prediction for the query profile. Here, we used k=1.

Feature Selection

Feature selection is the process of determining a subset of the thousands of available features in the dataset, resulting in a combination of features that form a marker set or model, to classify patients by treatment outcome. There are many approaches to selecting features. Here we report two approaches to generate example marker sets: (1) top N most significant features, and (2) a standard feature selection method, sequential forward feature selection (See, Dash and Liu, "Feature Selection for Classification," Intelligent Data Analysis 1:131-156, 1997).

Discussion of Results from Short Term and Long Term Predictive Marker Selection

Sample Collection and Genomic Data Generation in Multi-center Clinical Trials

The Phase 2 and Phase 3 clinical trials of bortezomib for the treatment of multiple myeloma included a research component to investigate the feasibility of pharmacogenomics in a prospective setting. 89 centers (from 12 different countries) provided tumor samples for research. A pretreatment bone marrow aspirate sample was collected during routine screening procedures. The percentage of tumor in these aspirates is highly variable. In an effort to increase tumor content to at least 60-80%, a level consistent with prior genomic studies of cancer biology and outcome (Zhan: Blood, 108:2020-2028, 2006; Dave S S, Wright G, Tan B, et al: Prediction of survival in follicular lymphoma based on molecular features of tumor-infiltrating immune cells. N Engl J Med 351:2159-2169, 2004; Valk P J, Verhaak R G, Beijen M A, et al: Prognostically useful gene-expression profiles in acute myeloid leukemia. N Engl J Med 350:1617-1628, 2004), all samples were subjected to an enrichment procedure (see methods). Fluorescence cell sorting analysis (FACS) of pre- and post-enrichment samples demonstrated that the enrichment could yield samples of 80-90% tumor cells (FIG. 1). FACS analyses were not practical at all participating centers. Therefore, we assessed sample purity via analysis of a myeloma purity score derived from the microarray data (see methods) and samples with low tumor cell purity were excluded from further analyses (FIG. 1B). Sample attrition was observed at each step in the process of generating gene expression data. Approximately 60% of samples exhibited RNA quantity and quality adequate for hybridization. Of these samples, ~85% generated high quality microarray data and then 85% passed the assessment of tumor cell enrichment described above. These results were generally consistent across the different clinical trials.

For each trial, we examined a series of clinical and prognostic variables to insure that the subset of patients with genomic data were representative of the general trial population. No bias was observed with regard to age, gender, or myeloma isotype. For some of these trials the survival values of the genomics subset were indicative of a worse outcome. Although serum albumin and serum β-2 microglobulin were elevated in the genomics subset of the 025 trial this was not observed in the other trial data. The genomics subset of each trial, however, did exhibit a higher baseline tumor burden in the bone marrow aspirate, indicating that successful sampling is likely related to the extent of marrow disease. The data suggests that genomic subsets are reasonable representations of the study populations as a whole, although there is an overrepresentation of patients with high tumor burden.

Comparison of Dataset with Published Myeloma Biology

Figure 2A:
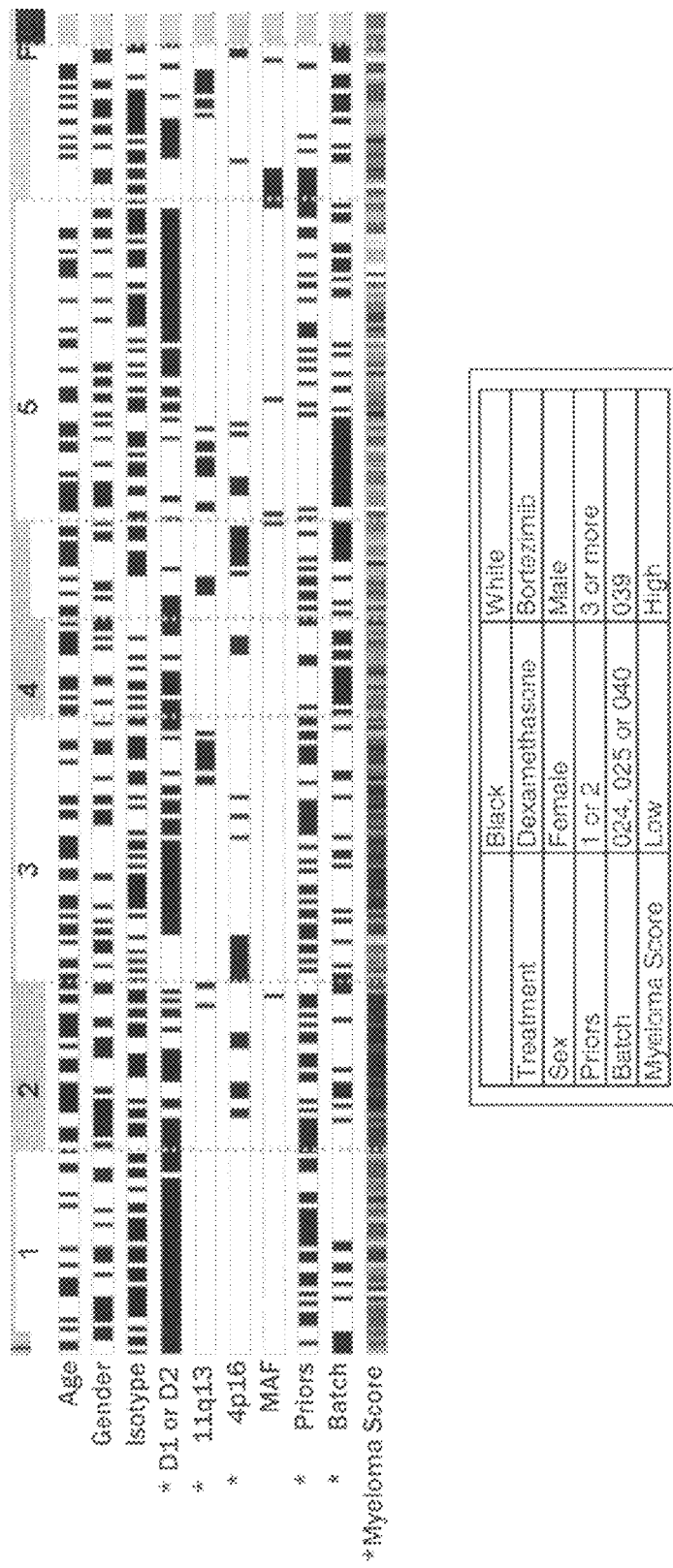
FIG. 2A) is a table representing sample relationships which are influenced by clinical and gene-expression characteristics. 264 myeloma patient samples and 6 normal plasma cell control (PC) samples were subject to unsupervised hierarchical clustering based upon 9174 differentially expressed probesets. Highly related branches (labeled Groups 1-5) were identified by setting a fixed similarity metric (GeneMaths software) and requiring at least 12 samples for membership; unlabelled samples are comprised of various smaller groups. Patient attributes are encoded above the table. Attributes with non-random distribution (p<0.05) are marked by astericks (*). The black and white color code is described in the table.

Our genomics approach differs from that of prior myeloma studies (Zhan F, Hardin J, Kordsmeier B, et al: Global gene expression profiling of multiple myeloma, monoclonal gammopathy of undetermined significance, and normal bone marrow plasma cells. Blood 99:1745-1757, 2002; Claudio J O, Masih-Khan E, Tang H, et al: A molecular compendium of genes expressed in multiple myeloma. Blood 100:2175-2186, 2002; Zhan: Blood 108:2020-2028, 2006; Hurt E M, Wiestner A, Rosenwald A, et al: Overexpression of c-maf is a frequent oncogenic event in multiple myeloma that promotes proliferation and pathological interactions with bone marrow stroma. (Cancer Cell 5:191-199, 2004) in that samples were collected at multiple sites and were subjected to a negative-selection procedure to enrich for tumor cells. Therefore, we closely examined how the data might have been influenced by demographic, clinical, and technical parameters, using unsupervised hierarchical clustering. FIG. 2A summarizes 264 myeloma patient samples and 6 normal plasma cell control (PC) samples. Patients with different age, gender and myeloma isotype were randomly distributed (FIG. 2A) across these groups. Further, there was no significant clustering of samples that originated at the same clinical center. However, a non-random distribution was observed for clinical study, number of prior therapies, array hybridization batch, myeloma purity score and, consistent with a recent report (Zhan: Blood, 108:2020-2028, 2006), for myeloma TC subtype. Several of these factors are inter-related; most notably, the 039 study patients had significantly less prior therapy and were hybridized in one batch, making it difficult to discern if one or both of these factors influence the clustering. Because the 025 study patients exhibit a varied number of prior therapies, we asked whether the distribution of these samples is dependent upon the extent of their prior therapy. In fact, the 025 patients in groups 1-3 had fewer lines of prior therapy (mean=3.7) than those in branches 4-5 (mean=5.1) (P=0.053), suggesting that the distribution of samples is at least in part influenced by the extent of prior therapy.

The 039 randomized trial demonstrated superior survival in the bortezomib arm (30 vs 24 months for dex, P=0.027) (22 month median follow-up, 44% events occurred) (Richardson ASH 2005). A significant survival advantage was also observed at a pre-planned interim analysis, at which time all patients were permitted to receive bortezomib and 62% of the Dex arm patients subsequently received single agent bortezomib. Analysis of the gene expression patterns exemplified among the probesets in the survival classifier (Table 2) reveals several features in common with previously reported studies of myeloma (FIG. 2B). These probesets cluster to genes in pathways whose changes are associated with myeloma.

We used gene expression data from 025+040 patients to develop a survival classifier (Bair E, Tibshirani R: Semi-supervised methods to predict patient survival from gene expression data. PLoS Biol 2:E108, 2004) that was then tested with 039 patient data. As shown in FIG. 3A this gene expression classifier stratified the 039 bortezomib patients into high and low risk groups that were significantly associated with their risk of death (P<0.000004). The classifier also effectively stratified the patients enrolled in the 039 dexamethasone arm (P<0.0012, FIG. 3B). It is possible this survival classifier and the underlying probesets may be prognostic of survival independent of the specific therapy administered. However, there may be some specificity for bortezomib (as observed with the response classifier) that is masked by the subsequent use of bortezomib in the majority of patients enrolled in the Dex arm.

Figures 3C, 3D:
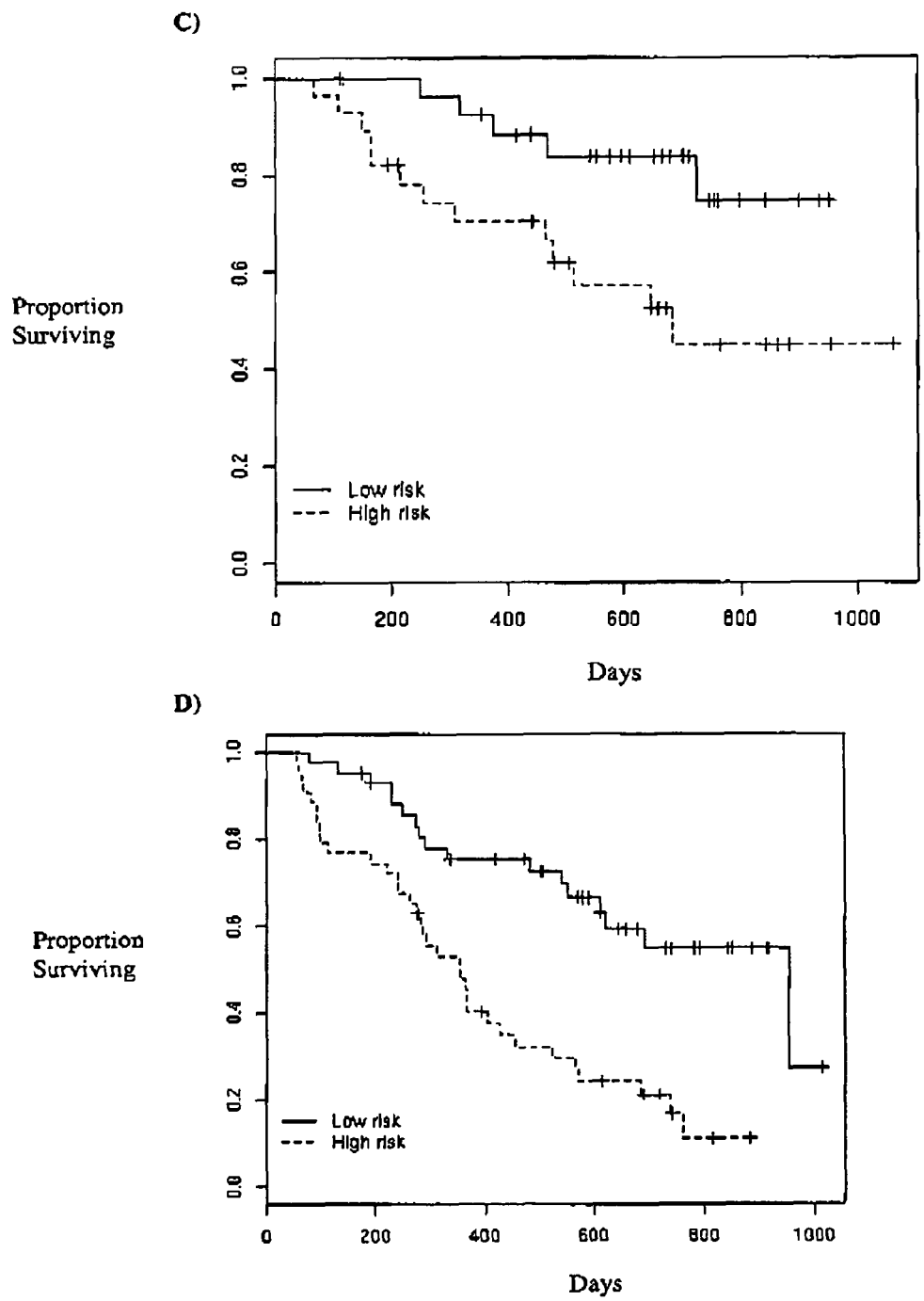

In order to determine if the pre-treatment gene expression provides data that isn't already captured by prognostic clinical variables, we assessed the survival of patients predicted to be high or low risk by the International Staging System. (Greipp P R, San Miguel J, Durie B G, et al: International Staging System (ISS) for multiple myeloma. J Clin Oncol 23:3412-3420, 2005). The risk groups identified by this validated staging system are relevant for various myeloma therapies and also discern high/low risk in the 039 trial patients (data not shown). As shown in FIGS. 3C and 3D, the gene expression classifier enables significant further stratification in patients identified as low (ISS=1) and high (ISS=2 or 3) risk respectively, indicating that the clinical staging and genomic information are not redundant but are likely to be complimentary.

The probesets comprising this survival classifier (Table 2) do not overlap with the response classifier. This is not surprising, as the survival and response endpoints are only partially related. Overexpression of adhesion related genes (CDH1, CD36, TNXB) are correlated with longer survival, and cancer antigens (SSX4, SSX2) are correlated with shorter survival, suggesting there may be biological consistencies.

We note that the survival classifier described here captures outcome-related information that is distinct from clinical prognostic variables (e.g. serum albumin and β-2M) as demonstrated by the significant capacity to discern risk groups within the high and low-risk ISS groups (FIG. 3). Studies in lymphoma have drawn similar conclusions (Rosenwald N. Engl. J. Med. 346:1937-47 (2002).

The present invention is not to be limited in scope by the specific embodiments described that are intended as illustrations of aspects of the invention. Functionally equivalent methods and components are within the scope of the invention, in addition to those shown and described herein and will become apparent to those skilled in the art from the foregoing description, using no more than routine experimentation. Such equivalents are intended to be encompassed by the following claims.

All references cited herein, including journal articles, patents, AFFYMETRIX® Inc. probeset sequence files, and databases are expressly incorporated by reference.

What is claimed is:

1. A method of treating a cancer patient with bortezomib comprising:
    a) measuring in a sample from the cancer patient, wherein the cancer patient has multiple myeloma, wherein the sample is enriched for tumor cells, the level of expression of at least ten predictive markers in a predictive marker set selected from the predictive markers identified in rows 225 to 403 of Table 1, wherein the predictive marker set comprises no more than 150 markers;
    b) comparing the levels of expression of the markers to reference expression levels of each of the markers and detecting increased expression of 50% of the markers of the predictive set in the cancer patient sample as compared to the reference expression levels; and
    c) treating the cancer patient with bortezomib.

2. The method of claim 1, wherein the predictive markers are annotated into a biological category, wherein the biological category is oncogenic signaling.

3. The method of claim 2, wherein the oncogenic signaling category comprises marker number 381.

4. The method of claim 1, wherein 80% of long term survivors survive at least 12 months after receiving the first dose of treatment.

5. The method of claim 1, wherein each predictive marker in the predictive marker set has a hazards ratio of no more than 0.75.

6. The method of claim 1, wherein the levels of expression of the predictive markers are determined by detection of mRNA.

7. The method of claim 1, wherein the predictive marker set has at least 20 predictive markers from Table 1.

8. The method of claim 7, wherein 60% of the markers demonstrate increased expression.

9. The method of claim 1, wherein the levels of expression of the markers are measured prior to tumor therapy.

10. The method of claim 1, wherein each predictive marker in the predictive marker set has a hazard ratio below 0.65.

11. The method of claim 1, wherein 60% of the markers demonstrate increased expression.

12. The method of claim 1, wherein 80% of the markers demonstrate increased expression.

13. The method of claim 7, wherein 80% of the markers demonstrate increased expression.

14. The method of claim 1, wherein each predictive marker in the predictive marker set has a hazard ratio below 0.50.

15. The method of claim 1, wherein the predictive markers are selected for the predictive marker set by the linear predictive scoring method.

16. The method of claim 5, wherein the predictive marker set has at least 15 predictive markers from Table 1.

17. A method for continuing bortezomib therapy in a multiple myeloma patient, comprising
   a) measuring in a sample from the multiple myeloma patient, wherein the sample is enriched for tumor cells, the level of expression of at least ten predictive markers in a predictive marker set selected from the predictive markers identified in rows 225 to 403 of Table 1, wherein the predictive marker set comprises no more than 150 markers;
   b) comparing the levels of expression of the markers to reference expression levels of each of the markers and detecting increased expression of 50% of the markers of the predictive set in the multiple myeloma patient sample as compared to the reference expression levels; and
   c) treating the multiple myeloma patient with bortezomib.

18. The method of claim 17, wherein the method compares two samples from the patient, wherein a first sample is obtained prior to therapy to determine a baseline of expression and expression in a second sample obtained during therapy is compared to the baseline.

19. The method of claim 17, wherein two or more successive samples are obtained during treatment, wherein the first sample is used as a baseline expression and expression in a successive sample is compared to the baseline.

20. The method of claim 17, wherein each predictive marker in the predictive marker set has a hazards ratio of no more than 0.75.

21. The method of claim 17, wherein 60% of the markers demonstrate increased expression.

* * * * *